US008124025B2

(12) United States Patent  (10) Patent No.: US 8,124,025 B2
Ghai et al.  (45) Date of Patent: Feb. 28, 2012

(54) MEMBRANE SYSTEM FOR BLOOD COAGULATION TESTING

(75) Inventors: Jyotsna Ghai, Plymouth, MN (US); Charlene X. Yuan, St. Paul, MN (US); Wei Qin, Shandong (CN); Mark A. Thompson, Shakopee, MN (US)

(73) Assignee: Medtronic, Inc., Minneapolis, MN (US)

( * ) Notice: Subject to any disclaimer, the term of this patent is extended or adjusted under 35 U.S.C. 154(b) by 1278 days.

(21) Appl. No.: 11/520,338

(22) Filed: Sep. 13, 2006

(65) Prior Publication Data

US 2007/0077612 A1  Apr. 5, 2007

Related U.S. Application Data

(60) Provisional application No. 60/722,834, filed on Sep. 30, 2005.

(51) Int. Cl.
*G01N 21/75* (2006.01)
(52) U.S. Cl. ........ 422/422; 422/400; 422/401; 422/420; 422/421; 422/423; 422/424; 422/425; 422/426; 422/427; 422/428; 422/429; 422/68.1; 422/82.05; 422/82.06; 436/164; 436/169; 436/170; 435/283.1; 435/287.1; 435/287.7; 435/287.8; 435/287.9; 435/288.7; 435/13

(58) Field of Classification Search .............. 422/56, 422/73, 82.07, 82.08, 400, 401, 420, 421, 422/422, 423, 424, 425, 426, 427, 428, 429, 422/68.1, 82.05, 82.06; 436/46, 808, 164, 436/169, 170; 435/4, 13, 283.1, 287.1, 287.7, 435/287.8, 287.9, 288.7
See application file for complete search history.

(56) References Cited

U.S. PATENT DOCUMENTS

| | | | |
|---|---|---|---|
| 4,599,219 A | | 7/1986 | Cooper et al. |
| 5,059,525 A | * | 10/1991 | Bartl et al. ............ 435/13 |
| 5,110,727 A | | 5/1992 | Oberhardt |
| 5,302,348 A | | 4/1994 | Cusack et al. |
| 5,344,754 A | * | 9/1994 | Zweig ................. 435/4 |
| 5,418,141 A | * | 5/1995 | Zweig et al. ........... 435/13 |
| 5,418,143 A | | 5/1995 | Zweig |
| 5,580,744 A | | 12/1996 | Zweig |
| 6,165,795 A | * | 12/2000 | Mize et al. ............ 436/69 |
| 6,750,053 B1 | | 6/2004 | Widrig et al. |

FOREIGN PATENT DOCUMENTS

WO  93/22453  11/1993
WO  95/30770  11/1995

OTHER PUBLICATIONS

Zweig, et al., "Membrane-Based, Dry-Reagent Prothrombin Time Tests," Biomedical Instrumentation & Technology (1996), pp. 245-256.
Bates, et al., "Coagulation Assays," Circulation 2005; 112; 53-60.

* cited by examiner

*Primary Examiner* — In Suk Bullock
*Assistant Examiner* — Dennis M White

(57) ABSTRACT

Articles for testing a coagulation process in whole blood.

61 Claims, 35 Drawing Sheets

MEMBRANE SYSTEM FOR BLOOD COAGULATION TESTING

This application claims priority from U.S. Provisional patent application Ser. No. 60/722,834 filed Sep. 30, 2005, the disclosure of which is incorporated by reference herein.

FIELD OF THE INVENTION

The present invention is related generally to blood coagulation testing, and, more particularly, to a test article and method of measuring blood coagulation and calculating blood coagulation test results.

BACKGROUND OF THE INVENTION

Under normal conditions, blood must remain fluid in order to circulate throughout the body. However, in the event of trauma or vessel damage, such as during surgery, a complex biochemical process known as the coagulation cascade stimulates the blood to form a clot to prevent excess blood loss. To maintain proper blood flow while preventing blood loss at sites of trauma requires a delicate balance of biochemical processes that both stimulate and suppress the coagulation process resulting in necessary but not excessive clot formation. Under appropriate circumstances, this balance can be altered by the use of therapeutic agents to increase or decrease the tendency for clot formation. For example, during cardiac surgery, high doses of heparin are used to prevent the formation of clot while the surgeon manipulates the cardiac vessels.

The coagulation cascade includes two pathways: the intrinsic system or pathway, also known as the contact activation system or pathway, and the extrinsic system or pathway, also known as the tissue factor system or pathway. The intrinsic pathway involves one set of clotting factors (XII, XI, IX, and VIII) and requires the participation of platelets as well as other blood components, such as calcium, in order to progress toward clot formation. Heparin slows clotting by inhibiting processes in the intrinsic system. The extrinsic system involves a different set of clotting factors (III, VII, and V) and, like the intrinsic system, requires the participation of platelets as well as other blood components in order to progress toward clot formation. The oral anticoagulant warfarin acts upon the extrinsic system. The intrinsic and the extrinsic systems join together, forming a common pathway, with both systems causing prothrombin to form thrombin. Thrombin then converts fibrinogen to fibrin, which polymerizes to form a clot, along with activated platelets.

Numerous tests have been developed to evaluate or monitor different portions of the clotting cascade, to assess the clotting capability of blood. These tests can be used to monitor the effect of a particular therapeutic agent or to derive the amount of a therapeutic agent in the blood. For example, the Prothrombin Time, or PT, monitors the extrinsic and common pathways of coagulation, and is useful for monitoring Coumadin therapy. In contrast, the Activated Clotting Time test, or ACT, evaluates the intrinsic and common pathways of coagulation and is useful for monitoring heparin therapy.

Many coagulation tests use clotting initiators specific for a particular portion of the coagulation cascade to stimulate coagulation and then measure the time required for formation of a clot. For example, clot formation may be detected by the change in the viscosity of the blood sample. The increased viscosity may be detected by the change in the flow of the sample through a conduit, such as in U.S. Pat. No. 5,302,348 to Cusack, or by the change in movement of a plunger through a blood sample in a cartridge, as in U.S. Pat. No. 4,599,219 to Cooper and as used in the Medtronic HR-ACT system. Another method detects the increased viscosity of a clotting sample by the movement of magnetic particles in the blood sample in response to a magnetic field, as described in U.S. Pat. No. 5,110,727 to Oberhardt. These tests require clot formation to occur in the blood sample and thus require a waiting period, for as long as is required for the blood to clot before obtaining a result.

Other coagulation tests measure the formation of one of the components of the coagulation cascade, such as thrombin. For example, U.S. Pat. No. 6,750,053 to Widrig Opalsky describes a system that electrochemically detects a substrate acted upon by thrombin. The detection of a component of the coagulation cascade, as opposed to a physical clot, has the advantage of allowing the use of membrane based testing systems. In these systems, a sample of blood is applied to a membrane which contains a substrate. The substrate reacts with a component of the coagulation cascade to produce a detectable reaction or signal. For example, U.S. Pat. No. 5,059,525 to Bartl describes a membrane containing a chromophoric substrate acted upon by thrombin to produce a detectable color change. U.S. Pat. No. 5,418,143 to Zweig and *Membrane-Based, Dry-Reagent Prothrombin Time Tests*, S. Zweig, Biomedical Instrumentation & Technology, 30(3): 245-56 (1996), both of which are incorporated herein by reference, describe an asymmetric membrane, having large pores on one side and small pores on the other side, impregnated with a coagulation initiator and a fluorogenic thrombin substrate. The Zweig membrane allows entry of red blood cells into the membrane through the sample application area on the large pore side of the membrane, but the small pores on the other side of the membrane blocks the cells from passing completely through the membrane. Thrombin, produced by coagulation, reacts with the substrate to produce a fluorescent signal on the detection area of the membrane. The examples disclosed in Zweig illustrate the use of thromboplastin to initiate the extrinsic coagulation pathways for measuring PT, making it useful for monitoring warfarin therapy. The disclosures and teachings of U.S. Pat. Nos. 6,750,053; 5,418,143; 5,302,348; 5,110,727; 5,059,525 and 4,599,219 are incorporated herein by reference.

SUMMARY

The invention provides an article for testing a coagulation process in whole blood, the article having a permeable membrane having a first area including a first pore, a second area including a second pore, and a channel connecting the first pore to the second pore and a substrate associated with the membrane, wherein the substrate is capable of reacting with a coagulation cascade component in the blood to produce a detectable signal on the second area, wherein whole blood may be applied to the first area and the first pore has a smaller diameter than the second pore.

Provided herein is an article for testing a coagulation process in whole blood, the article including a permeable membrane having a first area including pores, a second area including pores and channels connecting the pores of the first area with the pores of the second area and a substrate associated with the membrane, wherein the substrate is capable of reacting with a coagulation cascade component to produce a detectable signal on the second area, wherein whole blood may be applied to the first area and the pores in the first area have a pore size rating of between about 0.1 and about 1 micrometer.

The invention also provides an article for testing a coagulation process in whole blood, the article having a permeable membrane having a first area including pores, a second area including pores and channels connecting the pores of the first area with the pores of the second area and a substrate associated with the membrane, wherein the substrate reacts with a coagulation cascade component in the blood to produce a detectable signal on the second area of the membrane, wherein the pores of the first area substantially exclude red blood cells.

The invention also provides an article for testing a coagulation process in whole blood, the article having a permeable membrane having a first area including pores, a second area including pores and channels connecting the pores of the first area with the pores of the second area and a substrate associated with the membrane, wherein the substrate is capable of reacting with a coagulation cascade component in the blood to produce a detectable signal on the second area of the membrane, wherein the pores of the first area have a smaller diameter than the pores of the second area, wherein the pores of the first area substantially exclude red blood cells and wherein whole blood may be applied to the first area of the membrane.

DETAILED DESCRIPTION OF THE INVENTION

The articles of the embodiments of the present invention comprise a porous and permeable membrane for testing blood coagulation. They include a substrate which reacts with a component of the coagulation process to produce a detectable signal. They include a first membrane area for application of a sample of whole blood, and a second membrane area for detection of the signal. The articles may optionally include a coagulation initiator associated with the membrane. In one embodiment, the article is comprised of multiple membranes.

Figure 1:
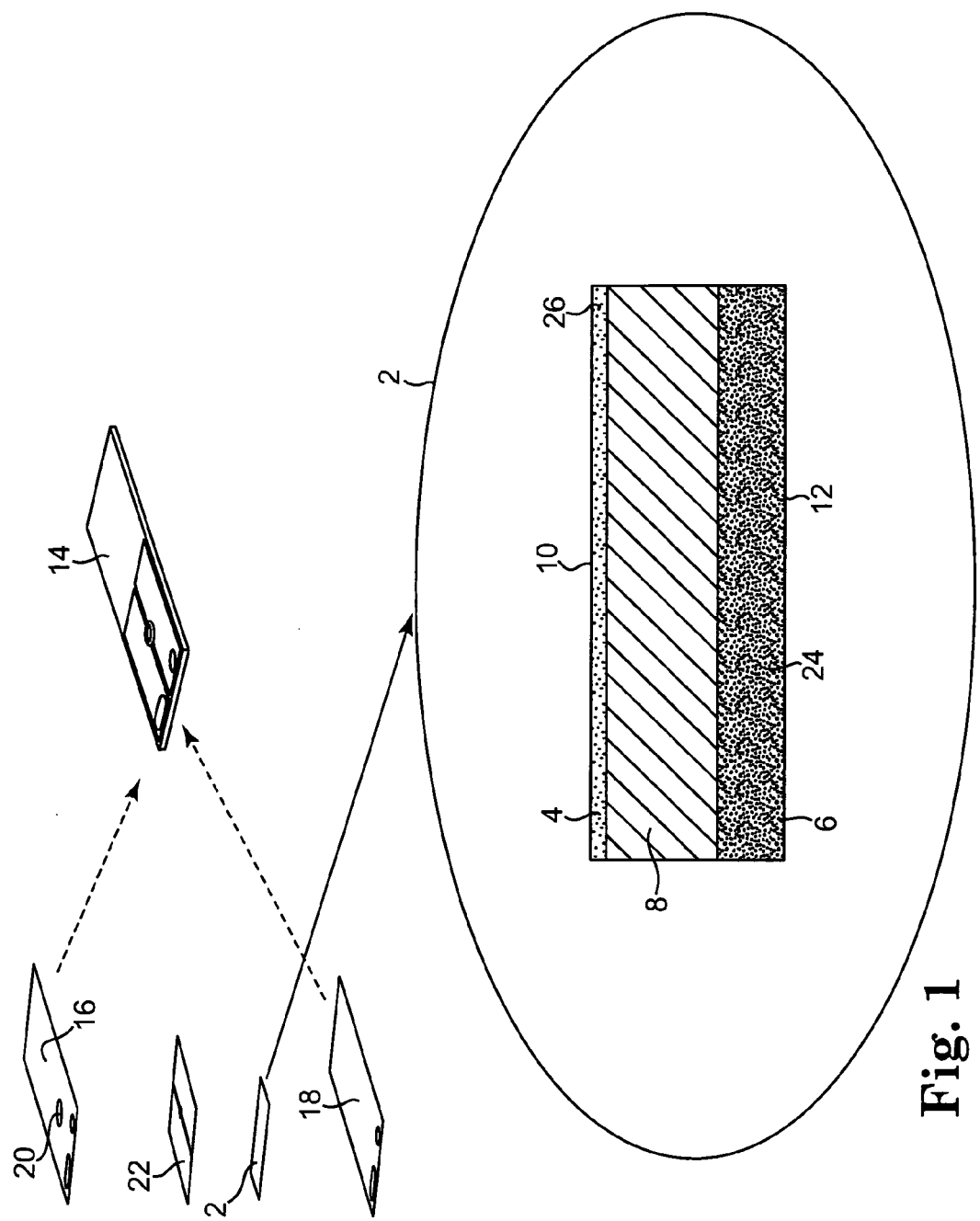
FIG. 1 is an exploded perspective view of a strip including an inset view of a cross section of the membrane.

FIG. 1 shows an article according to an embodiment of the present invention. The membrane 2 includes a top surface, e.g., a smooth side, 4 and a bottom surface, e.g., a rough side, 6. The membrane 2 also includes channels 8 which allow for horizontal and/or lateral flow of a liquid within at least a portion of the membrane 2. The membrane 2 includes a first area 10 for application of a sample of whole blood. The membrane 2 also includes a second area 12 for detection of a signal. The membrane 2 may be assembled into a strip 14 for insertion into a machine for blood coagulation testing. The strip 14 may include a top sheet 16, such as a sheet of plastic, e.g., white plastic, applied to the top surface 4 of the membrane 2 and a bottom sheet 18, which may also be plastic, e.g., clear plastic, applied to the bottom surface 6 of the membrane 2. The top sheet 16 includes a window 20 over the first membrane area 10 through which a sample can be applied to the membrane 2. The bottom sheet 18 must allow for detection of the signal on the second area 12, such as by being transparent over at least the second area 12. The strip may also include a component, such as an aluminum sheet 22, to detect application of the sample to the strip 14. The substrate 24, e.g., thrombin substrate, may be located within the channels 8 and/or on the top surface 4 and/or bottom surface 6 of the membrane 2. In one embodiment, for example, the thrombin substrate is trapped within the membrane. The membrane 2 optionally includes a coagulation initiator 26, which is shown in FIG. 1 located on the first membrane area 10. In one embodiment, for example, the coagulation initiator is a kaolin coating.

The strip 14 can be inserted into a machine for detecting and monitoring signal generation and calculating a coagulation test result. The machine includes a stage for receiving the strip 14. The stage may be heated to maintain the strip 14 at a predetermined temperature so that temperature variations do not influence the rate of coagulation of the blood sample, causing variations in the results. The machine includes a detector which is capable of detecting the signal generated over time and includes a processor for calculating the coagulation test result. The machine may also contain an element for displaying results. In one embodiment, the machine is capable of detecting and calculating test results for more than one type of coagulation test. For example, the machine could detect the signal generated by a thrombin substrate to provide coagulation test results including an Activated Clotting Time, a Prothrombin Time, an International Normalized Ratio (INR), an Activated Partial Thromboplastin Time, an Ecarin Time, or a combination of one or more of these and/or other coagulation tests. The type of test result would depend upon the type of coagulation initiator used with the blood sample. In some embodiments, the signal that the machine detects is fluorescence produced by the substrate 24 after reacting with a component of the coagulation cascade.

The first area 10 and second area 12 of the membrane may be porous and permeable. The membrane 2 allows fluid to flow from one area to the other, such as through channels 8. In one embodiment, the first area 10 is on one surface of the membrane 2 while the second area 12 is on the other surface of the membrane 2 and is directly opposite the first area 10. In another embodiment, the first area 10 and second area 12 are on opposite surfaces of the membrane 2 but are offset rather than in alignment with each other. In another embodiment, the first area 10 and the second area 12 are on the same surface of the membrane 2. This would be the case, for example, in a lateral flow membrane 2. In some embodiments, the invention may include a membrane 2 which is asymmetric, having larger pores on one surface and smaller pores on the other surface.

In another embodiment of the invention, the invention includes two or more membranes 2. In this embodiment, the first membrane area 10 is on the surface of one membrane 2. The second membrane area 12 may be on the surface of the same membrane 2 as the first membrane area 10, or may be on the surface of another membrane 2.

Membranes suitable for use in blood coagulation testing must prohibit red blood cells from passing through the membrane onto the detection area of the membrane. In the past, this was accomplished by using an asymmetric membrane with large pores on the sample application surface of the membrane and small pores on the signal detection area. This orientation was chosen to allow rapid penetration of blood into the membrane channels such that blood coagulation processes occurred inside the channels, with platelets participating in the reaction. The large pore surface of the membrane, also known as the rough side, thus allowed entry of platelets and red blood cells, which are approximately 2 micrometers and 4 to 6 micrometers in diameter, respectively, into the membrane channels. The red blood cells were trapped within the membrane by the small pore surface of the membrane, also known as the smooth side. This prevented the red blood cells from interfering with detection of the signal on the smooth side of the membrane. However, applicants have discovered that this membrane orientation and pore size results in quenching of the fluorescent signal in some circumstances. When the prior art membrane orientation is used to detect fluorescence in an ACT test, and particularly at high heparin levels, results indicate that the fluorescent signal produced by the thrombin was being quenched in the whole blood sample. This effect is increased by the presence of heparin.

While not intending to be bound by theory, applicants believe that this quenching of the signal when the rough side of the membrane receives the sample is due to red blood cell hemolysis. Red blood cells enter the channels 8, where they are trapped during the test and eventually rupture. This hemolysis results in the release of hemoglobin, which passes through the membrane 2 to the detection area of the membrane and interferes with detection of the fluorescent signal. It is believed that hemolysis is more likely to occur when the coagulation test requires more time to complete. This may occur, for example, when clotting time is slowed due to the presence of heparin, especially high heparin levels, or when thrombin levels are decreased due to hemodilution. In addition, certain types of coagulation tests generally require more time to complete than others.

To obtain accurate coagulation test results, accurate fluorescence levels must be obtained which correspond to the levels of the coagulation cascade component. Quenching blocks detection of signal, masking actual levels of the coagulation cascade component. As a result, accurate levels cannot be measured and coagulation test results cannot be obtained.

By reversing the orientation of the asymmetric membrane 2, such that the blood samples are applied to the smooth surface of the membrane 2, fluorescent signal detection is greatly improved. The smooth side of the membrane 2 substantially excludes red blood cells such that they do not enter the membrane channels 8. Thus when the smooth side of the membrane provides the first membrane area 10 for sample application, red blood cells do not enter the channels 8 but remain on the surface of the membrane, reducing or eliminating signal quenching. As a result of decreased signal quenching, fluorescence measurements may be taken to provide accurate coagulation test results. This improvement is particularly important in coagulation tests which require more time to complete and for samples with higher states of anticoagulation, where it appears that more red blood cell hemolysis occurs, causing greater interference with the fluorescence monitoring.

By choosing the appropriate pore size, the red blood cell quenching of the fluorescent signal is reduced. In one aspect of the invention, the membrane 2 provides pores on the first area 10 which minimize red blood cell hemolysis. In another aspect of the invention, the membrane 2 is an asymmetric membrane and the orientation of the membrane 2 is such that first membrane area 10 is on the smooth surface of the membrane.

Membranes 2 suitable for one or more embodiments of this invention may contain pores with a pore size rating of less than about 1 micrometer. However, the methods of the invention may be practiced utilizing membranes outside of this range. As used herein, the pore size rating is the absolute pore size rating. The pore size rating is the size of a particle that is retained by a membrane more than 99% of the time. For example, a membrane with a pore size rating of 1 micrometer will retain (prevent from passing) more than about 99% of particles 1 micrometer or larger. For asymmetric membranes 2, the pore size rating is the pore size rating of the smooth side of the membrane, not the pore size rating of the rough side, which has larger pores. An appropriate range of pore size rating suitable for the embodiments of this invention is between about 0.1 micrometer and about 1 micrometer. If an asymmetric membrane 2 is used, at least one surface of the membrane 2 should have pores with a pore size rating between about 0.1 micrometer and about 1 micrometer. For some embodiments of the invention, the smooth side of the asymmetric membrane 2 will provide the first membrane area 10. The first membrane area 10 may contain pores with a pore size rating which is between about 0.4 micrometer and about 0.6 micrometers. In another embodiment, the first membrane area 10 may have a pore size rating of approximately 0.6 micrometers.

Although the use of small pore sizes that filter red blood cells results in decreased quenching of the fluorescent signal, cellular components important for coagulation may be filtered by small pore sizes below a certain threshold. For example, platelets are filtered by pores less than 1 or 2 micrometers. Thus the use of pores less than 1 or 2 micrometers results in platelets being substantially excluded from the channels 8 of the membrane 2. In prior art membranes which used larger pores on the sample application area, cellular components were not excluded but rather participated in the coagulation reaction inside the membrane channels.

Platelets are necessary for the normal coagulation cascade to occur in order to obtain appropriate measurable results. When a sample of plasma which lacks platelets is used for fluorescence detection in an ACT test in accordance with one embodiment of the invention, the plasma produces less fluorescence than a sample of fresh whole blood. Thus the use of small pores, for example with a pore size rating of less than 1 micrometer, results in decreased hemolysis and improved signal generation. However, the decreased quenching of signal with the small pores also results in exclusion of platelets which are needed for coagulation to proceed normally. Under the prior art system in which the coagulation initiator was located within the membrane channels, the lack of platelet participation due to small pores would have been problematic.

The optimum pore size must minimize hemolysis to prevent signal quenching. Because this optimum size is so small that it can prevent entry of cellular components into the channels 8 of the membranes 2, the article must allow the participation of the cellular components in some other way. One method of allowing platelet participation in a system that substantially filters them from the membrane channels 8 is by adding the coagulation initiator 26 to the sample prior to applying the sample to the membrane 2. In this way, coagulation is stimulated and the cellular components participate in the reaction prior to the cellular components being filtered by small pores on the first membrane area 10. In another alternative, the coagulation initiator 26 is immobilized on the first membrane area 10, where the sample is applied, and stimulates coagulation prior to the cellular components being filtered by the small pores on the first membrane area 10.

The coagulation initiators 26 are substances which stimulate the whole blood sample to coagulate. The choice of coagulation initiator 26 will depend upon which portion of coagulation cascade is being evaluated. For example, to measure an ACT, a particulate contact activator would be an appropriate coagulation initiator 26. Examples of coagulation initiators 26 include ellagic acid, silica, thromboplastin, ecarin, Russell's viper venom, phospholipids such as phosphatidylcholine, phosphatidylserine, phosphatidylethanolamine, sulfatides and particulate contact activators such as kaolin and Celite. The choice of initiator 26 will determine the type of coagulation test for which the results may be used. In addition, a combination of coagulation initiators 26 may be used. For example, kaolin may be used in combination with phosphatidylcholine as a co-activator.

In one embodiment of the invention the coagulation initiator 26 is added to the whole blood sample prior to application of the sample to the membrane 2. In an alternative embodiment of the invention, the coagulation initiator 26 is associated with the membrane 2 and the whole blood sample contacts the coagulation initiator 26 after the sample is applied to the membrane. The coagulation initiator 26 may be located on the first membrane area 10, the second membrane area 12, in the membrane channels 8, or a combination of these locations. In some embodiments, the coagulation initiator is preferably located on the first membrane area 10.

The coagulation initiator 26 stimulates the coagulation cascade by contact between the coagulation initiator 26 and the whole blood sample. It is after this point, when coagulation is initiated, that the participation of cellular components is needed in order to obtain a normal coagulation result. Thus there must be contact between the cellular components, such as the platelets, and the sample after the sample has been in contact with the coagulation initiator 26. Therefore, the use of a membrane 2 that excludes cellular components from entering the membrane channels 8, along with placement of the coagulation initiator 26 inside the channels 8, would result in failure of the cellular components to participate in coagulation, leading to poor results.

In one embodiment of the invention, a dry coagulation initiator 26 is immobilized on the first area 10 of the membrane 2. During testing of a sample of whole blood, the sample is applied to the first area 10 of the membrane 2, thus contacting the coagulation initiator 26. In this way, coagulation is initiated before the sample enters the channels 8 of the membrane and the cellular components of the sample can participate in coagulation on the first area 10 of the membrane 2. This arrangement allows for the use of pore sizes which substantially exclude the cellular components but still allows for participation of the cellular components in the coagulation reaction.

One useful type of coagulation initiator 26 is kaolin, a clay material formed of fine particles. As a particulate contact activator, it does not dissolve into a liquid solution but rather the kaolin particles form a suspension in a liquid. This kaolin suspension, like other contact activators, requires constant stirring to maintain the kaolin evenly distributed throughout the suspension, making application of the kaolin to the membrane system challenging. If the membrane is dipped in the kaolin suspension, it will result in uneven and unpredictable coating of the membrane. Furthermore, because the kaolin is a clay, it will clog the membrane pores and channels, making it impossible for the sample to penetrate through the channels to the second membrane area for signal detection. When kaolin is applied to the membrane by pipetting drops of a kaolin suspension onto the membrane, the results are also inadequate. Application of kaolin suspension by pipette results in the kaolin piling up and forming a clay layer on the surface of the membrane. The pipetted kaolin thus forms an irregular layer that blocks passage of the sample into the membrane. For use in the membrane system, the coagulation initiator 26 should activate the sample and allow the sample to flow through it, but this does not occur with the prior art membrane coating systems of dipping and pipetting.

In order to function in a membrane system, a particulate contact activator such as dry kaolin must be finely and evenly distributed on the membrane 2. It may be on either the first membrane area 10, the second membrane area 12, or both membrane areas. Kaolin may be applied to the first area 10 of the membrane 2 so that the blood sample flows through the kaolin, passing between the kaolin particles such that coagulation is initiated before the sample enters the membrane 2.

One manner of applying a particulate contact activator such as kaolin to the membrane is by rubbing dry kaolin onto one or more membrane surfaces. Application in this way produces a finely and evenly distributed layer of coagulation initiator, allowing the sample to flow through it. For example, dry kaolin powder may be rubbed onto the surface using any device that allows the dry kaolin to transfer to the membrane surface. One method of rubbing the dry kaolin is by brushing the kaolin onto the membrane 2 with a brush, such as a paint brush. Another method of rubbing the dry kaolin onto the membrane surface is by using a finger. The dry kaolin may be rubbed onto the first area 10 or both the first area 10 and second area 12 of the membrane in order to initiate coagulation of the blood sample. After application, the excess kaolin may be removed, for example by brushing off the loose kaolin. The membrane 2 may be weighed before and after the coagulation initiator application to determine the net weight gain, which is the amount of kaolin immobilized on the membrane 2.

Optimal fluorescence results may depend on the amount of kaolin rubbed onto the membrane 2. Application by rubbing on dry kaolin in an amount that increases the weight of the membrane 2 by from about 2% to about 20% results in measurable fluorescence. An approximately 20% increase is appropriate in certain embodiments. For membranes 2 to which dry kaolin has been applied, good fluorescence results can be obtained with calcium concentrations of about 30 mM to about 50 mM in the substrate solution, preferably about 50 mM, but higher or lower than this concentration range may also provide good results.

A particulate contact activator such as kaolin may also be applied to an area of the membrane 2 in a suspension as fine droplets or as a fine mist in order to provide an even and uniform distribution. It may be formed into a mist by providing kaolin suspension in an aerosol spray, such as through the use of an airbrush. When the suspension is applied by an airbrush, it must be stirred constantly prior to aerosolization. It is preferable to keep the length of tubing between the suspension and the airbrush nozzle short in order to avoid settlement in the tubing. To keep the amount of particulate contact activator applied to the membrane 2 uniform from one membrane application to the next, the distance from the airbrush nozzle to the membrane, the compressed air pressure, and the spray time may all be fixed.

When kaolin is applied to the membrane 2 by an airbrush, the amount applied can be determined by the net weight gain of the membrane. The amount of kaolin or other particulate contact activator applied to the membrane may be adjusted by varying the concentration of kaolin in the suspension. Kaolin suspensions with concentrations from about 4% to about 12% produce good fluorescence results when applied by airbrush. A 12% kaolin suspension is preferable, with concentrations higher than 12% also giving good results but not significantly better than the 12% suspension.

The amount of kaolin or other particulate activator applied to a membrane by airbrushing may also be adjusted by applying one application of kaolin or by repeating the number of applications to two or more times. Either regular kaolin, with an average particle size of about 1.4 micrometers, or ultrafine kaolin, with an average particle size of about 0.6 micrometers, may be used. However, ultrafine kaolin may be preferable because it can form a better aerosol. When kaolin is applied by airbrush, good fluorescence results can be obtained with kaolin suspensions including calcium concentrations from about 10 mM to about 50 mM, preferably about 30 mM, but concentrations higher or lower than this range may also provide good results.

One example of preparing a membrane of this invention is as follows. A 12% suspension of ultrafine kaolin is prepared using a HEPES buffer at pH 7.4 with 50 mM Calcium. The container for the kaolin suspension is fixed on a stir plate and the suspension is stirred constantly. The container for the kaolin suspension is connected to an airbrush by approximately 2 inches of tubing. The compressed air of the airbrush is held at 10 psi. If the membrane 2 has been into pre-assembled strip 14 including a sheet of plastic on each area of the membrane 2, a portion of the plastic film must be removed to create a window 20 onto which the kaolin suspension will be sprayed. The membrane 2 or strip 14 is held in a vertical position to receive the kaolin suspension spray. For more reproducible and consistent results, a fixture may be used to hold the membrane 2 or the strip 14 at a controlled distance from the airbrush and to allow repeatable alignment of the target and the airbrush. In addition, an electronic device may be used to control the duration of the shot of the airbrush discharge. The desired amount of kaolin may be applied to the membrane 2 or strip 14 in a single airbrush discharge or in multiple airbrush discharges. The membrane 2 or strip 14 is allowed to dry before being used for testing.

Other methods for the application of a fine layer of a particulate contact activator to the membrane 2 or strip 14 include, but are not limited to, electrodeposition, electrostatic coating, ultrasonic atomization and coating, airless sprayer, and acoustic micro-dispensing.

The substrates 24 of the preferred embodiments of the present invention are substances which react with a component of the coagulation cascade to produce a detectable signal. Suitable substrates 24 for monitoring the coagulation reaction include certain derivatized proteins which are activated by a component of the coagulation cascade, such as thrombin. Thrombin, which is produced as a result of both the intrinsic and extrinsic pathways, is one component of the coagulation which, as an enzymatic protein, is suitable to react with the substrate 24. However, other components of the coagulation cascade, such as Factor Xa, could also interact with the substrate 24 and could be used to monitor different portions of the coagulation cascade.

It is particularly useful to monitor thrombin because thrombin participates in the common pathway of coagulation and reacts with fibrinogen to form fibrin, which forms the clot. Thus, because it is only one step removed in the coagulation cascade from clot formation, it acts as a good substitute for clot detection. It also allows monitoring of both intrinsic and extrinsic pathways. Thus, a detector which detects thrombin may be used to perform multiple coagulation tests, depending on the type of coagulation initiator 26 used on the strip 14. For example, a strip 14 could use thromboplastin as a coagulation initiator 26 and could use a thrombin substrate for detecting thrombin generation to obtaining a PT result. Another strip 14 could use kaolin as a coagulation initiator and could use the same thrombin substrate for detecting thrombin generation to obtain an ACT result. A single machine could therefore detect results for both types of strips 14, since both use the same substrate and generate the same type of signal.

The substrate 24 may include a peptide which is cleavably linked to a reporter molecule, such as a chromatogenic, chemiluminescent, or fluorogenic molecule. The component of the coagulation process is able to recognize the substrate peptide and cleave a cleavable linker which causes a change in the reporter molecule, resulting in a detectable signal, such as color change, light emission, or fluorescence. When the detectable signal is fluorescence, the machine for detecting the fluorescence includes a light source to direct light onto the second area 12 of the membrane 2. The light is absorbed by the substrate reporter molecule which then emits light as fluorescence at a particular wavelength. The intensity of the emitted light at that wavelength is detected by the detector. The machine may also contain filters between the light source and the membrane 2 and/or between the membrane 2 and the detector.

There are numerous suitable substrate peptides useful in embodiments of this invention. The choice of substrate peptide will depend upon the type of test being performed and on the coagulation cascade component being generated and monitored by the test. Thrombin acts upon numerous substrate peptides including Tos-Gly-Pro-Arg, 2AcOH.H-D-CHA-But-Arg, 2AcOH.H-D-CHG-Ala-Arg, 2AcOH.H-D-CHG-Gly-Arg, 2AcOH.H-D-CHG-But-Arg, 2AcOH.H-D-HHT-Ala-Arg, 2AcOH.H-D-CHT-But-Arg, 2AcOH.H-D-CHG-Pro-Arg, 2AcOH.H-D-CHA-Ala-Arg, 2AcOH.H-D-CHT-Gly-Arg, 2AcOH.H-D-CHA-Gly-Arg, 2AcOH.H-D-CHA-Nva-Arg, $CH_3OCO$-Gly-Pro-Arg, 2AcOH.H-D-Lys(Bz)-Pro-Arg, 2AcOH.H-β-Ala-Gly-Arg, 2AcOH.H-D-CHG-Leu-Arg, 2AcOH.H-D-CHA-Ala-Arg. Substrate peptides for Factor Xa include $CH_3SO_2$-D-Leu-Gly-Arg, $CH_3OCO$-D-Nle-Gly-Arg, $CH_3OCO$-D-CHG-Gly-Arg, $CH_3OCO$-D-Val-Gly-Arg, $C_2H_5OCO$-D-Val-Gly-Arg, $CH_3OCO$-D-CHA-Gly-Arg, $CH_3OCO$-D-Leu-Gly-Arg. All of the above listed substrates peptides may be used in embodiments of this invention and can be attached to Rhodamine 110, other fluorophores or other reporter molecules.

As explained below, in some circumstances it may be preferable to select a peptide with weak affinity for the coagulation cascade component in order to decrease competition for the coagulation cascade component. Suitable substrate reporter molecules includes fluorogenic molecules such as Rhodamine-110, Rhodamine derivatives such as tetramethylrhodamine-5-(and 6)-isothiocyanate (TRITC), Fluorescein and Fluorescein derivatives such as Fluorescein Isothiocyanate (FITC), 7-amido-4-methylcoumarin and coumarin derivatives, aminoquinolines, aminonaphthalenes, benzofurazans, acridines, BODIPY and BODIPY derivatives, Cascade Blue and Cascade Blue derivatives (BODIPY and Cascade Blue are registered trademarks of Molecular Probes; U.S. Pat. No. 4,774,339), Lucifer Yellow and Lucifer Yellow derivatives, and Phycobiliproteins and their derivatives The choice of the substrate reporter molecule may also be effected by the need to avoid interaction between the coagulation initiator and the substrate reporter molecule, as described below.

The usefulness of different coagulation initiators and different substrates allows the membrane to be used with a wide variety of tests. In one embodiment of this invention, a coagulation initiator 26 such as kaolin, celite, silica or sulfatide is used to initiate coagulation, and a thrombin substrate is used to detect thrombin generation. The results are used to derive an ACT, which can be used to monitor the anticoagulant effect of drugs such as heparin as well as direct thrombin inhibitors such as Angiomax® (TRADEMARK NAME for bivalirudin, The Medicines Company Massachusetts, USA).

In another embodiment of the invention, coagulation initiators 26 such as phospholipids, silica, and ellagic acid are used along with a thrombin substrate, and thrombin generation is used to derive an Activated Partial Thromboplastin Time. This type of test would be used for monitoring the effect of low dose heparin as well for diagnosing coagulation factor deficiencies.

In another embodiment of the invention, a Factor X specific clotting time is derived from the generation of Factor Xa. This test would employ a coagulation initiator 26 such as Russell's viper venom, and a Factor Xa substrate, and could be used to monitor factor Xa specific drugs, such as low molecular weight heparin, as well as lupus anticoagulants.

In another embodiment of the invention, an Ecarin Clotting Time is derived from the generation of thrombin, detected by a thrombin substrate. Coagulation initiators 26 useful in this embodiment include, for example, Ecarin and phospholipid. The results would be useful for monitoring the effect of direct thrombin inhibitors, such as hirudin and bivalirudin.

In another embodiment of the invention, no coagulation initiator is used. Rather the blood sample is supplemented with a component of the coagulation cascade such as thrombin or Factor Xa. The coagulation cascade component could be added to the sample before application to the membrane 2, or could be incorporated into or onto the membrane 2. In one example, Factor Xa is added to the blood sample or to the membrane and a thrombin substrate is used on and/or in the membrane 2. The results can be used to derive a quantitative heparin concentration. In another example, thrombin is added to the blood sample or the membrane 2, and a thrombin substrate is used. The results of this example may be used for an Anti-IIa test from which the concentration of direct thrombin inhibitors such as Bivalirudin and Hirudin can be determined.

In one embodiment of the invention, dry kaolin is the coagulation initiator 26 and it is immobilized on the first area 10 of the membrane 2, the pores of the first membrane area exclude red blood cells and platelets, and (Tos-Gly-Pro-Arg)$_2$- Rhodamine-110 is a thrombin substrate on the second membrane area 12. In this embodiment, a sample of whole blood is applied to the first membrane area 10 where kaolin stimulates the extrinsic coagulation pathway, leading to the formation of thrombin. Plasma from the sample filters through the membrane channels 8 to the second membrane area 12, where thrombin reacts with the (Tos-Gly-Pro-Arg)$_2$-Rhodamine-110 to produce a fluorescent signal. The time required for the fluorescent to increase is used to calculate an ACT.

A reaction can occur between certain coagulation initiators 26 and certain substrates 24 which interferes with signal detection. Kaolin and other contact pathway initiators have negatively charges surfaces. However, fluorophores such as Rhodamine-110 are positively charged after they are released from the thrombin substrate. This difference in charge allows for an electrostatic interaction between the contact pathway initiator and the fluorescent reporter molecule, resulting in reduced signal generation by the fluorophore. Therefore it is preferable to avoid or minimize an interaction between the fluorophore and the coagulation initiator 26 so that coagulation can be detected by signal generation.

Use of a fluorophore that is neutral or negatively charged after release from the substrate avoids this detrimental interaction. Examples of neutral and negative fluorophores include Fluorescein, FITC and their derivatives, as well as any fluorophore that does not have a positive charge when released from the substrate. By using a neutral or negatively charged fluorophore, the electrostatic interaction with the negatively charged coagulation initiator 26 is avoided, allowing for unhindered signal detection.

Physical separation of the substrate 24 and the coagulation initiator 26 is another way to avoid an interaction between the coagulation initiator 26 and the substrate 24. This may be accomplished, for example, through the use of more than one membrane 2, through placement of the coagulation initiator 26 and the substrate 24 at different locations on the membrane 2, through use of a lateral flow system, or combinations thereof.

In some embodiments of the invention, two or more membranes 2 are used. In such embodiments, the surface of one membrane 2 may be in contact with the surface of the other membrane in a manner that allows flow of sample from one membrane 2 to the other. In some embodiments, the membrane surfaces may be joined by an adhesive. The adhesive may bind the membranes together and may improve flow of the sample from one membrane 2 into the other. Examples of suitable adhesives include sugars, such as trehalose and sucrose, and polymer containing buffers, such as a combination of Hepes, BSA and PVA buffer. Each membrane 2 may be configured with either the small pore and large pore side facing either direction. One double membrane embodiment includes a BTS-25 upper membrane 2 which provides a first membrane area 10 for sample application on the rough side of the membrane 2. The smooth side of the upper membrane 2 is adhered by a sugar to the smooth area of the lower membrane 2, also a BTS-25 membrane. By applying the adhesive to the smooth sides of the membranes 2 such that the smooth sides of the membranes 2 are adhered together, the adhesive may adhere the membranes 2 better than when applied to the rough surface of the membranes 2. This may be because the adhesive remains on the surface of smooth side to provide adhesion, but the adhesive may enter the larger membrane pores of rough side of the membrane 2 when applied to that side, therefore providing less adhesion.

In some embodiments of the invention in which there are two or more membranes 2, the sample is premixed with the coagulation initiator 26 prior to application of the sample to the first membrane area. In such embodiments, the substrate may be located on one or both surfaces and/or in the channels of one of the membranes 2. Alternatively, the substrate 24 may be located on one or both surfaces and/or in the channels 8 of two or more of the membranes 2. The location of the substrate 24 is flexible because the coagulation initiator 26 is combined with the sample prior to application of the sample to the first area of the membrane 2.

In yet other embodiments of the invention in which there are two or more membranes 2, the coagulation initiator 26 is associated with the first membrane 2 and the substrate 24 is associated with the second membrane 2. The first membrane 2 provides the first membrane area 10, and the second membrane 2 provides the second membrane area 12. The coagulation initiator 26 may be on either surface of the first membrane 2, on both surfaces, and/or inside the membrane channels 8. The substrate 24 may be on either surface of the second membrane 2, on both surfaces, and/or in the membrane channels 8. This configuration separates the coagulation initiator 26 from the substrate 24 to prevent an interaction which could interfere with signal detection.

In other embodiments of the invention, the membrane 2 is designed as a lateral flow system. As with horizontal membrane systems, the lateral flow membrane 2 preferably has pores to filter cellular components out of the whole blood sample. The lateral flow membrane has channels 8 to allow lateral flow of a sample. As with the horizontal membrane 2, the lateral flow membrane 2 may be asymmetric. According to such lateral flow embodiments, the coagulation initiator 26 is applied to the first area 10 of the membrane 2. Red blood cells are filtered by the pores of the first membrane area 10 while the plasma flows into the membrane 2 and laterally to the second membrane area 12 for signal detection. The second membrane area 12 may be on the same surface of the membrane 2 as the first membrane area 10 or it may be on the opposite surface of the membrane 2. The substrate 24 may be located inside the membrane channels 8 or on the first 10 or second membrane areas 12. The location of the substrate 24 inside the lateral flow channels 8 or in the second area 12 separates the coagulation initiator 26 on the first area from the substrate 24, preventing or minimizing any interaction between the coagulation initiator 26 and the substrate 24 and is therefore preferred in embodiments where such interactions are an issue. For optimum results in some embodiments, the membrane 2 should have the ability to filter cellular components as well as provide good lateral flow for plasma, while not interfering with the coagulation reaction.

The use of this invention for measuring ACT provides a means of assessing heparin concentrations in a sample of fresh whole blood. Heparin functions at several locations in the coagulation cascade. One important way in which heparin slows coagulation is through its effect on thrombin. Heparin acts to catalyze a reaction between two molecules of thrombin and one of ATIII (Antithrombin III) to form the TAT complex. As a result, there is less thrombin present to participate in coagulation, and therefore blood takes longer to clot.

When a membrane system uses a thrombin substrate to monitor heparin levels, the thrombin substrate may compete with heparin. At the same time as heparin is catalyzing formation of the TAT complex, the substrate 24 is using thrombin to generate a signal. As a result, the thrombin substrate can interfere with test results by producing a signal indicating thrombin levels before heparin has acted to fully decrease thrombin. This may result in quicker and higher than expected levels of fluorescence, or thrombin levels, for samples containing heparin.

The competition between the thrombin substrate and heparin results in the need to carefully optimize the amount of thrombin substrate used in the membranes 2. Increasing the amount of thrombin substrate results in a faster rise in fluorescence, but also results in a loss of distinction between different levels of heparin due to the substrate 24 dominating over the heparin in competition for thrombin. As a result, the prolongation in time for fluorescence to increase expected for samples with higher heparin levels is lost. In contrast, when the amount of thrombin substrate is too low, the rise in fluorescence is slow and the fluorescence intensity is low. Substrate solutions with concentrations from about 0.1 mM to about 0.2 mM are preferred for coating onto the rough side of membranes 2 which will be airbrushed with, for example, a 12% kaolin suspension onto the smooth side of the membrane 2. Thus in one aspect of this invention, thrombin substrate competition with heparin is reduced by using optimized substrate 24 levels. Use of the optimal amount of substrate 24 is critical to obtaining fast and accurate measurements of heparin levels.

Another method for decreasing thrombin substrate competition with heparin is by delaying the substrate reaction. After the blood sample contacts the coagulation initiator 24, the coagulation process proceeds to generate thrombin. By delaying the substrate reaction, there is more time for heparin to act upon thrombin to form the TAT complex, reducing thrombin levels. After this period of delay, the substrate 24 contacts the sample and produces results reflecting the reduced thrombin levels due to the presence of heparin.

The substrate reaction may be delayed by physically separating the coagulation initiator 26 and the substrate 24. This may be done by any of the methods described above for preventing an interaction between the coagulation initiator 26 and the substrate 24. Thus, the coagulation initiator 26 may not be included in the membrane 2 but may be added to the sample prior to application of the sample to the membrane. Alternatively, the coagulation initiator 26 and the substrate 24 may be coated on different sides of the membrane 2. In another alternative, the invention may use a lateral flow membrane, with the coagulation initiator 26 present on one part of the membrane 2 and the sample flowing laterally to another part of the membrane 2 to contact the substrate 24. In another alternative, the invention may employ more than one membrane 2, with the coagulation initiator 26 associated with one membrane 2 and the substrate 24 associated with a different membrane 2.

Another way of delaying the thrombin substrate reaction is by slowing the flow of the sample through the membrane 2. This can be accomplished through the use of smaller pores, which slow the entry of the sample into the membrane 2. Slower entry of the sample into the membrane 2 allows more time for the coagulation cascade to proceed on the surface of the membrane 2 prior to the sample contacting the substrate 24 in the membrane channels 8 and/or on the second area 12 of the membrane 2.

The substrate competition for thrombin may also be reduced by using a substrate peptide that interacts more weakly with thrombin. Preferably the interaction between the substrate peptide and thrombin is weaker than the heparin catalyzed interaction between ATIII and thrombin. Thus the ATIII interacts with thrombin to reduce thrombin levels with little effect by or competition with the thrombin substrate. The weaker substrate reacts with whatever thrombin remains after the heparin catalyzed interaction with ATIII.

The effect of substrate competition for thrombin may also be reduced by encouraging the reaction between thrombin and Antithrombin II (ATIII). One way of encouraging this reaction is by supplementing the reaction with additional ATIII. The addition of ATIII encourages the heparin catalyzed conversion of Thrombin and ATIII into the TAT complex, which results in decreased thrombin levels. The addition of ATIII to the reaction ensures that there is sufficient ATIII present to react with thrombin at a rate that depends on the amount of heparin present in the sample. Thus thrombin levels are decreased in relation to the amount of heparin present in the sample. If ATIII levels present in the unsupplemented sample are insufficient for heparin to quickly convert the thrombin and ATIII to the TAT complex, there is an increased opportunity for the thrombin to react with the substrate and produce fluorescence. ATIII may be added to the sample prior to sample application to the first membrane area 10. Alternatively, the ATIII is associated with the membrane 2. The ATIII may be located on the first membrane area 10, the second membrane area 12, in the membrane channels 8, or in any combination of these locations.

In addition to the substrate 24 and the coagulation initiator 26, the membrane 2 may have other substances associated with it to aid the reaction and/or to improve sample flow. For example, the presence of calcium in optimum amounts is essential to certain reactions of the coagulation cascade. Buffers, such as Hepes, Tris, MOPSO or other organic acid/base buffers or inorganic acid/base buffers may also be associated with the membrane 2. The buffer preferably includes Bovine Serum Albumin and polyvinyl alcohol. It is believed that the Bovine Serum Albumin act as a protein stabilizer/carrier, while the polyvinyl alcohol improves the coagulation reaction by preventing diffusion and spreading of the blood sample after application of the sample to the membrane 2. Other components which may be associated with the membrane 2 include flow control agents to decrease chromatographic separation of blood proteins entering the membrane, cofactors to sustain or enhance the chemical reactions of the coagulation cascade, stability enhancers, and pigments to enhance the optical characteristics. These components may be applied to the membrane 2 in a solution form together with the substrate 24 or may be applied to the membrane 2 separately.

In one aspect of this invention, the membrane 2 further comprises a heparin inactivating agent. The heparin inactivating agent removes the effect of at least one type of heparin from the blood. This makes the heparin inactivating agent an ideal tool for use in coagulation tests when a patient's blood is affected by more than one type of anticoagulation therapy. Different anticoagulants can have overlapping effects on the various coagulation tests, making it difficult to decipher how much of each anticoagulant is present in a sample. By eliminating the effect of heparin, the heparin inactivating agent can help clarify the results.

The heparin inactivating agent Heparinase, available from IBEX (IBEX Pharmaceuticals, Inc., Montreal, Quebec, Canada), may be added to the membrane of this invention. Heparinase removes the effect of both unfractionated heparin as well as low molecular weight heparin. It is therefore useful where patients receive different types of heparin, such as when moving from the emergency room, where they might receive low molecular weight heparin, to the cardiovascular operating room where they might receive heparin. Other heparin inactivating agents, such as Polybrene (Sigma-Aldrich, St. Louis, Mo.) might also be suitable. However, Heparinase is effective for removing the effect of low molecular weight heparin and unfractionated heparin and is therefore preferred over agents which only remove the effect of unfractionated heparin.

The membrane 2 including the heparin inactivating agent is useful to measure PT. The PT is a test frequently used to monitor anticoagulation due to warfarin therapy. However, heparin can also cause a prolongation of the PT. Thus, when a patient on warfarin therapy has also received heparin, the PT will be prolonged more than it would be due to warfarin alone. It is difficult for the practitioner to know what part of the PT prolongation is due to warfarin and what part is due to heparin. As used in this invention, heparinase is associated with a membrane 2 used for measuring PT. The addition of heparinase to the membrane 2 produces a result that reflects anticoagulation produced by warfarin only, regardless of whether heparin is present.

The membrane 2 for measuring PT including Heparinase of this invention may be produced by the following procedure. A solution of thromboplastin is made. This solution may include a buffer, such as a BSA/PVA buffer. A heparinase solution is made, either in combination with the thromboplastin solution or as a separate solution. The heparinase solution may also include a buffer, such as a BSA/PVA buffer. The concentration of the heparinase is such that the final amount of heparinase on the membrane will be sufficient to neutralize the heparin present in the sample.

The time to result is an important aspect of coagulation tests. It is often desirable for clinicians to obtain the results from coagulation tests as quickly as possible. However, since a typical coagulation test is not complete until clot formation has occurred, the time required to obtain a result can be long, such as several minutes, particularly when the blood sample has been anticoagulated and is therefore slower to clot. Even prior art methods which detect thrombin formation, rather than clot formation, are not complete until thrombin formation has reached its maximum in order to calculate the result. For tests such as the ACT, which typically requires a longer time to result, the delay while waiting for the test result is significant. Therefore it is desirable to obtain results of coagulation tests more quickly. Quicker results are particularly desirable in clinical situations where physicians must closely monitor coagulation test results in order to adjust anticoagulant therapy, such as in the cardiovascular operating room.

Figure 7:
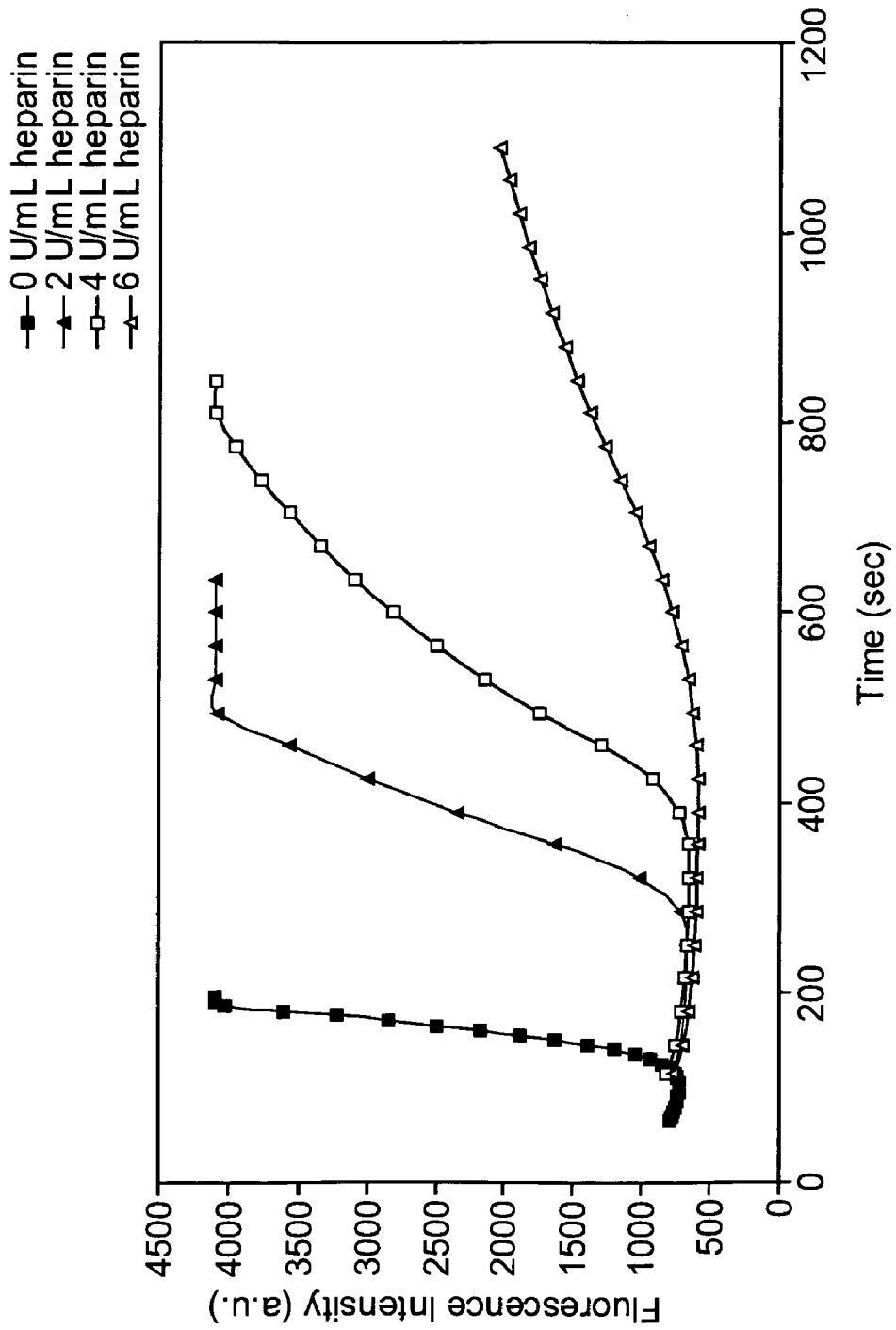
FIG. 7 is a graph of fluorescence versus time for samples of fresh whole blood at various heparin levels in basic buffer with the smooth side of the membrane receiving the samples.
Figure 15:
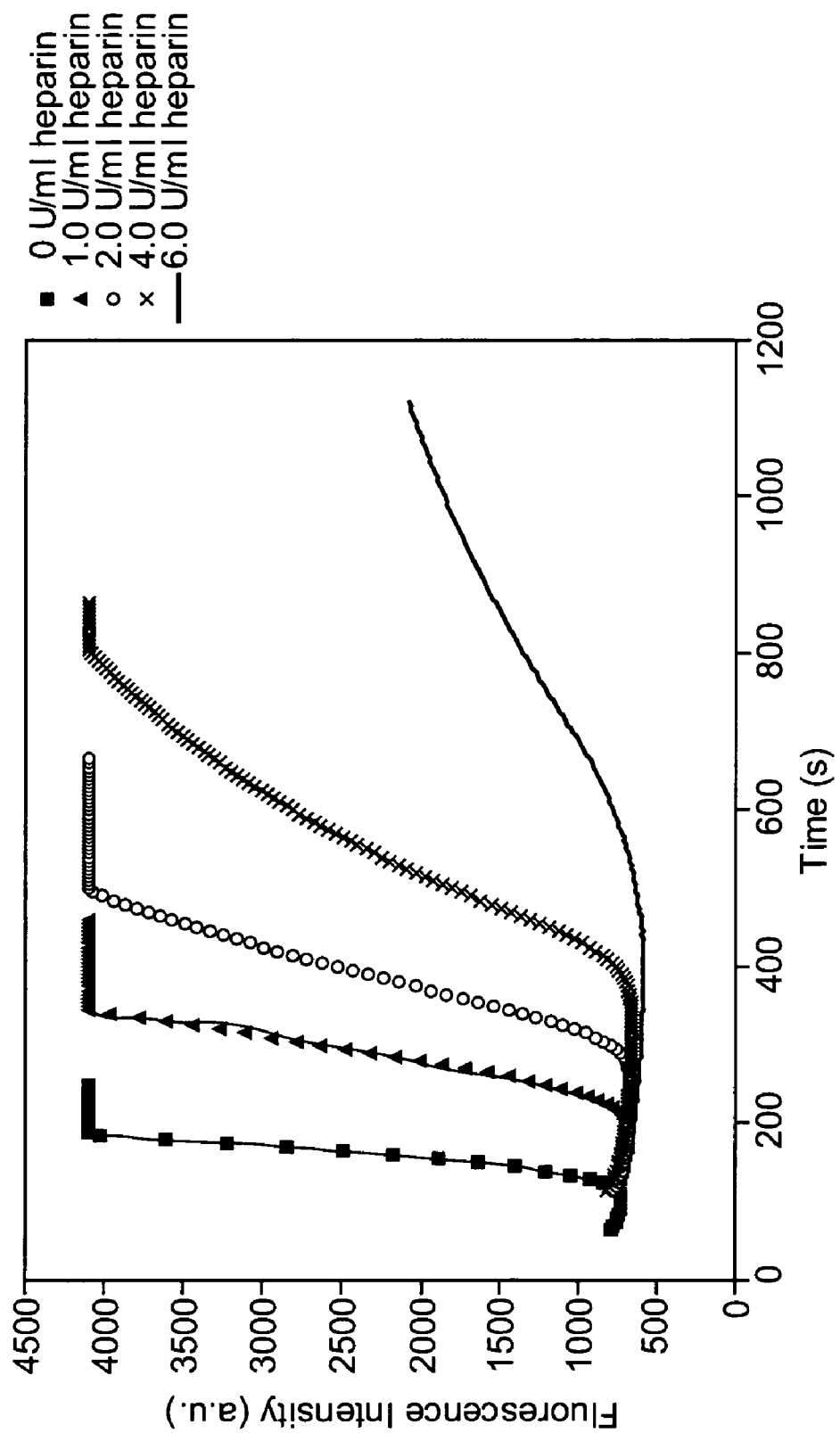
FIG. 15 is a graph of fluorescence versus time for samples of fresh whole blood at various heparin levels for strips made from a BTS-25 membrane.
Figure 33:
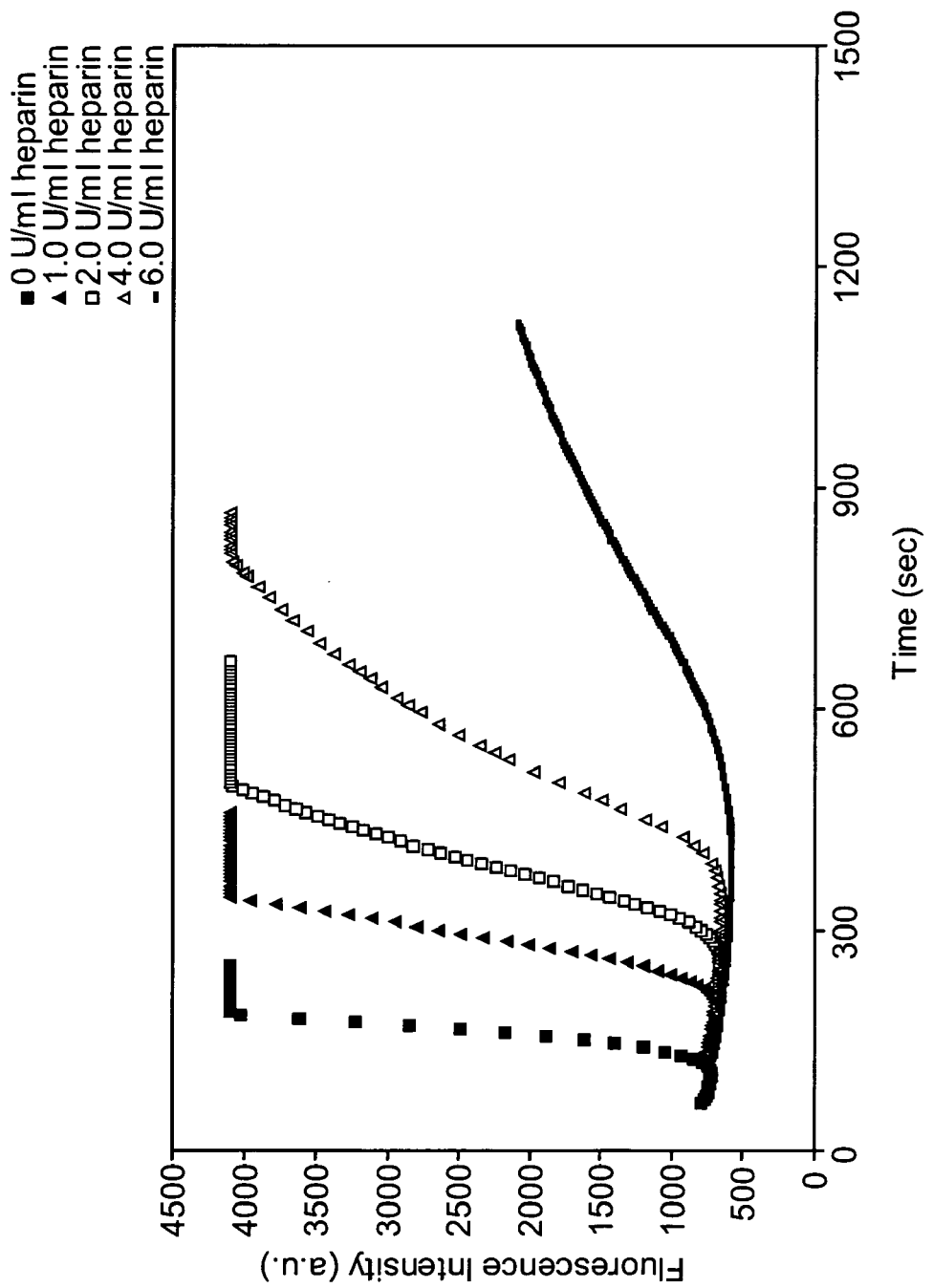
FIG. 33 is a graph of fluorescence intensity versus time for samples of fresh whole blood at various heparin levels.

Because this invention detects generation of a component of the coagulation cascade, such as thrombin, it is not necessary to wait for the coagulation process to reach completion by forming a clot. Furthermore, formation of thrombin, as shown by increasing signal such as fluorescence, follows an approximately linear increase versus time while levels are rising. As shown in FIGS. 7, 15 and 33, in an ACT test using a fluorogenic thrombin substrate, thrombin levels, as indicated by fluorescence, stay at baseline for a period of time, typically less than or equal to about 120 seconds, then rise in an approximately linear fashion until they approach an approximately maximum level, after which they plateau and little or no further increase occurs. The time to reach the maximum thrombin level increases with increasing amounts of heparin, but the slope of the increase is approximately constant throughout the period of the rise in fluorescence. Similar increasing signal patterns should be observed for quantifiable signals other than fluorescence as well. Applicants take advantage of the predictable linear increase in fluorescence to obtain coagulation tests results without waiting for fluorescence to reach the maximum level.

The coagulation test result is calculated from data obtained prior to the signal, such as fluorescence, reaching maximum intensity. In some embodiments of the invention, the time required for the fluorescence to increase a predetermined amount above the baseline fluorescence is monitored, and this time is used to derive a coagulation test result. After application of the blood sample to the first membrane area 10, the signal is monitored on the second membrane area 12 to determine a baseline signal value. The baseline signal may be obtained from one measurement taken at a certain point after the application of the sample. For example, the baseline signal may be the signal value twenty seconds after application of the sample. Alternatively, the baseline signal may be calculated by averaging more than one signal measurement. For example, the signal value may be measured every 5 seconds after application of the sample to the membrane 2. The first particular number of measurements, for example the first ten measurements, may be averaged and the average is taken as the baseline signal. Different numbers of measurements may be taken to derive the average. Furthermore, the first measurement, or the first certain number of measurements, may be disregarded. For example, the second through the eleventh measurement may be averaged to obtain the baseline. The choice of which measurements to use for determining the signal baseline will depend upon details of the strip 14 as well as the machine used to detect the signal. In a preferred embodiment the signal is fluorescence and the baseline fluorescence intensity, also referred to as fluorescence, is an average of the first ten measurements which are taken every ten seconds.

After application of the sample, the signal may be monitored at fixed time intervals, such as every five seconds or every ten seconds. Alternatively, the time interval between signal measurements may vary. The time intervals may vary, for example, such that there is a greater interval between measurements at low signal values, and a shorter interval between measurements (for more frequent measurements) once the signal rises above a certain level or after a certain period of time. Alternatively the signal may be continuously monitored during a portion of or during all of the monitoring process.

In one aspect of the invention, the signal is monitored until it increases to a particular amount, which is the end point of the test. For example, in the case of a fluorescent signal, the particular end point fluorescence value could be a predetermined level of fluorescence, such as 750 a.u. (arbitrary units) for all samples. Alternatively, the value could be adjustable based on the baseline. Thus, for a baseline fluorescence falling in a particular range, the end point fluorescence might be one value. The end point value could be stepwise higher or lower for correspondingly higher or lower values of baseline fluorescence.

Alternatively, the end point signal could be calculated based on the baseline signal. According to such embodiments, the end point would be reached when the signal value had increased by an amount approximately equal to a predetermined percent of the baseline signal. When the signal is fluorescence, this percent is preferably between approximately 25% and approximately 100%. In some embodiments of the invention, the end point is reached when the fluorescence intensity increases by an amount equal to approximately 50% of the baseline fluorescence intensity.

In embodiments of this invention in which the substrate is a fluorophore, the amount of increase in fluorescence of a particular measured data point above the baseline fluorescence is the fluorescence ratio. The fluorescence ratio represents the amount of the increase in fluorescence as a percent of the baseline fluorescence for a particular fluorescence measurement, and is calculated using the following formula:

$$\text{Fluorescence ratio} = \frac{(\text{fluorescence intensity}_{data\ point} - \text{fluorescence intensity}_{baseline})}{\text{fluorescence intensity}_{baseline}} \times 100\%$$

In some embodiments of this invention, an appropriate fluorescence ratio, for example 50%, is selected as the end point of the experiment. The time required for the fluorescence intensity to rise to a level approximately equal to the predetermined fluorescence ratio is taken as the result. Alternatively, this time may be used to derive a coagulation test result such that the result is comparable to the results obtained by other testing methods. By obtaining a result in this way, the result may be obtained long before clot formation occurs or before thrombin generation has reached a maximum.

The use of the fluorescence ratio does not result in skewing of the plot of fluorescence versus time. Alternative methods that use the maximum fluorescence to normalize the fluorescence measurements can obtain skewed results. One method of calculating normalized fluorescence known in the prior art uses the following equation:

$$\text{Fluorescence} = \frac{F_t - F_{min}}{F_{max} - F_{min}} \times 100\%$$

where $F_t$ is the fluorescence intensity at a given time point, $F_{min}$ is the minimum fluorescence intensity, and $F_{max}$ is the maximum fluorescence intensity for a particular sample. Alternatively, fluorescence values at particular times may be taken as representative of the $F_{max}$ and $F_{min}$.

The calculation of the coagulation test result according to embodiments of the invention may be performed by a machine such as a computer or processor. The instructions for causing the machine to execute the calculation of the test result may be in the form of a computer readable medium.

The following is intended to illustrate but not limit the invention:

EXPERIMENTAL

Except as otherwise indicated, the following components and procedures were used for all experiments.
Basic Buffer: The same basic buffer was used throughout the following experiments.
The basic buffer is 0.1M Hepes, pH 7.4, 10 mM $CaCl_2$, 20 mg/ml Sigma protease-free bovine serum albumin (BSA) and 50 mg/ml 87%-89% hydrolyzed polyvinyl alcohol (PVA). It was created by the following process: 23.83 g Hepes was dissolved in 800 mL deionized water. The pH was adjusted to 7.4 using 1N NaOH and then the solution was filled to 1L with deionized water. This solution was then used to dissolve the BSA and PVA. $CaCl_2$ was then added to give the final concentrations stated above.
Kaolin: Kaolin was obtained from two sources. HR-ACT kaolin, obtained from Medtronic HR-ACT cartridges (Charles B. Chrystal Co., Inc., New York, N.Y. 10007), was used for some examples. In other examples, dry ultrafine kaolin (Imerys, Roswell, Ga. 30076) was used.

In some examples, samples were premixed with kaolin (HR-ACT kaolin or ultrafine kaolin) before application of the sample to the strip. For mixing with HR-ACT kaolin, samples were loaded into one channel of the Medtronic HR-ACT cartridge. The cartridge was run in the Medtronic-ACT Plus instrument. For heparinized samples, the reaction was aborted after 100 seconds. For unheparinized samples the reaction was aborted after 50 seconds. 15 microliter samples were then removed from the cartridges and pipetted onto the strips for fluorescence testing. Use of the HR-ACT cartridge provided an efficient method of adding kaolin and mixing it with the samples. It also allowed for corresponding HR-ACT data to be collected.

In some examples, ultra fine kaolin or HR-ACT kaolin was coated onto the membranes using an airbrush or by rubbing. These techniques are described in the Examples below.

Heparin: Unfractionated heparin (100 Units/ml) was obtained from American Pharmaceutical Partner, Inc., Schaumburg, Ill. 60173.

Antithrombin III: Human Antithrombin III was obtained from DiaPharma Group, Inc., West Chester, Ohio 45069 as part of the Spectrolyse Anti-IIa kit. The ATIII reagent was reconstituted using amounts indicated in the test insert, except that basic buffer was substituted for dI water. Human Antithrombin II can also obtain from Grifols (Instituto Grifols, S. A., Barcelona, Spain). Recombinant ATIII can be obtained from GTC Biopharmaceuticals, Inc. Framingham, Mass. 01701

Substrate: (Tos-Gly-Pro-Arg)$_2$-Rhodamine 110 (Molecular Probe, Inc., Eugene, Oreg. 97402) was used as the substrate. In all examples except Examples 10 and 11, the substrate solution was obtained by adding (Tos-Gly-Pro-Arg)$_2$-Rhodamine-110 to basic buffer to produce a substrate having a concentration of 0.2 mM.

Membranes: Membranes were obtained from Pall Life Sciences (Ann Arbor, Mich. 48103).

Membrane Preparation: The membranes were coated with substrate either by dipping or by pipetting.
  Dipping: The substrate solution was added to a weigh boat. The amount of substrate solution added to the weigh boat depended upon the size of the membrane to be coated. The membrane was placed with the side to be coated down in the weigh boat and allowed to sit for about 15 seconds. The membranes were then removed from the substrate solution with a tweezers and excess substrate was removed by brushing the membrane against the side of the weigh boat. The process was repeated for the other side of the membrane in examples where both sides were coated.
  Pipetting: The membrane was placed in an empty weigh boat with the side to be coated facing up. The substrate solution was pipetted onto the top of the membrane as evenly as possible. The amount of substrate applied depended upon the size of the membrane. A small paint brush was used to brush the solution onto the membrane as evenly as possible. The process was repeated for the other side of the membrane in examples where both sides were coated.
  After coating with substrate, the membranes were dried, either at room temperature or in an oven or both.

Strip Preparation: After the membranes were coated with substrate and dried, they were cut into pieces measuring 1×2 cm. The membranes were assembled into strips using plastic sheets. The top sheet was produced by Beckman Coulter and is referred to by Beckman Coulter as a White Polystyrene (Beckman Coulter Inc., Brea, Calif. 92822). It included the following layers: 10 mm white polystyrene sheet, 4 mm 3M 415 adhesive, 2 mm 3M 815 red tape, 2 mm aluminum foil, and another 4 mm 3M 415 adhesive layer for adhering the strip to the top of the membrane. The bottom plastic sheet was a Clear Card which was also produced by Beckman Coulter and included the following layers: 4 mm 3M black tape, 10 mm clear polystyrene, and a 4 mm 3M 415 adhesive layer for adhering the sheet to the bottom of the membrane. The top sheet of plastic included a 2 mm round sample window and was applied to the top side of the membrane, with the window over the first membrane area, while the bottom sheet of plastic was clear and was applied to the membrane.

Meters: A prototype meter was obtained from Beckman Coulter (Carlsbad, Calif.), The meter included an optics module which provided a mechanical, electrical and optical interface with the test strip. The optics module included a light source, a photodetector, an optical filter, and sensors to detect the presence of a strip and a sample. The test strip was inserted into the optics module, which was then warmed to body temperature. The blood sample was then applied to the strip, and the application was sensed by the meter. A light source illuminated the strip and light was reradiated by the fluorophore cleaved from the substrate on the strip to be detected by the photodetector. An optical filter constrained the light entering the photodetector to a narrow wavelength range, encompassing the emission wavelength of the fluorophore. The meter recorded the fluorescence intensity of the light emitted by the fluorophore in a.u. (arbitrary units) every ten seconds.

Blood and Plasma samples: Samples of fresh whole blood were obtained from healthy donors and were drawn by venipuncture. Samples of plasma were obtained from the whole blood by removing the cellular components via centrifugation. 15 microliter samples were applied through the strip window onto the first membrane area.

Example 1

Fluorescence Detection with Rough Membrane Surface Receiving Sample

BTS-45 membranes were prepared by pipetting 4.5 ml of basic buffer and 0.5 ml of thrombin substrate at 2 mM, reconstituted 1:1 with isoproponol, onto the rough side of the membrane. Membranes were dried and assembled into strips with the rough side of the membrane providing the first membrane area for receiving sample.

Citrated whole blood was combined with unfractionated heparin to produce samples containing 0, 0.5, 1.0, 1.5 and 2.0 Units/ml heparin. Plasma was also combined with unfractionated heparin to produce samples with the same concentrations of heparin as the citrated whole blood.

0.4 ml of the citrated whole blood or the plasma samples at each heparin level were added into the cartridges and the samples were mixed with 0.1 ml of HR-ACT kaolin in HR-ACT cartridges by the ACT Plus instrument. 15 microliter of the mixed samples were taken out of the cartridge after 50 sec (for samples without heparin) or 100 sec (for samples with heparin) and applied to the strips. Fluorescence was read by the meter.

Figure 2:
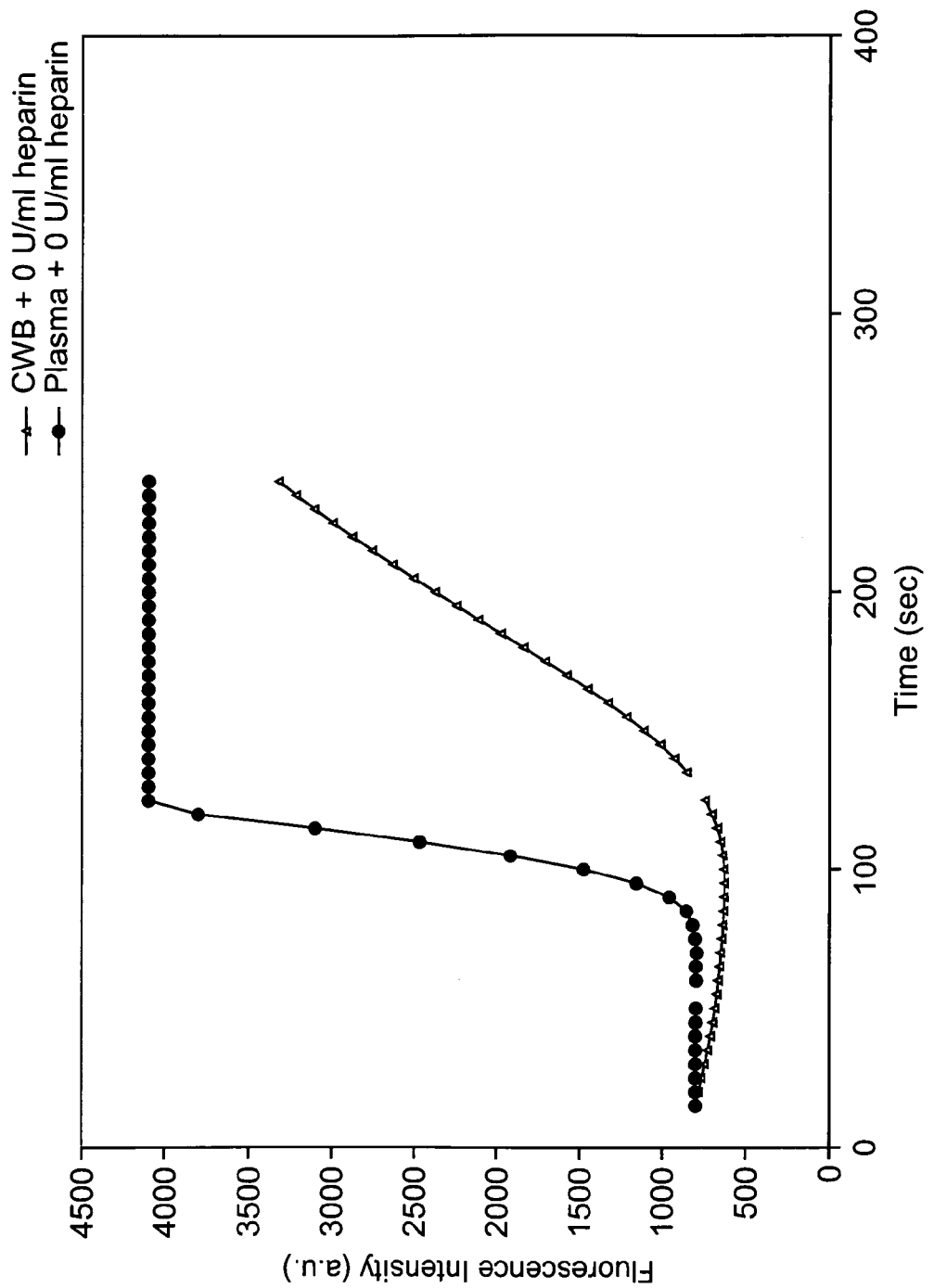
FIG. 2 is a graph of fluorescence versus time for samples of citrated whole blood and plasma without heparin in basic buffer with HR-ACT kaolin, and with the rough side of the membrane receiving the sample.
Figure 3:
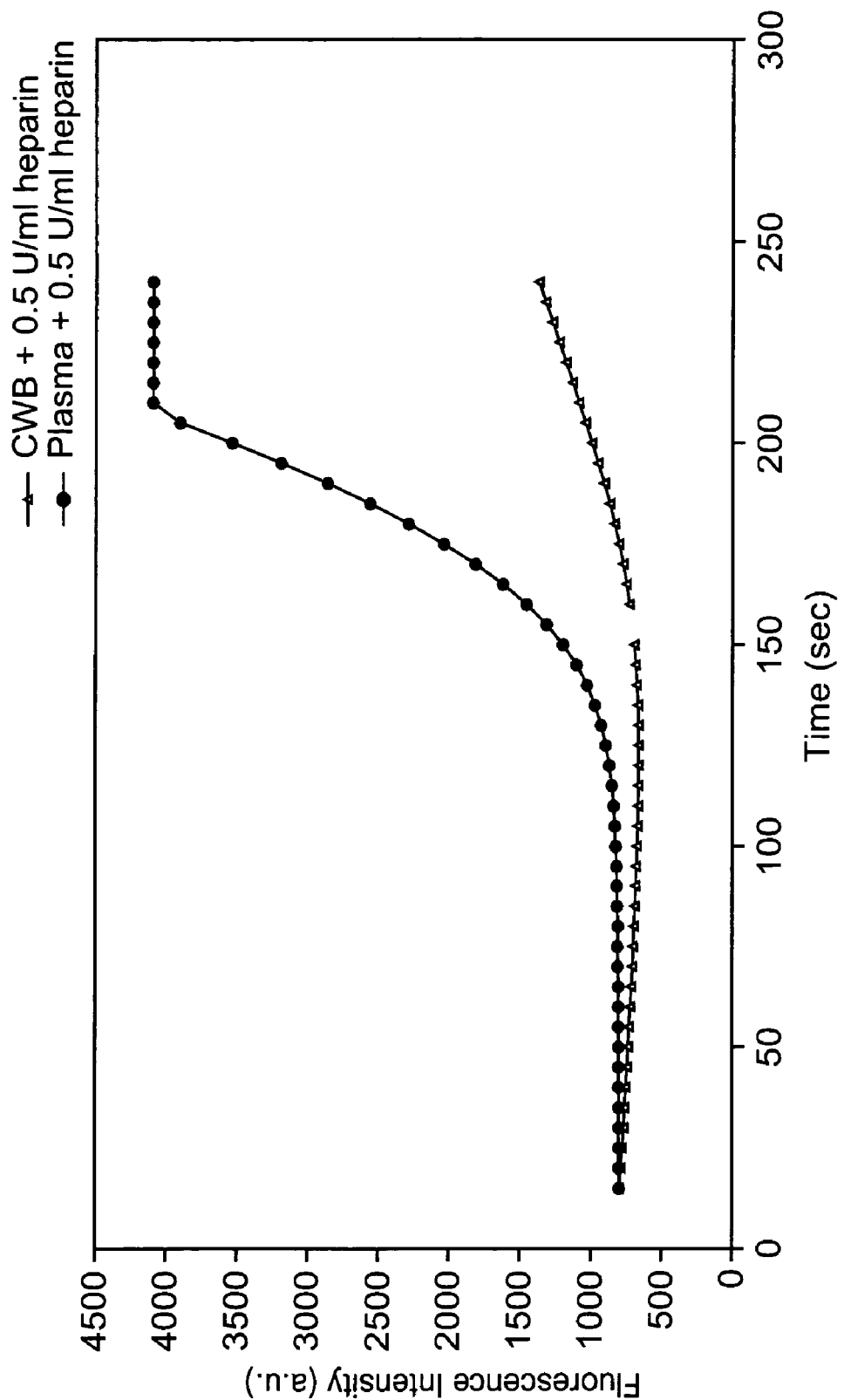
FIG. 3 is a graph of fluorescence versus time for samples of citrated whole blood and plasma with 0.5 U/ml heparin in basic buffer with HR-ACT kaolin.
Figure 4:
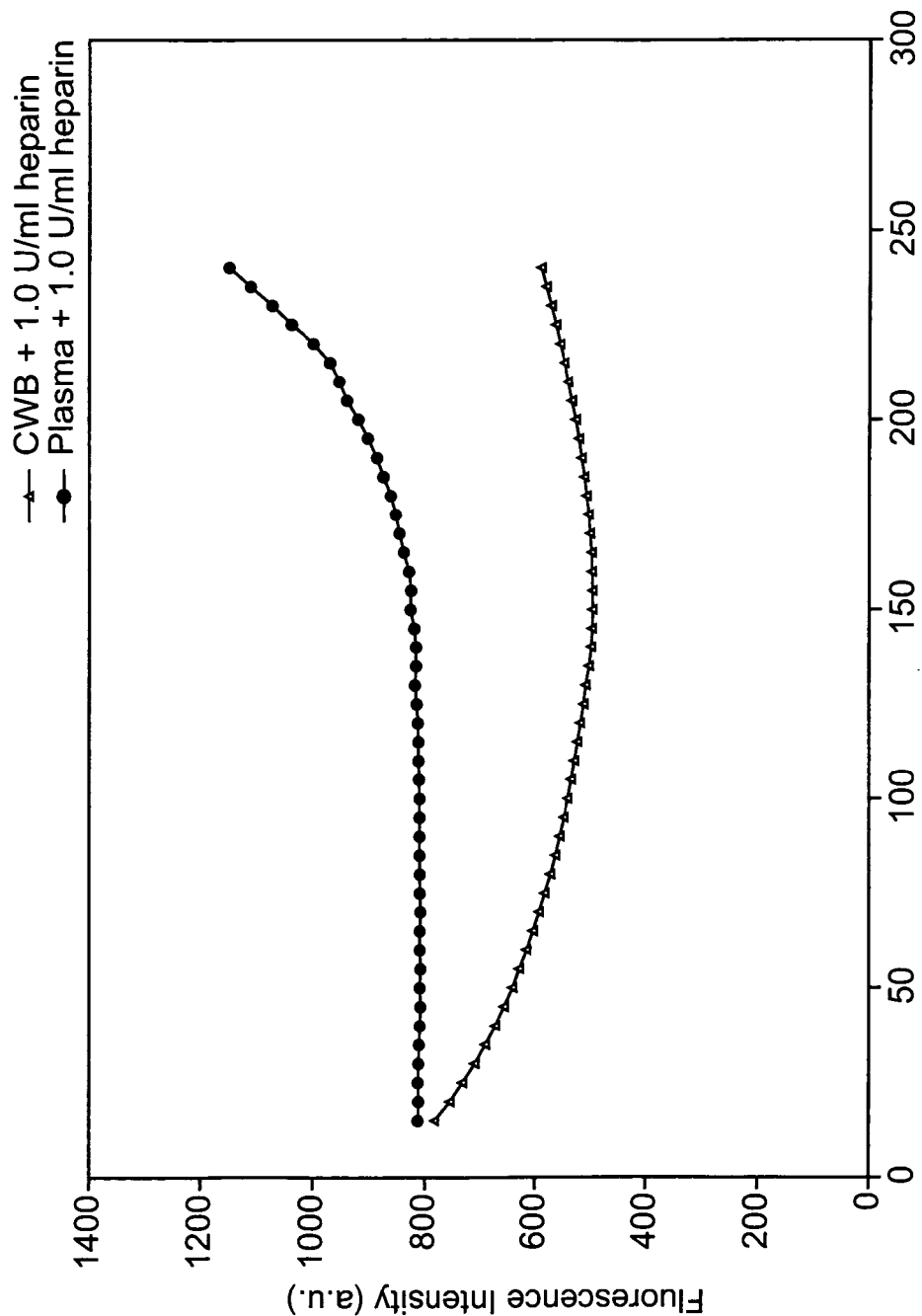
FIG. 4 is a graph of fluorescence versus time for samples of citrated whole blood and plasma with 1.0 U/ml heparin in basic buffer with HR-ACT kaolin.
Figure 5:
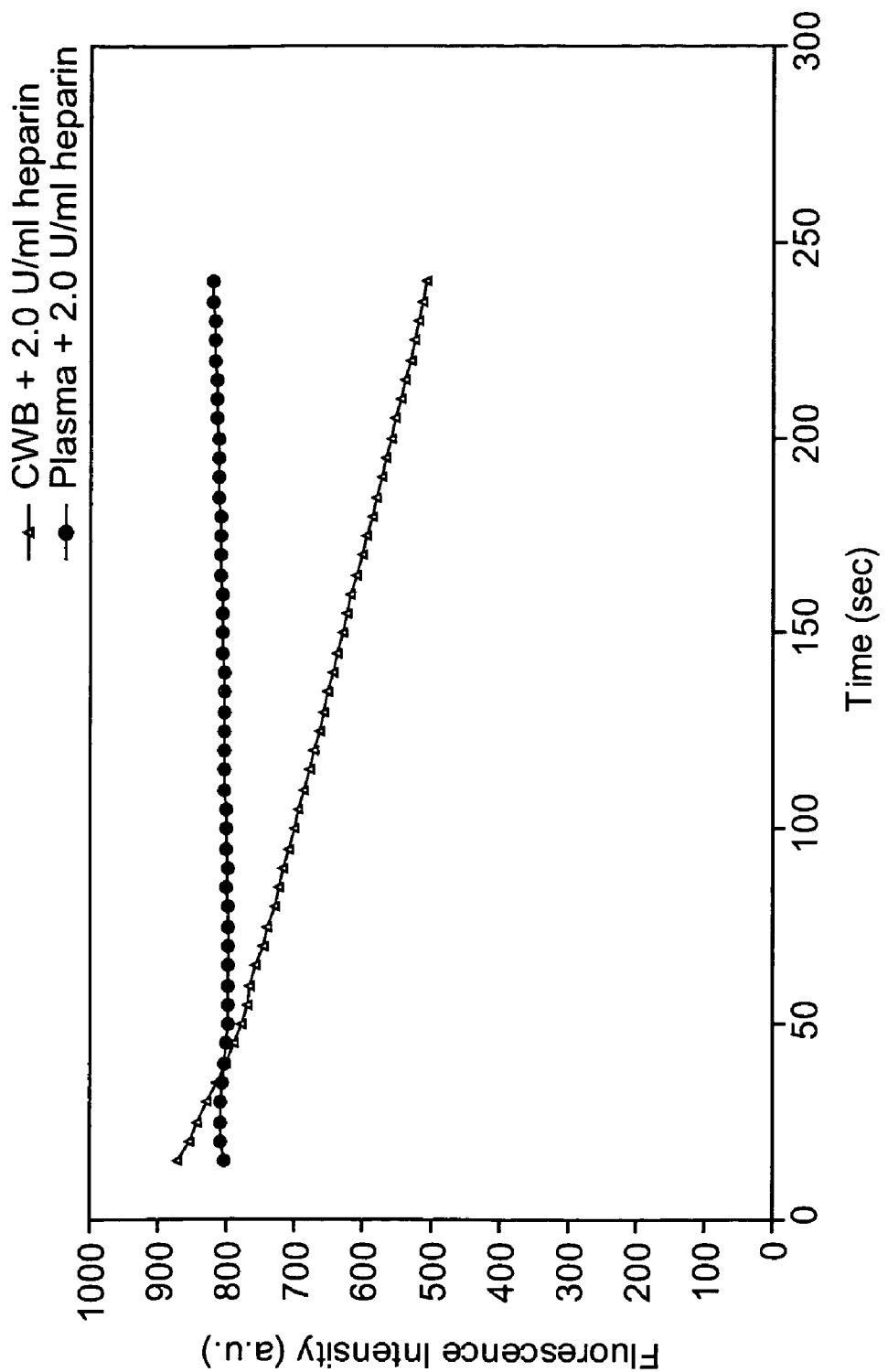
FIG. 5 is a graph of fluorescence versus time for samples of citrated whole blood and plasma with 2.0 U/ml heparin in basic buffer with HR-ACT kaolin.

Results are shown in FIGS. 2-5, which show graphs comparing the fluorescent signal generated by the samples of citrated whole blood compared with the fluorescent signal generated by the samples of plasma. FIG. 2 compares the samples with no heparin, while FIG. 3 compares the samples with 0.5 Units/ml of heparin. FIGS. 4 and 5 compare the samples after anticoagulation with 1.0 Units/ml and 2.0 Units/ml heparin, respectively.

In this experiment, the strips were made with the rough side of the membrane receiving the sample. The samples were mixed with kaolin, an intrinsic pathway activator, to generate fluorescence representative of an ACT. If the red blood cells did not interfere with signal detection, the whole blood would be expected to produce a faster fluorescence rise than plasma at each heparin level. This result would be expected due to the presence of platelets in whole blood which participate in the coagulation process. In contrast, the plasma samples lack platelets and would therefore be expected have a slower rise in fluorescence. However, in the samples with no heparin and 0.5 Units/ml heparin, the rise in fluorescence in the citrated whole blood sample was slower than in plasma. In the samples with 1 Unit and 2 Units/ml of heparin, the signal of the citrated whole blood sample fell below the baseline fluorescence. These results indicate that the fluorescent signal produced by the thrombin was being quenched in the whole blood sample in these strips. Furthermore, the results show that this effect is increased by the presence of higher levels of heparin.

Example 2

Fluorescence Detection with Smooth Membrane Surface Receiving Sample

BTS-25 membranes were coated with substrate solution on the rough side by the dipping method described above. After drying, the membranes were assembled into strips with the smooth side of the membrane up to receive the sample.

Fresh whole blood (FWB) was combined with unfractionated heparin (100 Units/ml) to produce samples containing 0, 1.0, 2.0, 4.0 and 6.0 Units/ml heparin. Plasma was combined with unfractionated heparin (100 Units/ml) to produce plasma samples containing 0, 1.0, 2.0, 4.0 and 6.0 Units/ml heparin. The fresh whole blood and the plasma samples were combined with kaolin using HR-ACT cartridges as described above.

Figure 6:
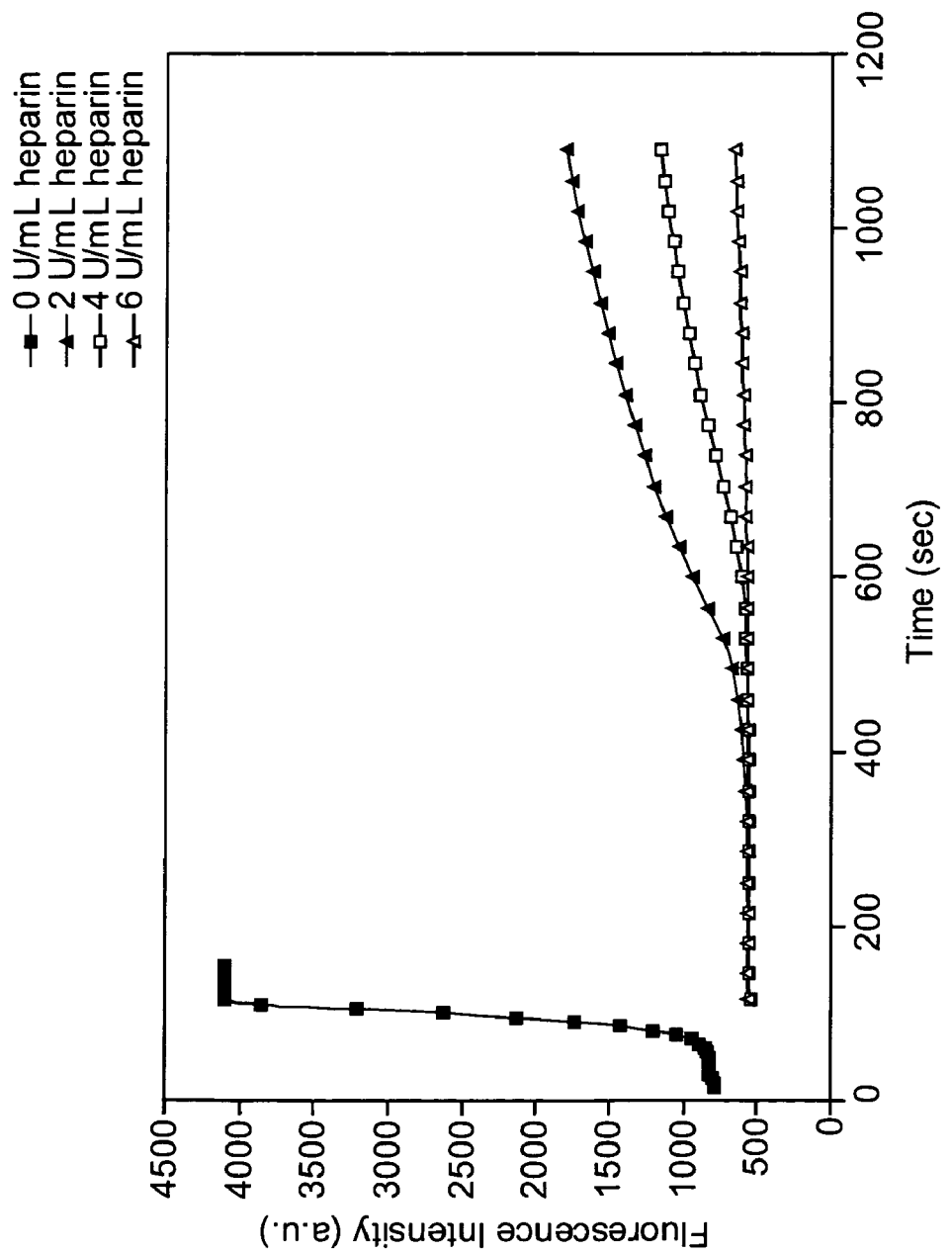
FIG. 6 is a graph of fluorescence versus time for samples of plasma at various heparin levels in basic buffer with the smooth side of the membrane receiving the samples.

The prepared samples were applied to the strips on the smooth surface by pipetting 15 microliters of sample onto the first membrane area and fluorescence results were read. Results of fluorescence versus time for the plasma samples are shown in FIG. 6. The results for fluorescence versus time for the blood samples are shown in FIG. 7. For each graph, the different lines represent the samples containing different amounts of heparin. While the fresh whole blood samples of FIG. 7 show rising fluorescence and separation of the lines at every heparin level, the plasma samples of FIG. 6 only show a good rise in fluorescence for the 0 and 1.0 Unit/ml heparin samples. The plasma samples with higher heparin levels showed little or no increase in fluorescence. Plasma differs from whole blood in that it lacks platelets. This comparison demonstrates that platelet participation in the production of thrombin is important, particularly at higher heparin levels.

FIGS. 6 and 7 show the results when the membrane orientation is reversed such that the fresh whole blood and the plasma samples were applied to the smooth surface of the membrane. In comparison, FIGS. 2-5 show the results of Example 1 in which the samples were applied to the rough side of the membranes in the method of the prior art. When applicants reversed the membrane orientation such that the smooth side received the sample, the signal generation was greatly improved. In both FIGS. 6 and 7, the rise in fluorescence was delayed in the samples containing heparin, as is expected and desired for a coagulation test result.

Example 3

Effect of Pore Size on Fluorescence Detection

The following membranes, with the pore size ratings indicated in the chart were used for testing:

| Membrane | Pore Size rating (micrometer) |
|---|---|
| BTS-25 | 0.6 |
| BTS-10 | 1.0 |
| MMM-1 | 1.0 |
| MMM-2 | 2.0 |

The substrate solution was coated onto the rough side of the membranes by dipping as described above. The membranes were then laid with the smooth size down to dry. After drying, they were assembled into strips with the smooth side of the membrane providing the sample application area.

Four sets of blood samples were prepared for each membrane type by the following procedure. Samples of 0, 0.05, 0.1, 0.2 and 0.3 ml of unfractionated heparin (100 U/ml) were combined with 5 mL fresh whole blood to give final sample values of 0, 1, 2, 4 and 6 U/ml heparin.

The sample were combined with kaolin using an HR-ACT cartridge as described above. 15 microliters of pre-mixed sample was then applied to each strip and the fluorescence results were read by the meter.

Figure 8:
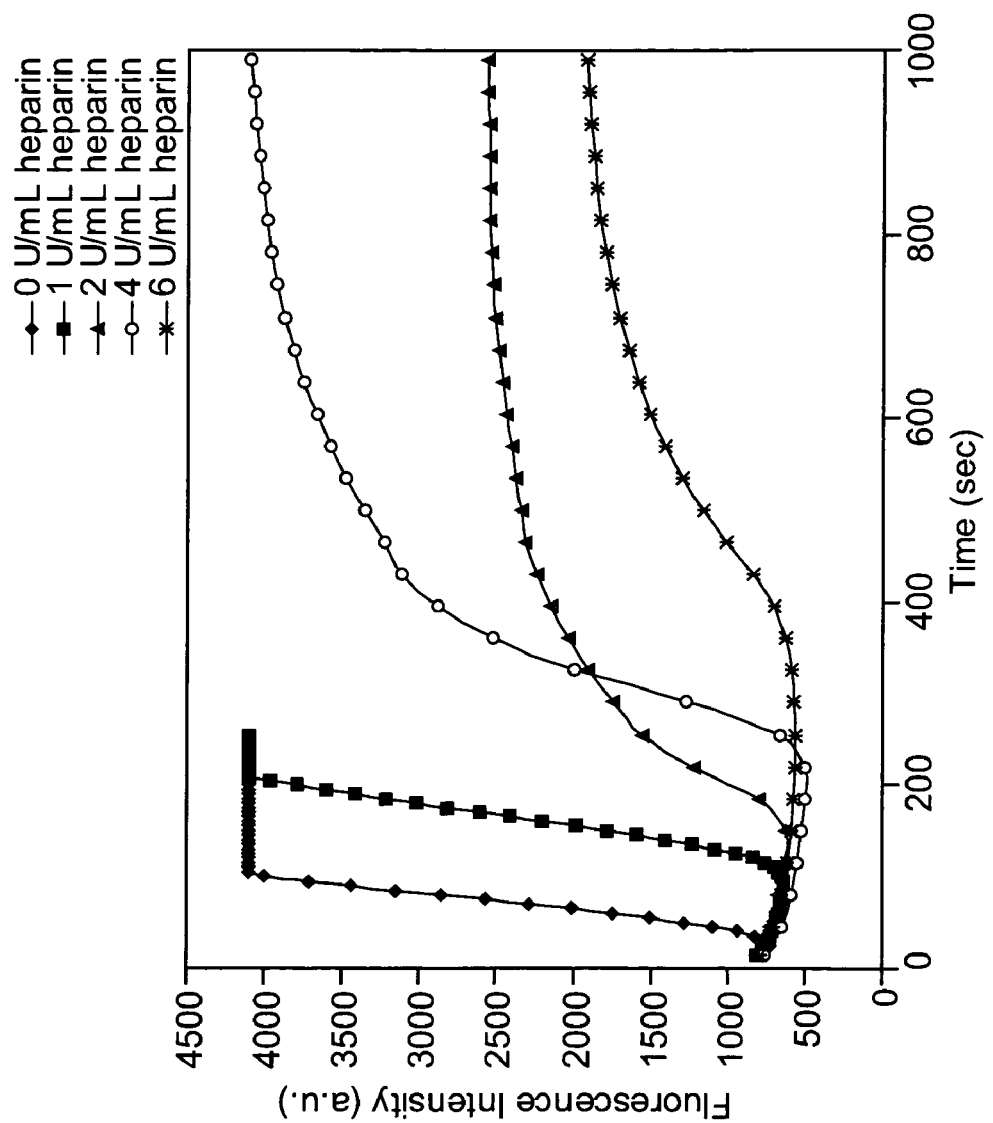
FIG. 8 is a graph of raw fluorescence versus time for samples of fresh whole blood at various heparin levels for strips made from a BTS-25 membrane.
Figure 9:
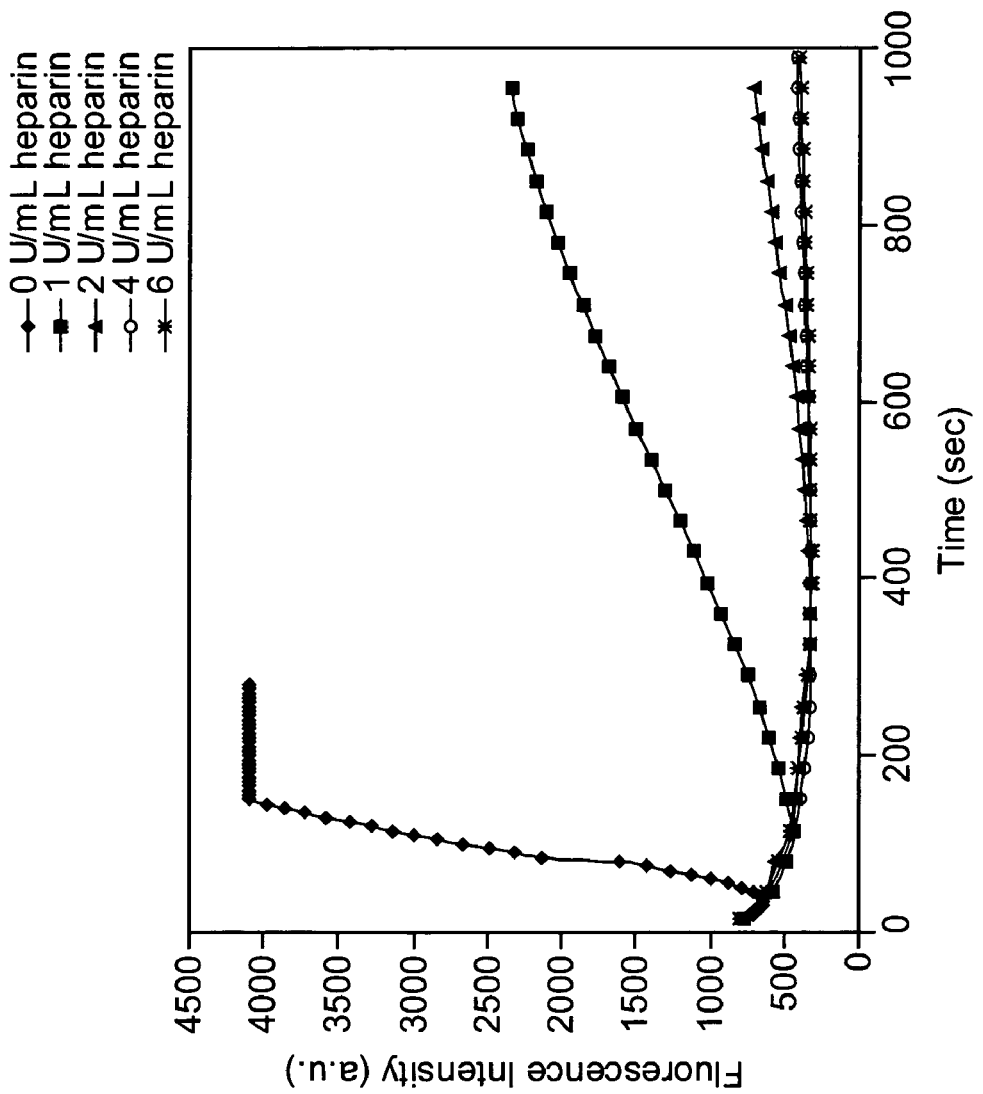
FIG. 9 is a graph of raw fluorescence versus time for samples of fresh whole blood at various heparin levels for strips made from a BTS-10 membrane.
Figure 10:
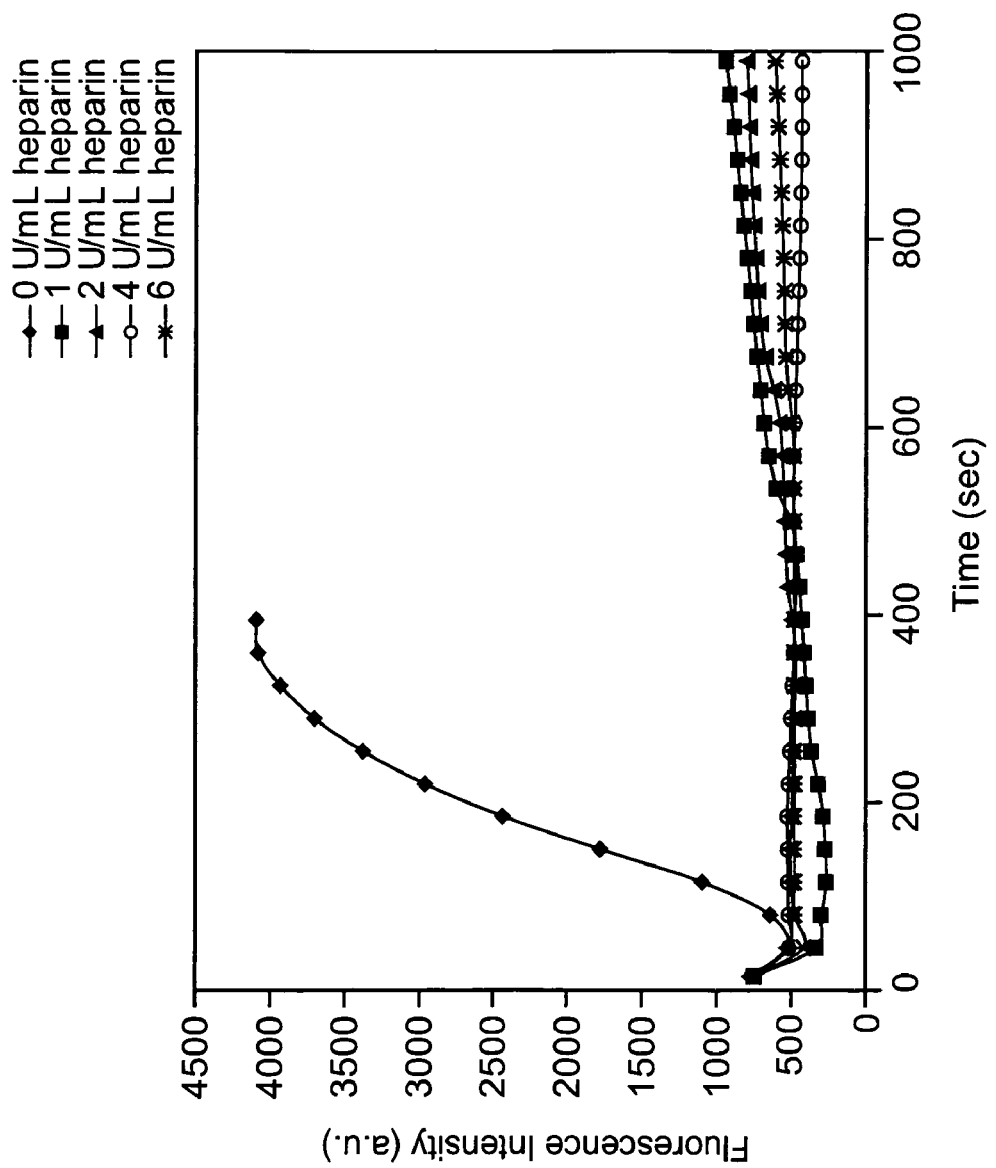
FIG. 10 is a graph of raw fluorescence versus time for samples of fresh whole blood at various heparin levels for strips made from a MMM1 membrane.
Figure 11:
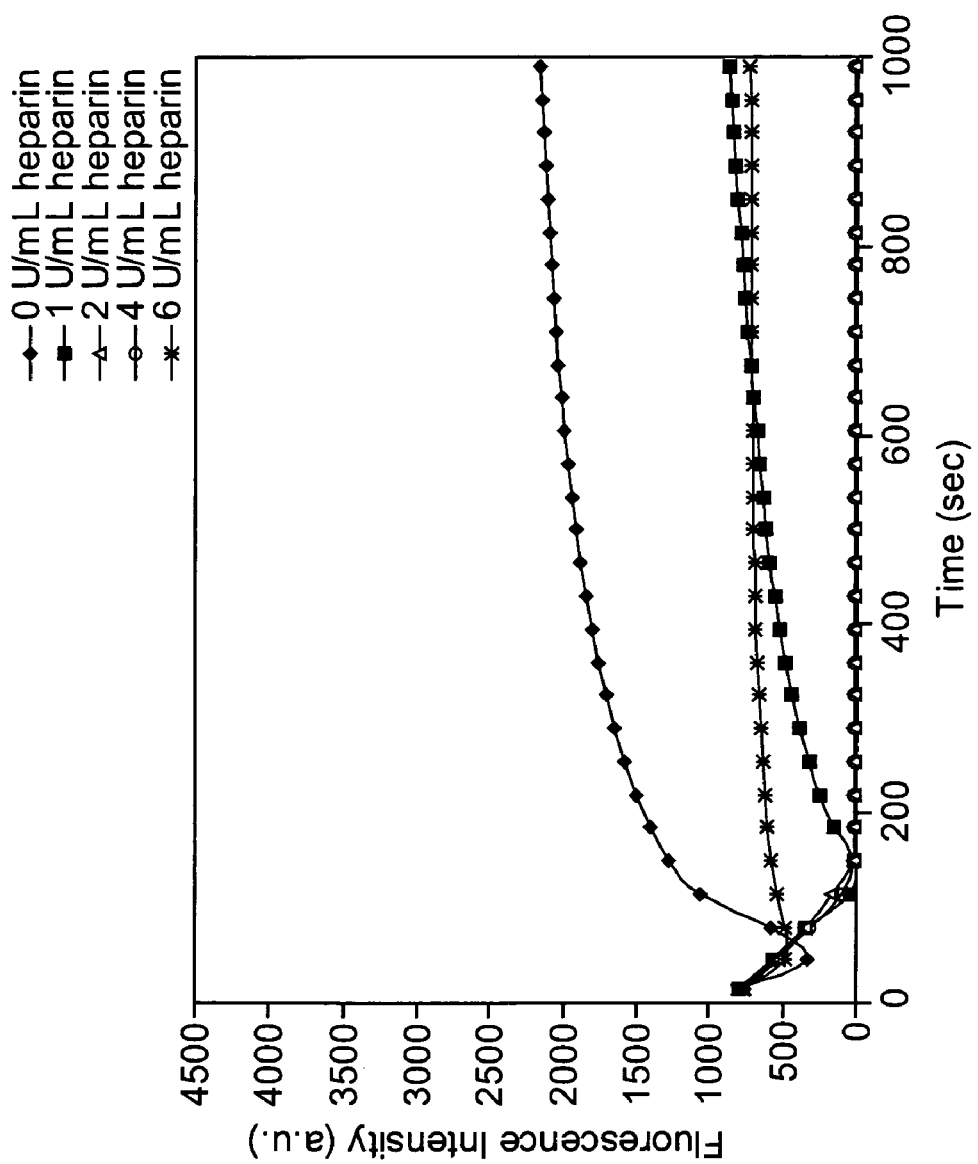
FIG. 11 is a graph of raw fluorescence versus time for samples of fresh whole blood at various heparin levels from strips made from a MMM2 membrane.

The results are shown in FIGS. 8-13 as fluorescence versus time for samples with different amounts of heparin. FIGS. 8-11 show the results for the four different types of membranes. As shown in FIG. 8, only the BTS-25 strip, with a pore size rating of 0.6 micrometer, produced distinct lines with rising fluorescence for each heparin level. Since distinct lines of rising fluorescence are necessary to obtain an ACT result, this membrane is superior. The membrane with the largest pores, MMM2 shown in FIG. 11, had the poorest results, with falling fluorescence, particularly at high heparin levels, due to quenching of the fluorescent signal.

Figure 12:
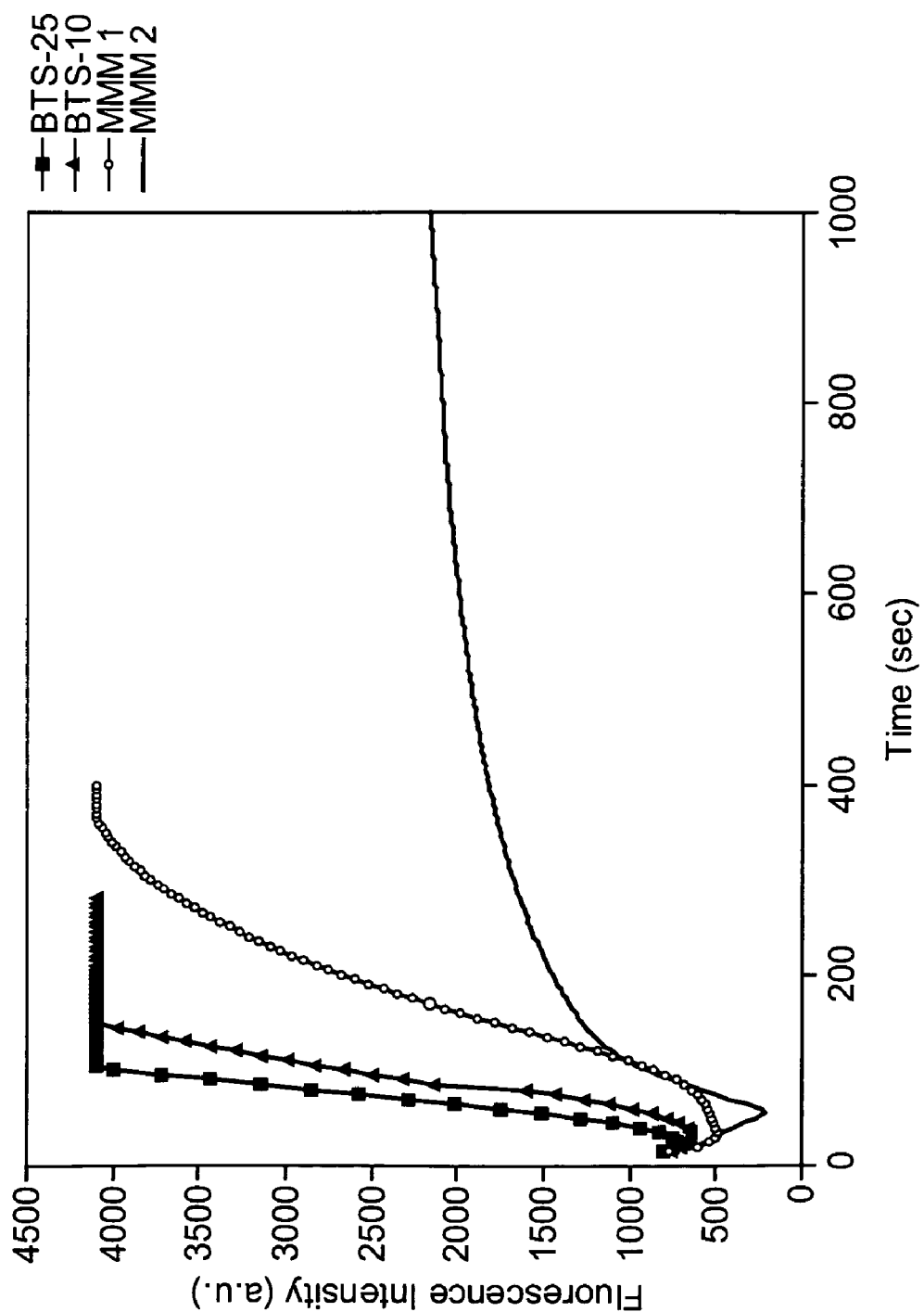
FIG. 12 is a graph of fluorescence signal versus time for sample of fresh whole blood containing no heparin for strips made from various membranes.
Figure 13:
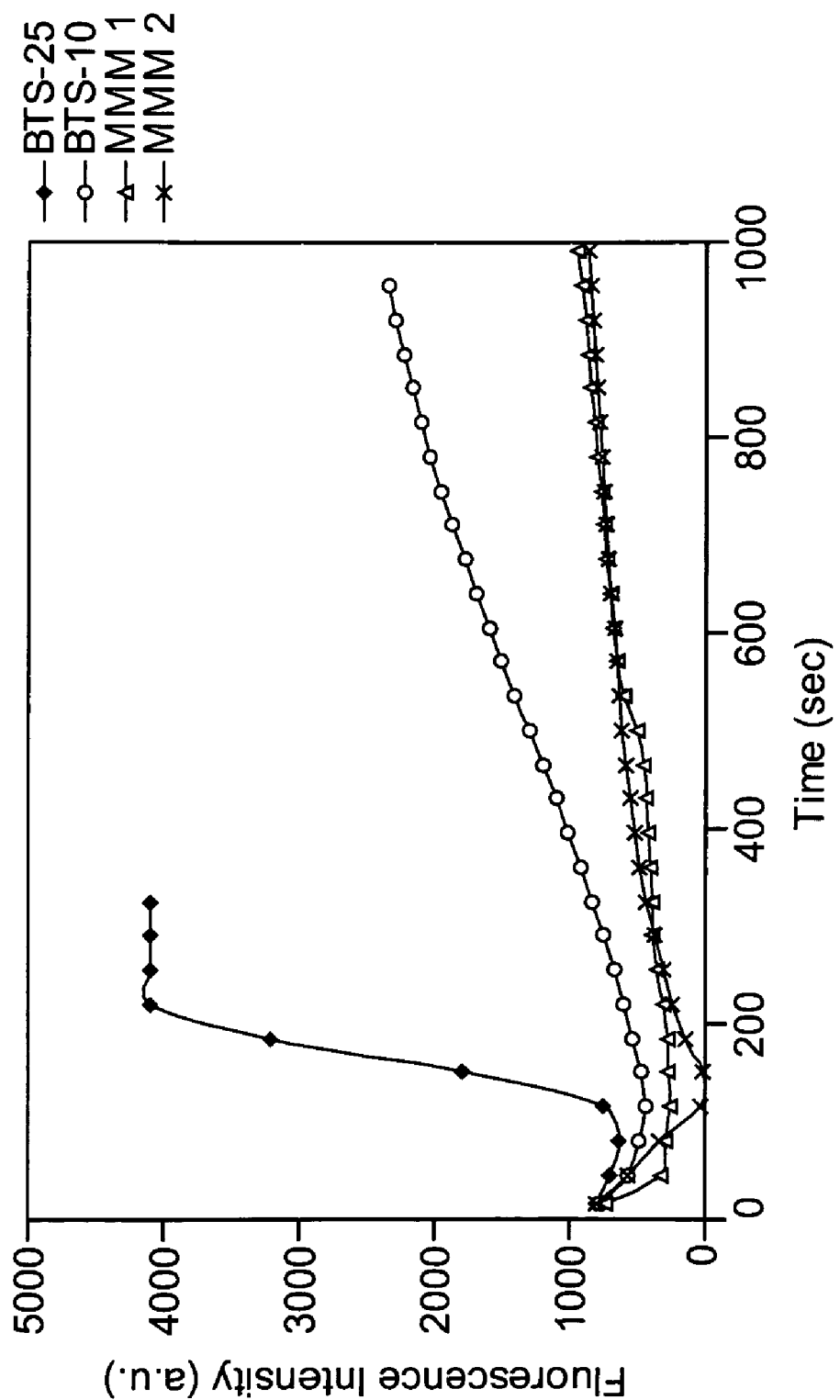
FIG. 13 is a graph of fluorescence signal versus time for samples of fresh whole blood containing 1 Unit/ml heparin for strips made from various membranes.

A comparison of FIGS. 12 and 13 shows that, while some membranes provided good results for samples with no heparin, the BTS-25 provided the best results among these membranes, for the heparinized samples.

Example 4

Effect of Pore Size on Fluorescence Detection for Testing with Pre-Mixed Kaolin

Strips were prepared using the following membranes:

| Membrane | Pore Size rating (micrometer) |
|---|---|
| BTS-45 | 0.45 |
| BTS-25 | 0.6 |
| BTS-10 | 1.0 |

The substrate solution was coated on the rough side of the membranes by dipping as described above. The membranes were removed with a tweezers and the excess solution was allowed to drip off. The membranes were then laid with the smooth size down to dry. After drying, the membranes were assembled into strips with the smooth side of the membrane providing the sample application area.

Four sets of blood samples were prepared for each membrane by the following procedure. Samples of 0, 0.05, 0.1, 0.2 and 0.3 ml of unfractionated heparin (100 U/ml) were combined with 5 ml fresh whole blood to give final sample values of 0, 1, 2, 4 and 6 U/ml heparin. Samples were combined with kaolin using the HR-ACT cartridge as described above. After mixing with kaolin, the samples were applied to the strips and fluorescence results were read with the meter.

Figure 14:
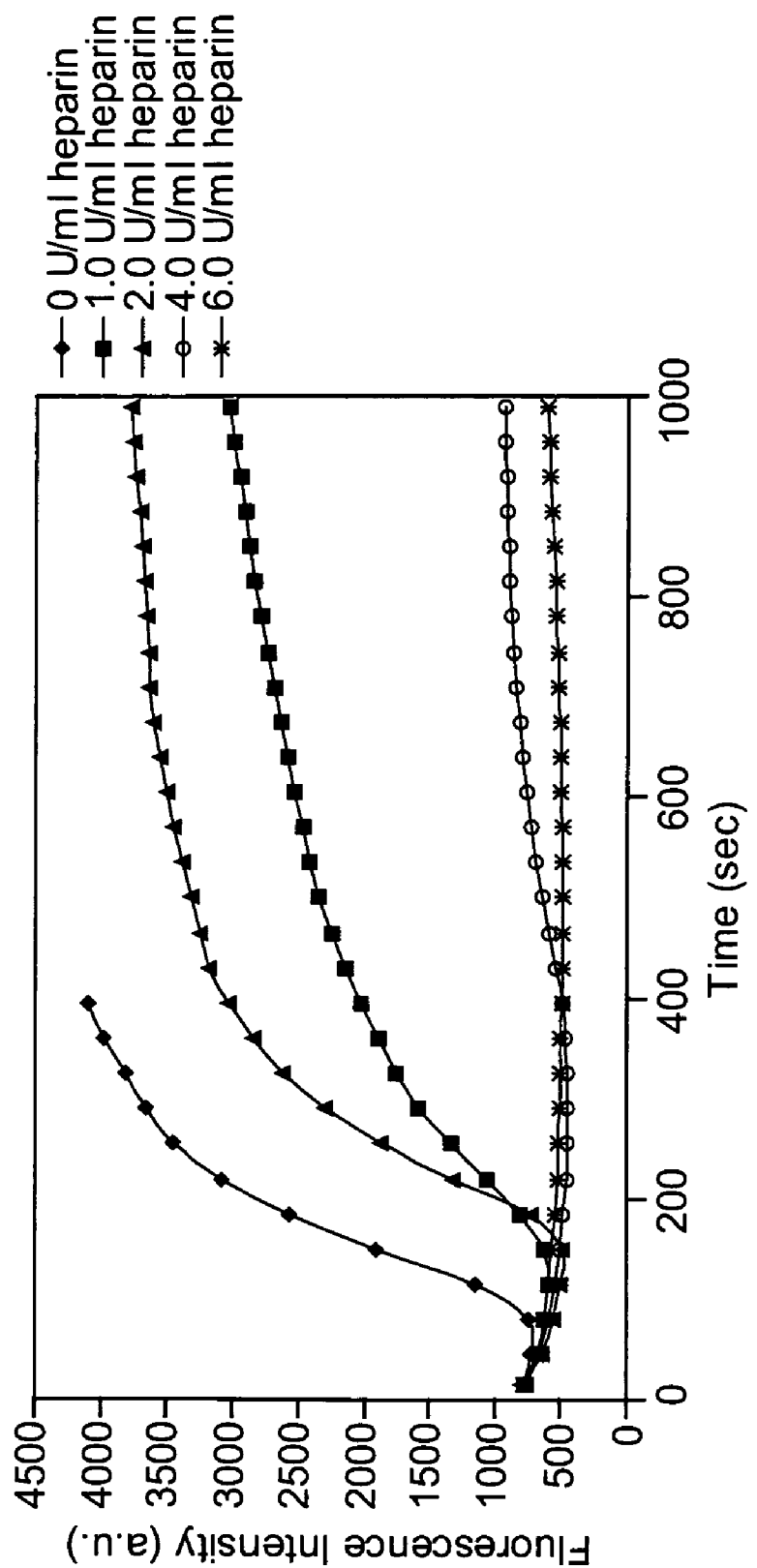
FIG. 14 is a graph of fluorescence versus time for samples of fresh whole blood at various heparin levels for a strips made from a BTS-10 membrane.
Figure 16:
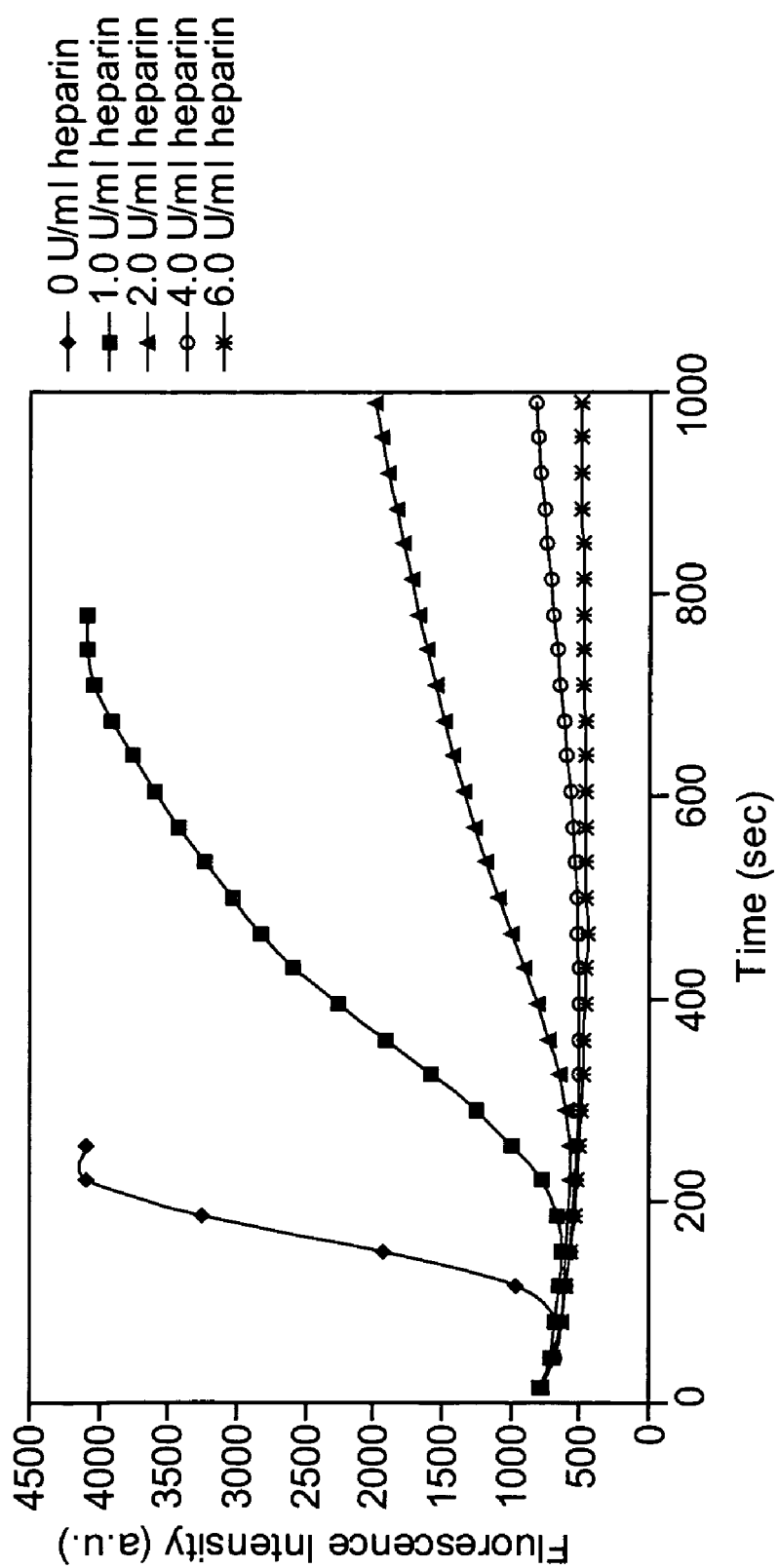
FIG. 16 is a graph of fluorescence versus time for samples of fresh whole blood at various heparin levels for strips made from a BTS-45 membrane.

The results are shown in FIGS. 14-16 as fluorescence versus time for samples with different amounts of heparin. FIGS. 14-16 show the results for the three different types of membranes. As shown in FIG. 15, only the BTS-25 strip, with a pore size rating of 0.6 micrometer, produced distinct lines with rising fluorescence for each heparin level. Since distinct lines of rising fluorescence are necessary to obtain an ACT result, this membrane is superior, among the membranes tested, for ACT testing. The membranes with the 0.45 micrometer pore size rating (BTS-45, FIG. 16) and with the 0.1 pore size rating (BTS-10, FIG. 14) showed rising fluorescence at lower heparin values and separation between the lines for different heparin levels, but the rise in fluorescence at high heparin levels was slow.

Example 5

Effect of Pore Size on Fluorescence Detection for Strips Made with Dry Kaolin

Strips were prepared using the following membranes:

| Membrane | Pore Size rating (micrometer) |
|---|---|
| BTS-80 | 0.05 |
| BTS-55 | 0.2 |
| BTS-25 | 0.6 |

The substrate solution was coated on the both sides of the membranes by dipping as described above. The membranes were removed with a tweezers and the excess solution was allowed to drip off. The membranes were then laid with the smooth side down to dry. After drying, the membranes were assembled into strips with the smooth side of the membrane providing the sample application area. A 12% suspension of ultrafine kaolin, stirred constantly prior to aerosolization, was applied as a single one second spray to the sample application area through the strip window using an airbrush (Badger Deluxe Model 200, bottom feed, single action, internal mix, from Badger Air-brush Co., Franklin, Ill. 60131) at 10 psi. Strips were dried.

Two sets of whole blood samples were prepared with heparin concentrations of 1 and 2 Units/ml. Samples of 15 microliters were applied to the strips and fluorescence was measured using the meter.

Figure 17:
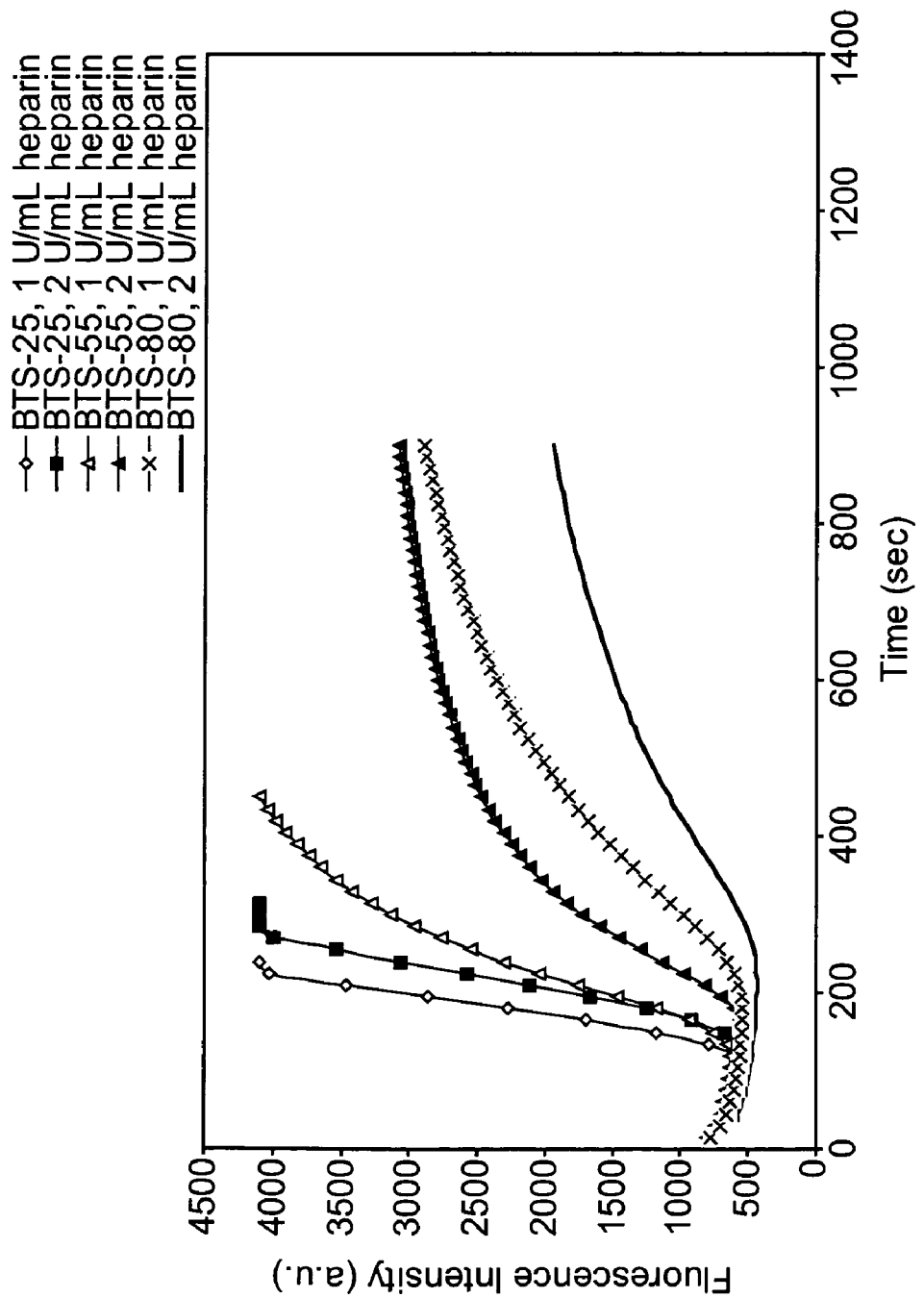
FIG. 17 is a graph depicting the membrane pore size effect on heparin resolution. Fluorescence was plotted versus time for samples of fresh whole blood containing 1 or 2 Unit/ml heparin for strips made from BTS-25, 55 and 80 membranes. 0.25 mL of 0.2 mM substrate peptide was applied to both sides of 5×2.5 cm membranes, and 12.0% ultrafine kaolin (UFK) was applied to the smooth side of the membrane.

The results are shown in FIG. 17 as fluorescence versus time for samples with different amounts of heparin. The BTS-80 and BTS-55, with smaller pore size ratings, gave the highest resolution but the slowest response. While not intending to be bound by theory, it is believed that the small pores slow the diffusion of the sample, allowing more time for heparin to catalyze the reaction between ATIII and thrombin and resulting in improved resolution between the heparin levels.

Example 6

Dry Kaolin Rubbed onto Membrane for ACT

BTS-25 membranes were coated with substrate on the rough side as described above. The coated membranes were dried in a 37° C. oven for 10 minutes, then air dried at room temperature.

Ultrafine kaolin was loaded onto the smooth side and the rough side of the membranes by rubbing 5.0 g, 1.6 g, or 0.8 g kaolin onto the membrane with fingertips as evenly as possible; excess was brushed off with a paintbrush. Membranes were weighed before and after kaolin loading. The membranes were cut and assembled into strips.

Samples of 0, 0.05, 0.1, 0.2 and 0.3 ml of unfractionated heparin (100 U/ml) were combined with 5.0 ml fresh whole blood to give final samples containing 0, 1, 2, 4 and 6 U/ml heparin.

Figure 18:
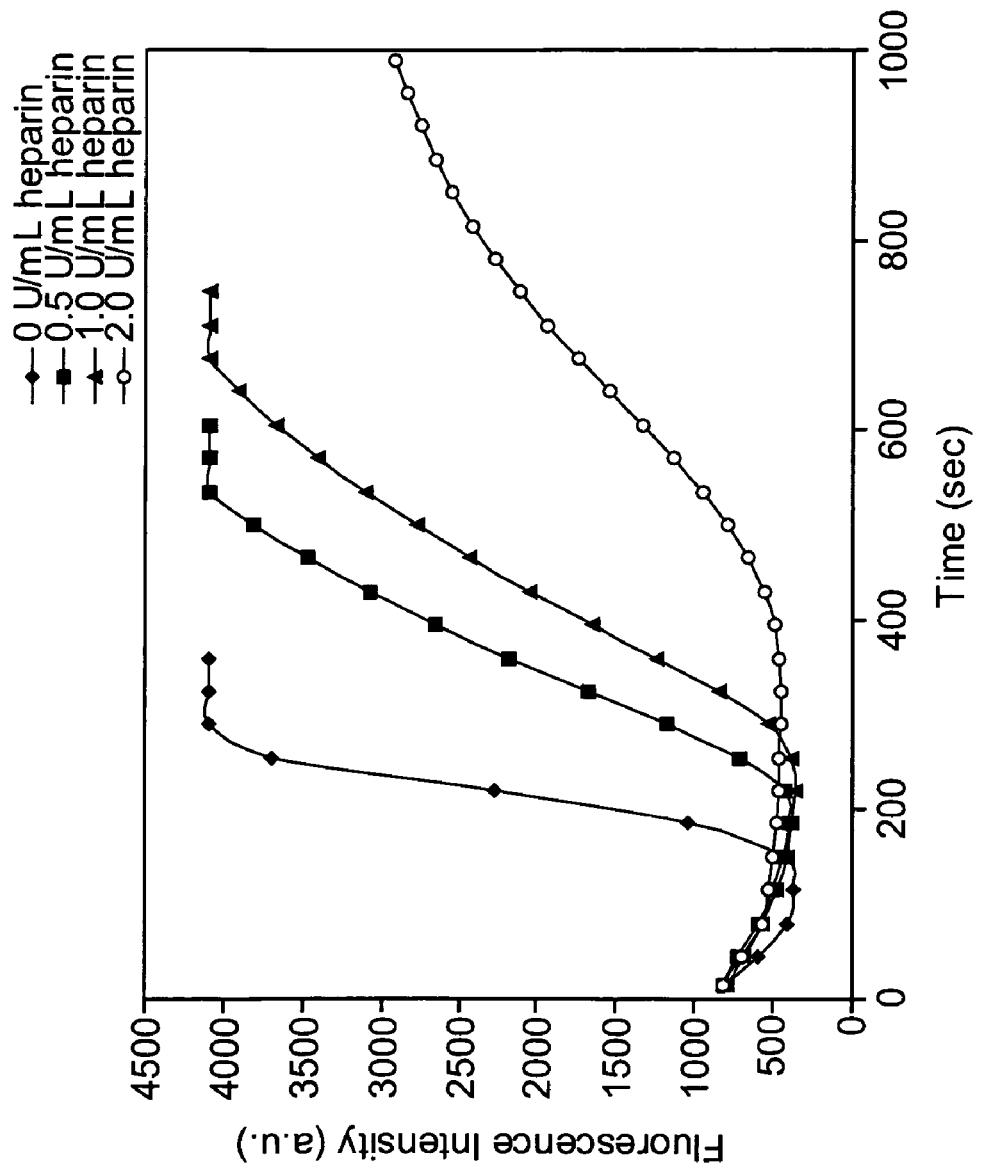
FIG. 18 is a graph of raw fluorescence versus time for samples of fresh whole blood at various heparin levels when dry kaolin is rubbed onto the membrane to increase its weight by 20%
Figure 19:
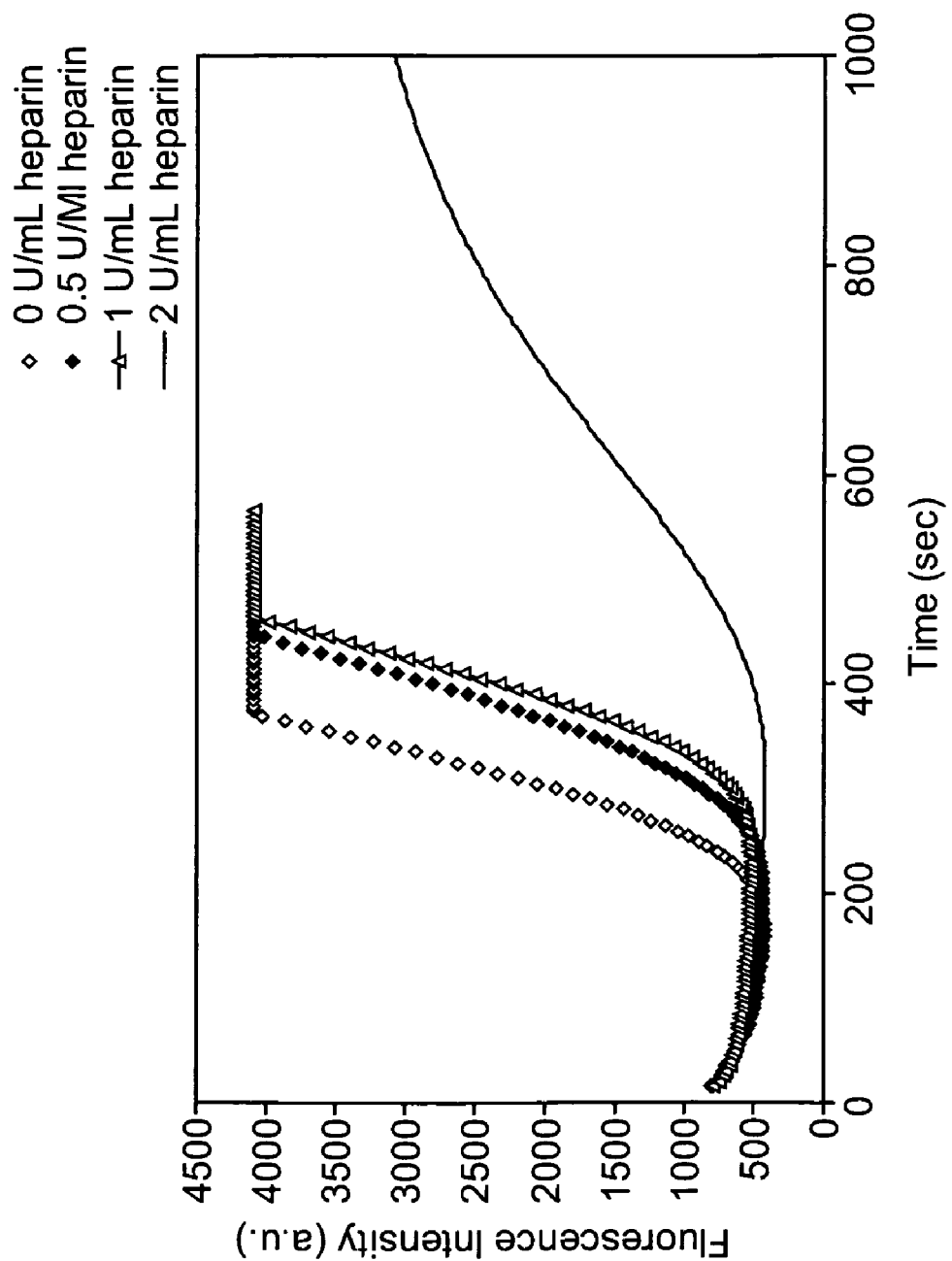
FIG. 19 is a graph of raw fluorescence versus time for samples of fresh whole blood at various heparin levels when dry kaolin is rubbed onto the membrane to increase its weight by 9%
Figure 20:
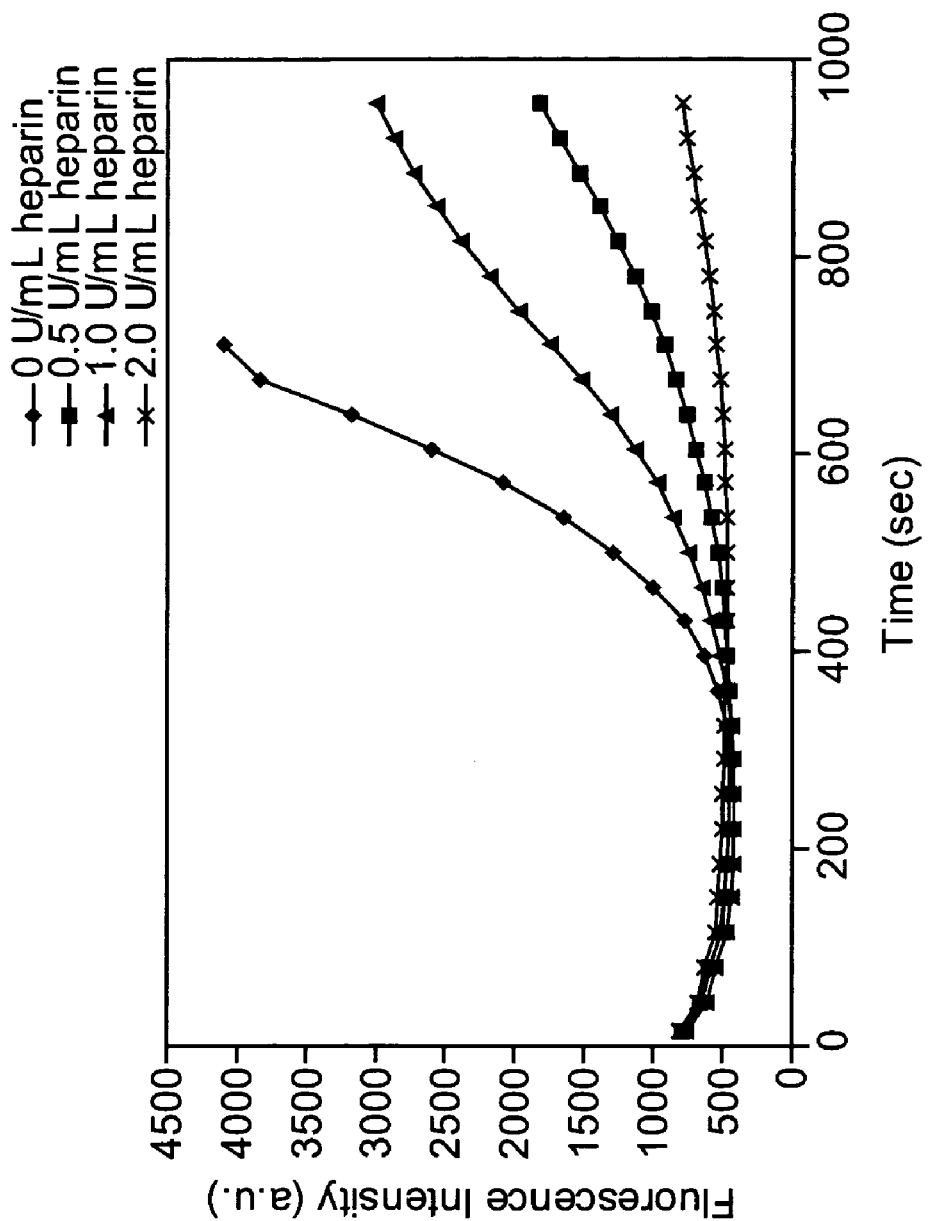
FIG. 20 is a graph of raw fluorescence versus time for samples of fresh whole blood at various heparin levels when dry kaolin is rubbed onto the membrane to increase its weight by 2%
Figure 21:
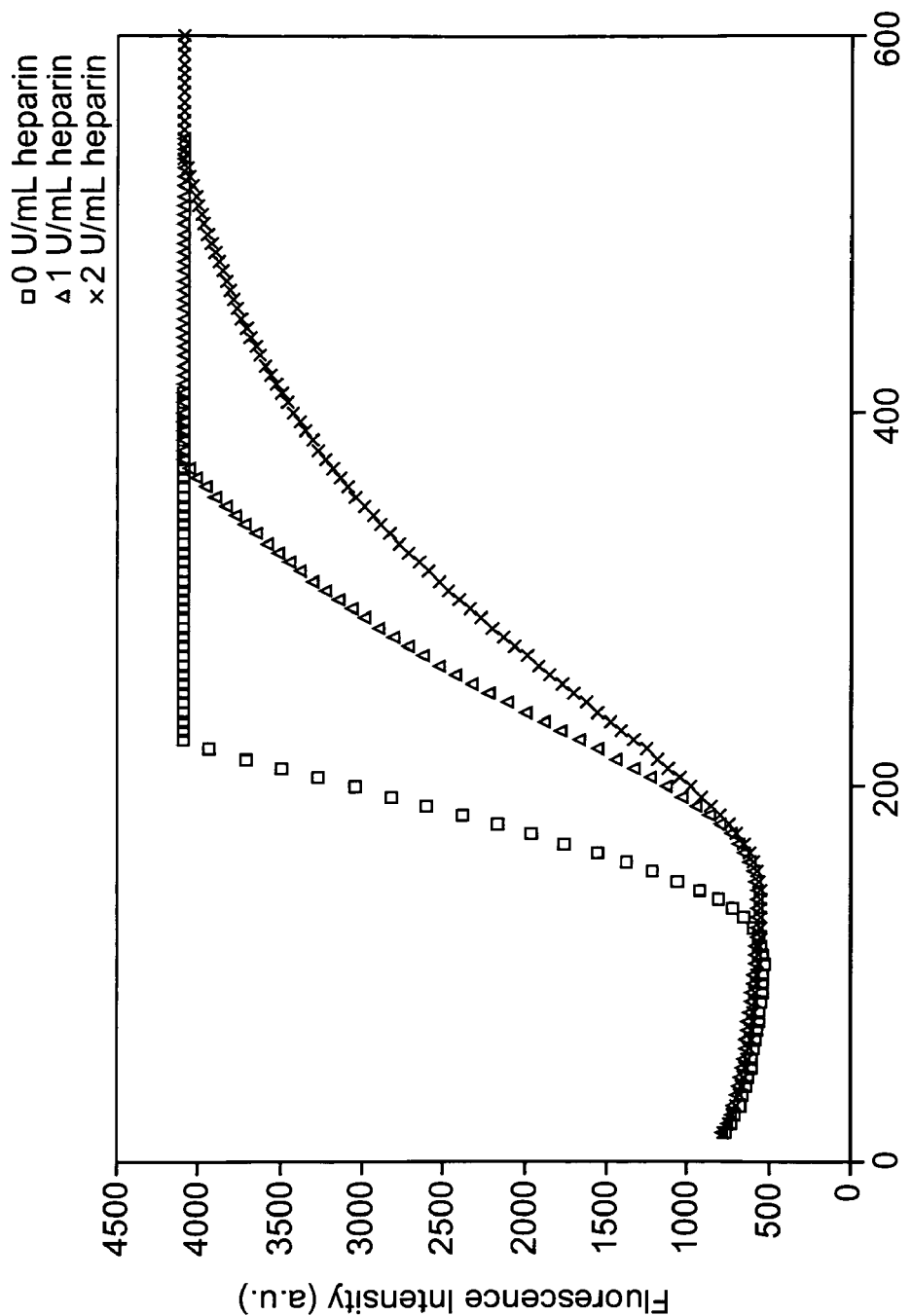
FIG. 21 is a graph of raw fluorescence versus time for samples of fresh whole blood at various heparin levels applied to a membrane to which a 4% suspension of kaolin has been applied by airbrush.
Figure 22:
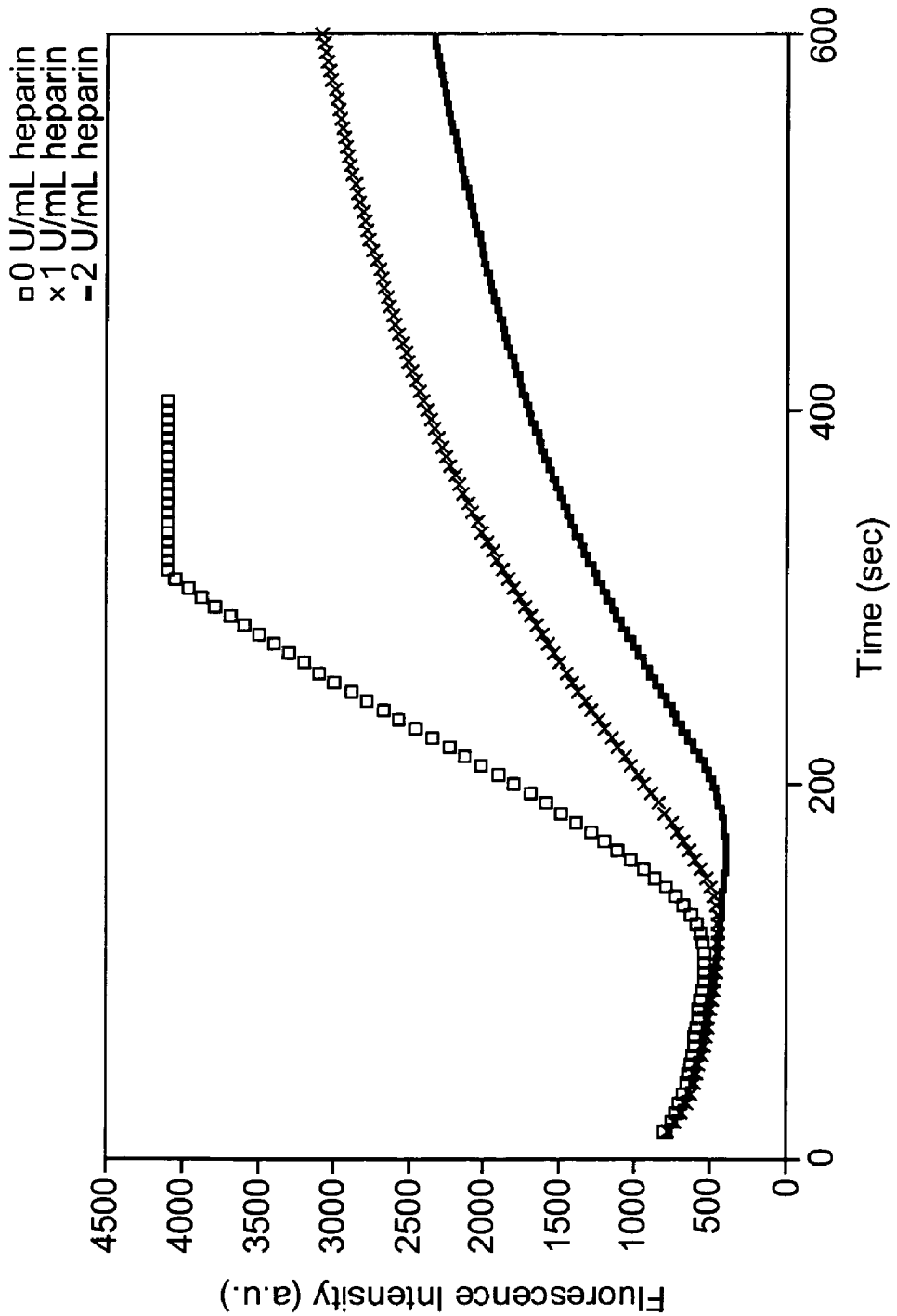
FIG. 22 is a graph of raw fluorescence versus time for samples of fresh whole blood at various heparin levels applied to a membrane to which an 8% suspension of kaolin has been applied by airbrush.
Figure 23:
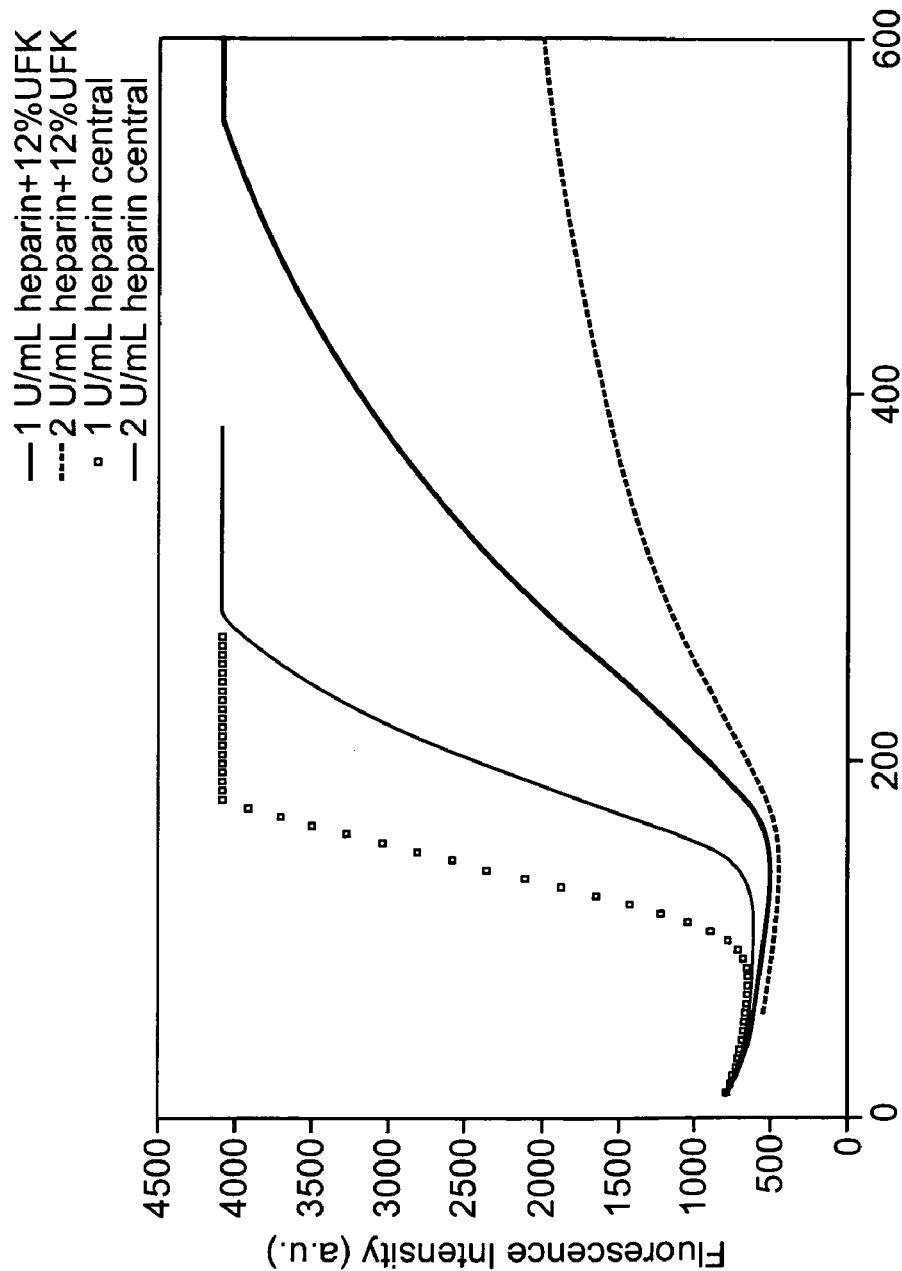
FIG. 23 is a graph of raw fluorescence versus time for samples of fresh whole blood at various heparin levels applied to a membrane to which a 12% suspension of kaolin has been applied by airbrush.
Figure 24:
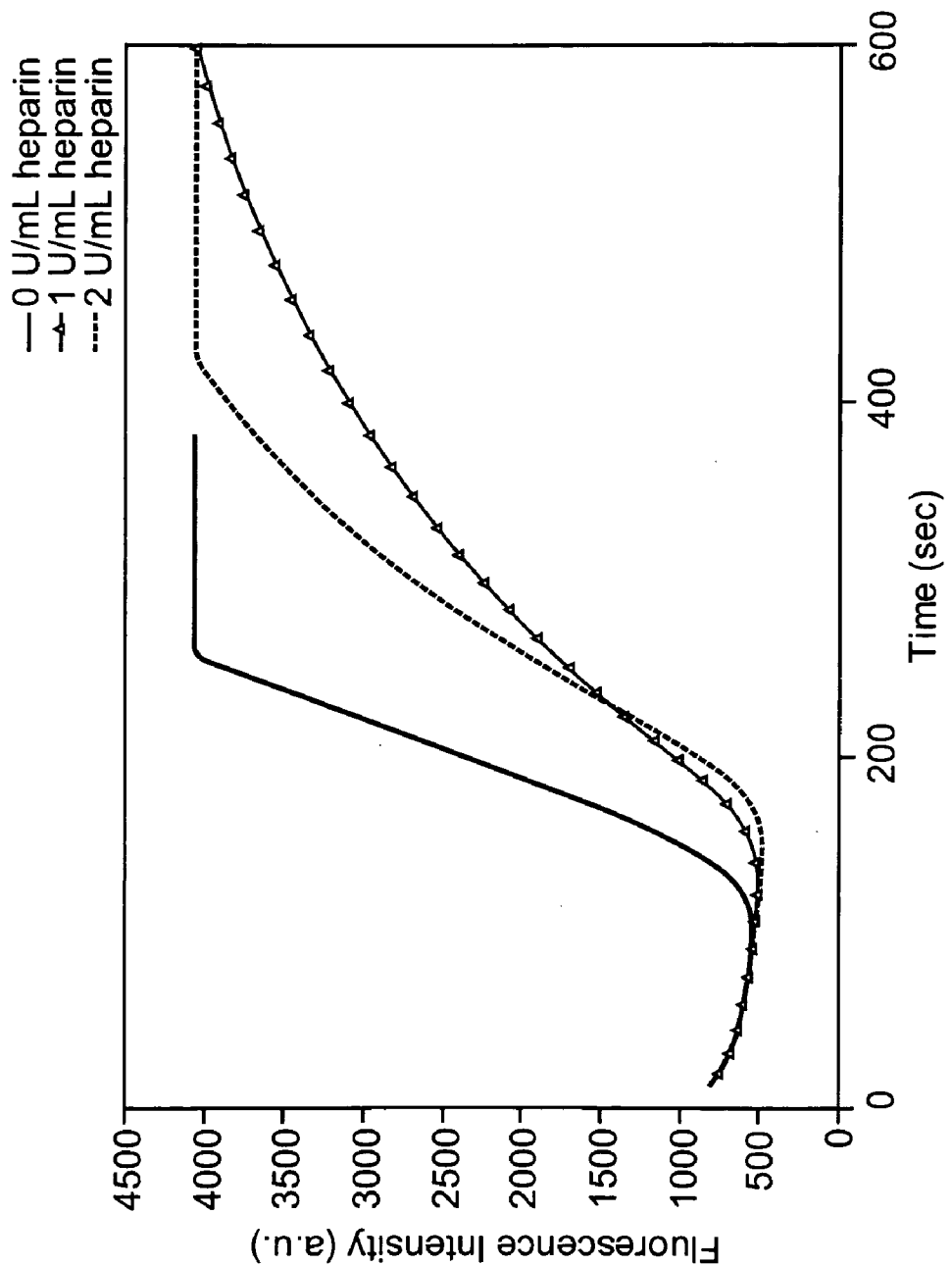
FIG. 24 is a graph of raw fluorescence versus time for samples of fresh whole blood at various heparin levels applied to a membrane to which a 16% suspension of kaolin has been applied by airbrush.

Samples of 15 microliters at each heparin level were pipetted onto the first area of the strips. The results are shown in FIGS. 18-20. FIG. 18 shows the results for the membrane with the highest kaolin level, having a 20% weight increase. The membrane of FIG. 19 had a 9% weight increase, while the membrane of FIG. 20 had a 2% weight increase. While all three membranes produced good fluorescence results, the membrane of graph 18 demonstrates the best combination of rising fluorescence and separation of lines for different heparin levels, including high heparin levels.

Example 7

Airbrushed Kaolin Concentration Study

BTS-25 membranes were coated on both sides with substrate by dipping as described above. The membranes were dried and assembled into strips with the smooth side of the membrane providing the first area for receiving samples.

Four concentrations of Kaolin suspension were prepared by combining ultrafine kaolin (UFK) with ACT-Hepes buffer (60 mM Hepes, 90 mM Sodium Chloride, 0.05% Sodium Azide and pH7.4) to produce 4%, 8%, 12% and 16% kaolin suspensions.

The kaolin suspension was applied to the strips by spraying the first membrane area through the strip window. One shot of approximately one second was applied using an airbrush at 10 psi as in Example 5. Strips were dried in a 37° C. oven for 10 minutes, then for about one hour or more at room temperature.

Samples of whole blood were combined with heparin to produce samples with 0, 1.0 and 2.0 Units/ml heparin. The samples were applied to the strips and the fluorescence results were read with the meter.

The results are shown in FIGS. 21-24. (There are no results for the 12% kaolin concentration for 0 Units/ml heparin because of a computer malfunction) All concentrations produced rising fluorescence with separation of the different heparin levels. However, the 8% and 12% concentrations demonstrated better separation than the 4% kaolin. The 12% concentration produced a greater rise in fluorescence than the 8% concentration. However, the 16% kaolin concentration produced no improvement over the 12% concentration.

Example 8

Kaolin-Rhodamine 110 Interaction

A solution of Rhodamine 110 without peptide was prepared and added to a test tube. The Rhodamine-110 appeared pink. Dry ultrafine kaolin powder, which appeared white, was added to the test tube and mixed with the Rhodamine-110 solution. Because kaolin does not dissolve, it settled into the bottom of the test tube. The kaolin changed color from white to pink, while the Rhodamine-110 solution became clear. If there were no interaction between these two components, the kaolin would be expected to stay white and the Rhodamine-110 would remain pink. The color change of the kaolin and the Rhodamine-110 indicated that an interaction had occurred.

Example 9

Lateral Flow Configuration

BTS-25 membranes were coated with substrate by dipping. Substrate was coated on both the smooth and rough sides of the membrane. After coating, they were dried in the oven at 37° C. for 7 to 8 minutes, then dried at room temperature for another 10 minutes. After drying, they were cut into 2×1 cm pieces.

An additional window (lateral flow window 21; see FIG. 25) was cut out of the top plastic sheet for the strip. The additional window was adjacent to the 2 mm sample area window 20, already present in the plastic sheets. The additional window was of equal width as the sample area window and was 3 mm long. The original sample window is 2 mm and the adjacent lateral flow window is 5 mm from the center of the original sample window. Ultra fine Kaolin was loaded on to the adjacent lateral flow window by pipette or by airbrush then dried in the 37° C. Blood samples with 1 U/ml heparin were applied to the lateral flow window. The samples flowed laterally to the second membrane area, directly opposite of the sample window to react with thrombin substrate for detection.

Figure 25:
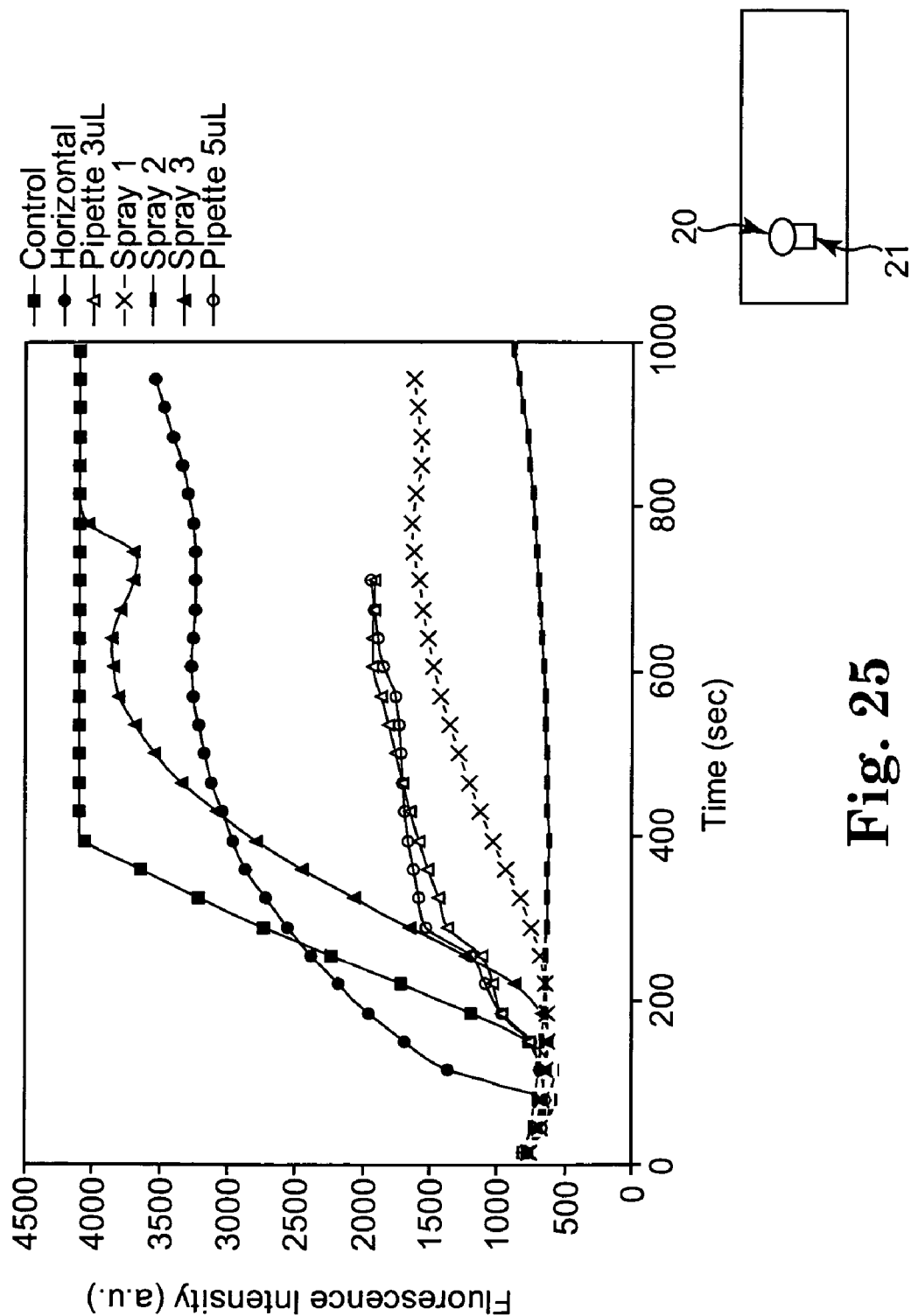
FIG. 25 is a graph of fluorescence versus time for fresh whole blood containing 1 U/ml of heparin with dry kaolin applied by various techniques to various locations and in various concentrations for a lateral flow membrane design.

The results are shown in FIG. 25. Kaolin pre-mixed with the sample served as the control. The membrane prepared by loading kaolin onto the sample window by pipette and then drying it generated the lowest fluorescence signal Loading kaolin by pipette or airbrush onto the lateral window produced fluorescent signals more comparable to that produced by the pre-mixed kaolin test. The results demonstrate that a lateral flow membrane design can be used as one embodiment of this invention.

Example 10

Substrate Concentration Study for ACT

Three concentrations of substrate solution were prepared by diluting (tos-gly-pro-arg)$_2$ Rhodamine-110 as follows:
0.05 mM substrate was prepared by mixing 0.025 ml substrate with 0.975 ml basic buffer
0.1 mM substrate was prepared by mixing 0.05 ml substrate with 0.95 ml basic buffer.

BTS-25 membranes were coated on both sides with substrate by dipping as described above. The membranes were dried in a 37° C. oven for 10 minutes, and then dried at room temperature for about one hour or more. The membranes were assembled into strips and a 12% suspension of ultrafine kaolin was applied to the smooth side of the membrane using one shot from the air brush as in Example 5.

Figure 26:
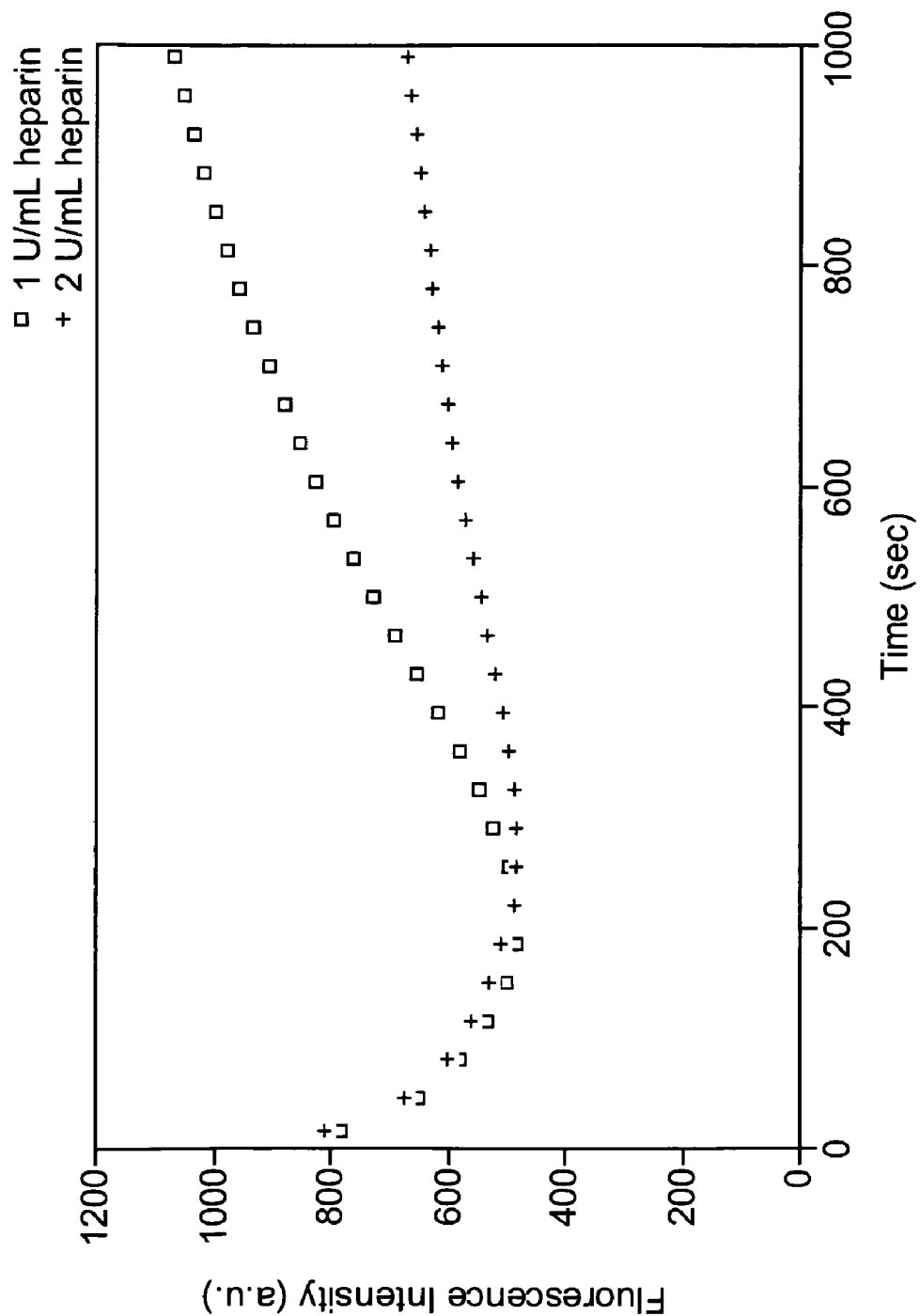
FIG. 26 is a graph of fluorescence versus time for fresh whole blood samples containing 1 and 2 Units/ml heparin for strips prepared with a 0.05 mM substrate solution.
Figure 27:
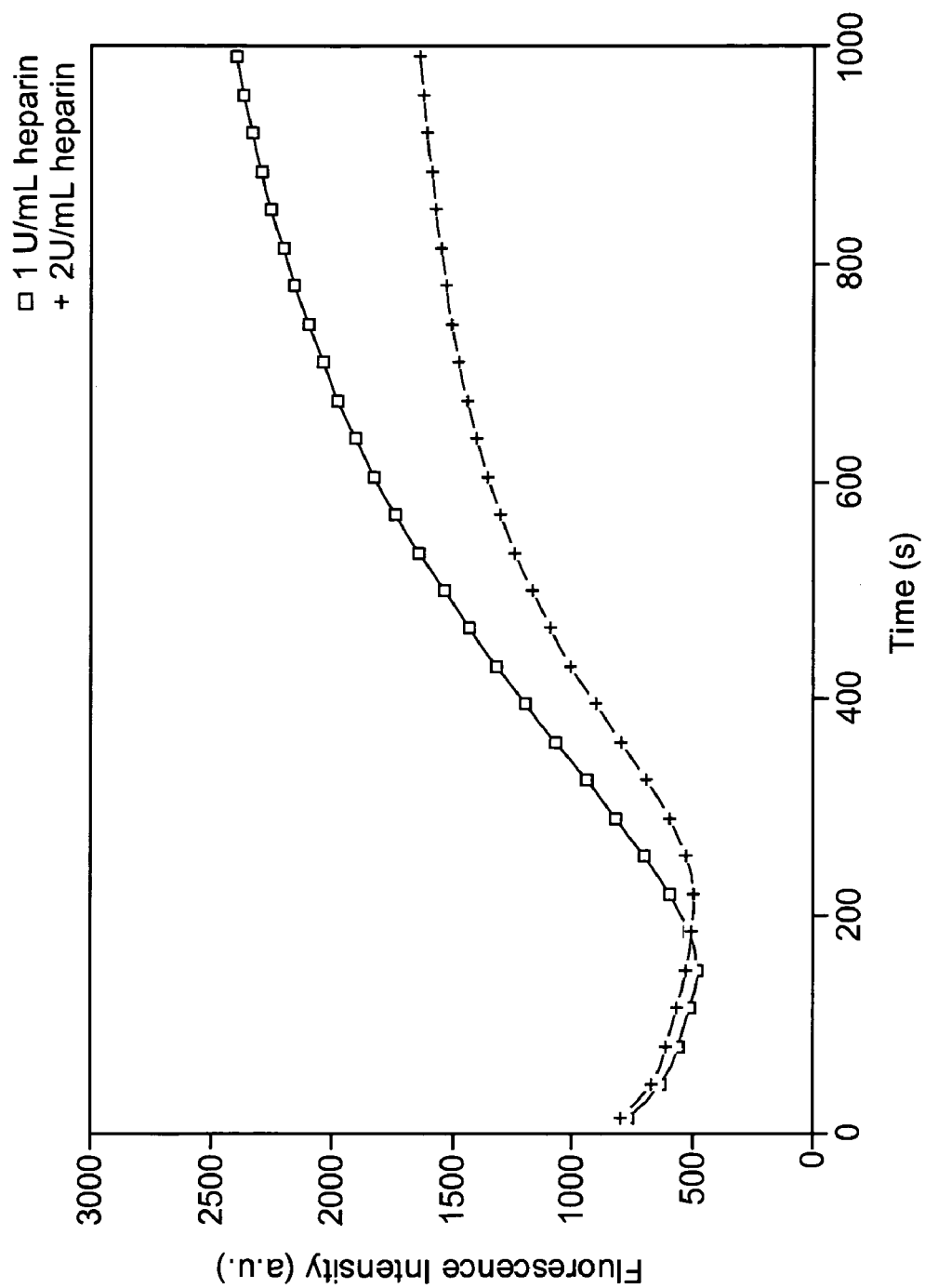
FIG. 27 is a graph of fluorescence versus time for fresh whole blood samples containing 1 and 2 Units/ml heparin for strips prepared with a 0.1 mM substrate solution.

Two sets of blood samples were prepared for each membrane by combining fresh whole blood with unfractionated heparin to produce samples with 1 and 2 Units/ml heparin. In addition, for the 0.05 mM substrates, blood sample pre-mixed with HR-ACT kaolin were also tested as a control condition to compare with the condition without kaolin pre-mixing. Blood samples of 15 microliters were then applied to strips and fluorescence was read by a meter. Duplicates were run for each level of heparin. The results are shown in FIGS. 26-27. The experiment was also conducted for higher concentrations of substrate in Example 11 below.

Example 11

Substrate Concentration Study for ACT

Three concentrations of substrate solution were prepared by diluting (tos-gly-pro-arg)$_2$ Rhodamine-110 as follows:
0.2 mM substrate was prepared by mixing 0.1 ml substrate with 0.9 ml basic buffer
0.3 mM substrate was prepared by mixing 0.15 ml substrate and 0.85 ml basic buffer
0.4 mM substrate was prepared by mixing 0.2 ml substrate with 0.8 ml basic buffer.

BTS-25 membranes were coated on both sides with substrate by dipping as described above. Membranes were air dried then assembled into strips. One spray of a 12% suspension of ultrafine kaolin was applied to the smooth side of the membrane using the air brush as in Example 5.

Figure 28:
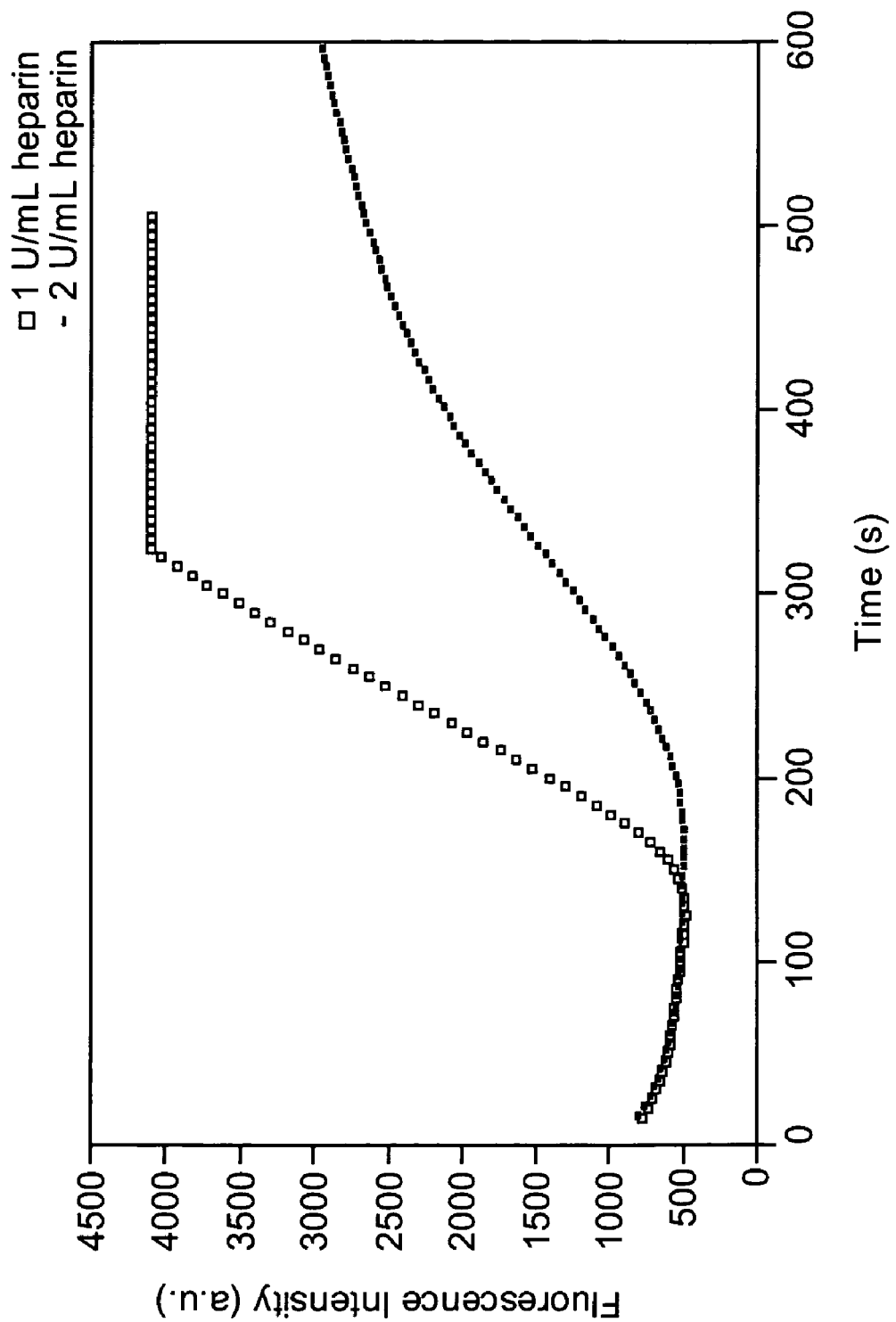
FIG. 28 is a graph of fluorescence versus time for fresh whole blood samples containing 1 and 2 Units/ml heparin for strips prepared with a 0.2 mM substrate solution.
Figure 29:
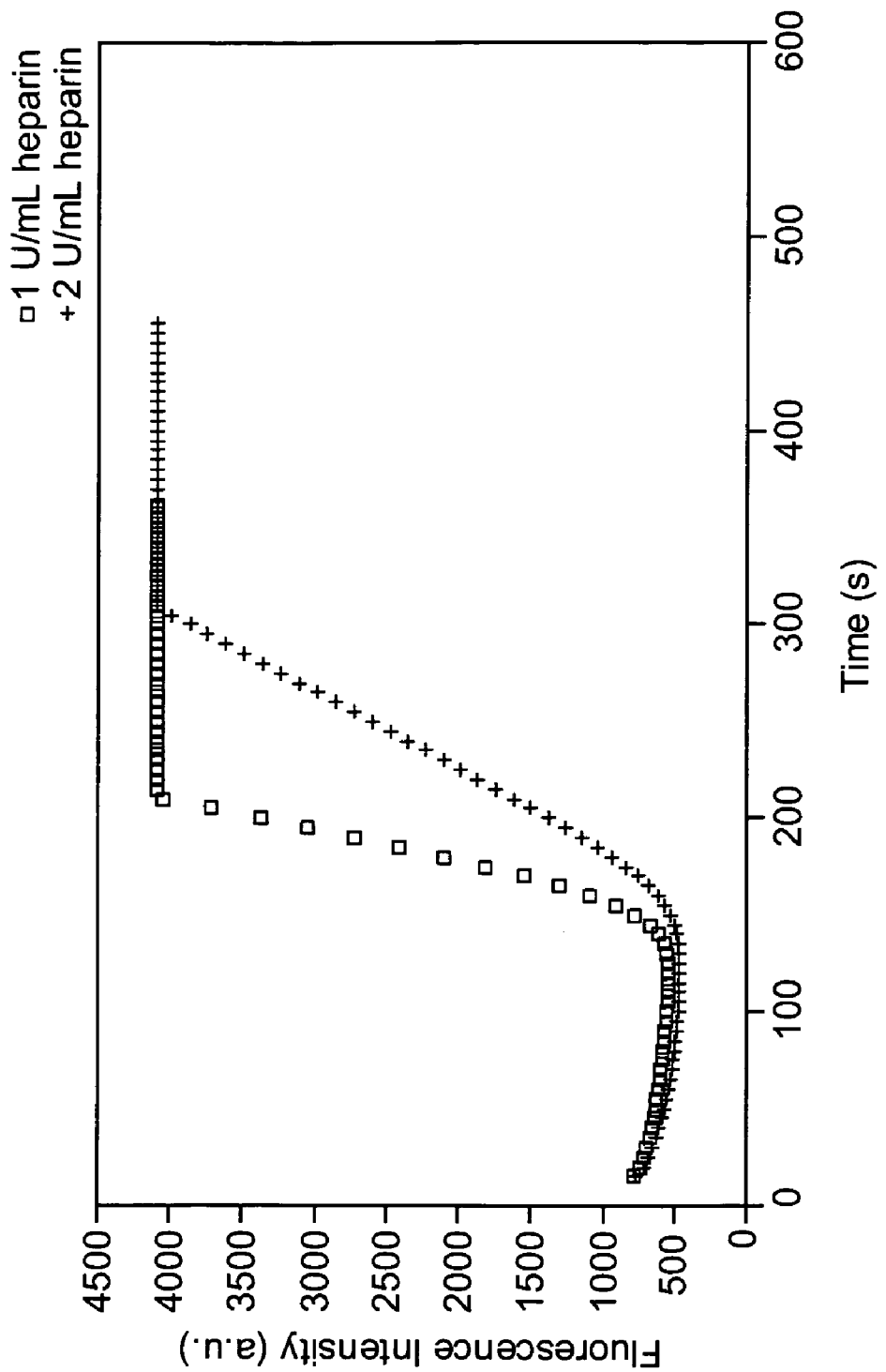
FIG. 29 is a graph of fluorescence versus time for fresh whole blood samples containing 1 and 2 Units/ml heparin for strips prepared with a 0.3 mM substrate solution.
Figure 30:
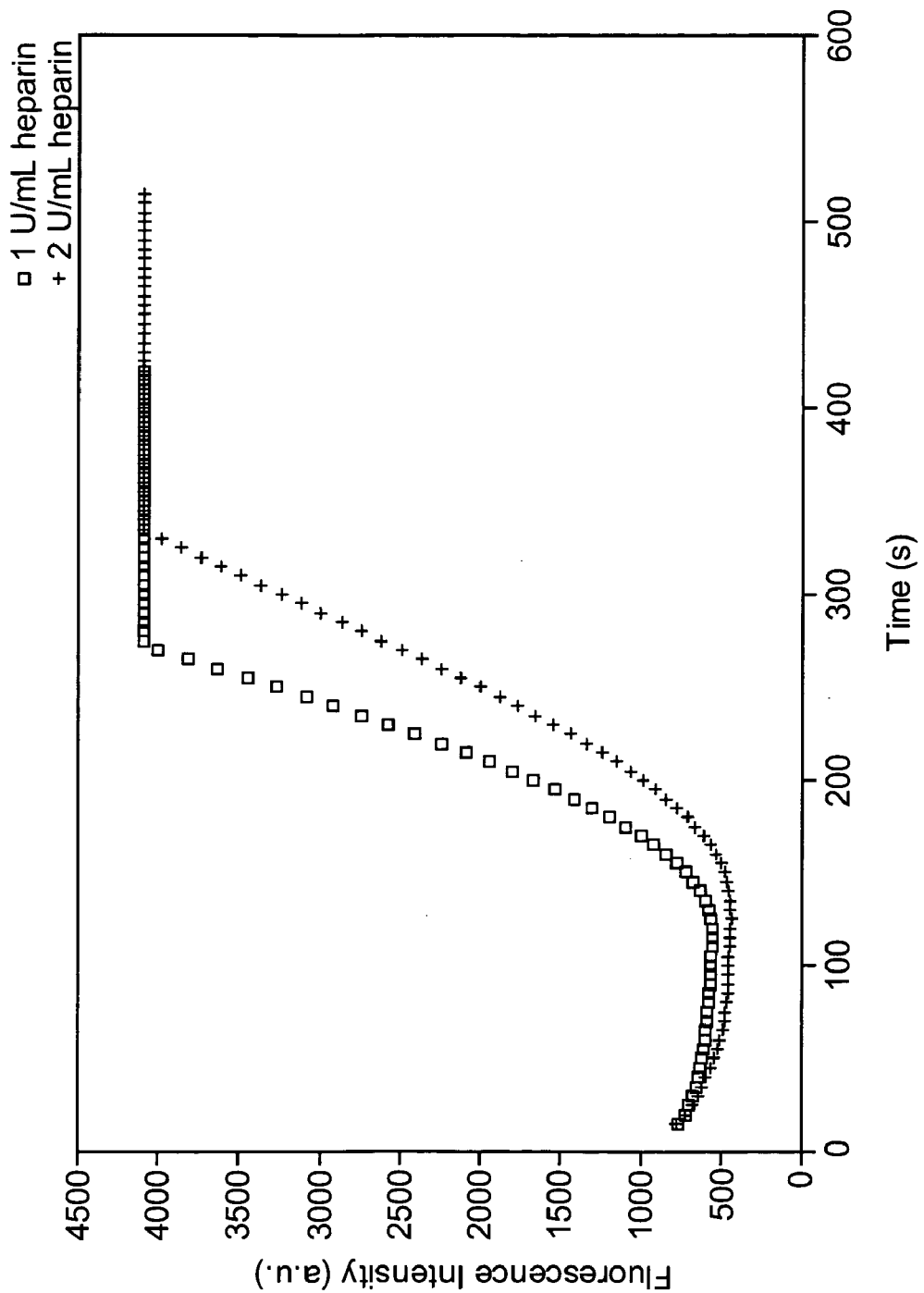
FIG. 30 is a graph of fluorescence versus time for fresh whole blood samples containing 1 and 2 Units/ml heparin for strips prepared with a 0.4 mM substrate solution.

Three sets of blood samples were prepared for each membrane by combining fresh whole blood with unfractionated heparin to produce samples with 0, 1, and 2 U/ml heparin. Blood samples of 15 microliters were applied to strips and fluorescence was read by the meter. Duplicate measurements were made for each heparin level. The results are shown in FIGS. 28-30. Results indicate that for an airbrushed suspension of 12% kaolin, the 0.2 mM substrate solution produced superior results.

Increasing the substrate concentration from 0.05 mM or from 0.1 mM to 0.2 mM results in a faster rise if fluorescence. However, increasing the substrate concentration from 0.2 mM to 0.3 mM or 0.4 mM results in a loss of distinction between the results for samples containing 1 Unit/ml of heparin compared to 2 Units/ml of heparin. At the higher substrate concentrations, the prolongation of fluorescence increase is lost. Applicants believe that this is due to the competition between heparin and the substrate for thrombin. When substrate levels are high, thrombin is consumed by the substrate before the heparin can cause the thrombin level to be reduced. As a result, fluorescence increases quickly without being suppressed by heparin. As shown in FIG. 27 (previous example) and 28, the substrate concentrations of 0.1 mM and 0.2 mM gave better results than other substrate concentrations. At higher concentrations (FIGS. 29 and 30), there was a loss of resolution between the heparin levels. At lower concentrations (FIG. 26 of the previous example), the rise in fluorescence was slow in the samples with higher heparin levels.

Example 12

Effect of Addition of Antithrombin III to Membranes

A 0.2 mM substrate solution was prepared as described in Example 10. The substrate solution was coated onto the rough side only of BTS-25 membranes by dipping. After drying, the membranes were assembled into strips with the smooth side of the membrane providing the first area to receive sample.

Antithrombin III (ATIII) solution was prepared by reconstitution lyophilized material with de-ionized water. 5 microliters of ATIII solution was pipetted through the window onto the first membrane area of the strips and the strips were dried for 45-50 minutes at 37° C. No ATIII solution was applied to the control strips.

A single 1 second shot of 12% kaolin suspension with 10 mM Calcium was applied to the first sample area on the smooth side of the membrane using an airbrush as in Example 5. The strips were dried for 10 minutes at 37° C., and then overnight at room temperature.

Figure 31:
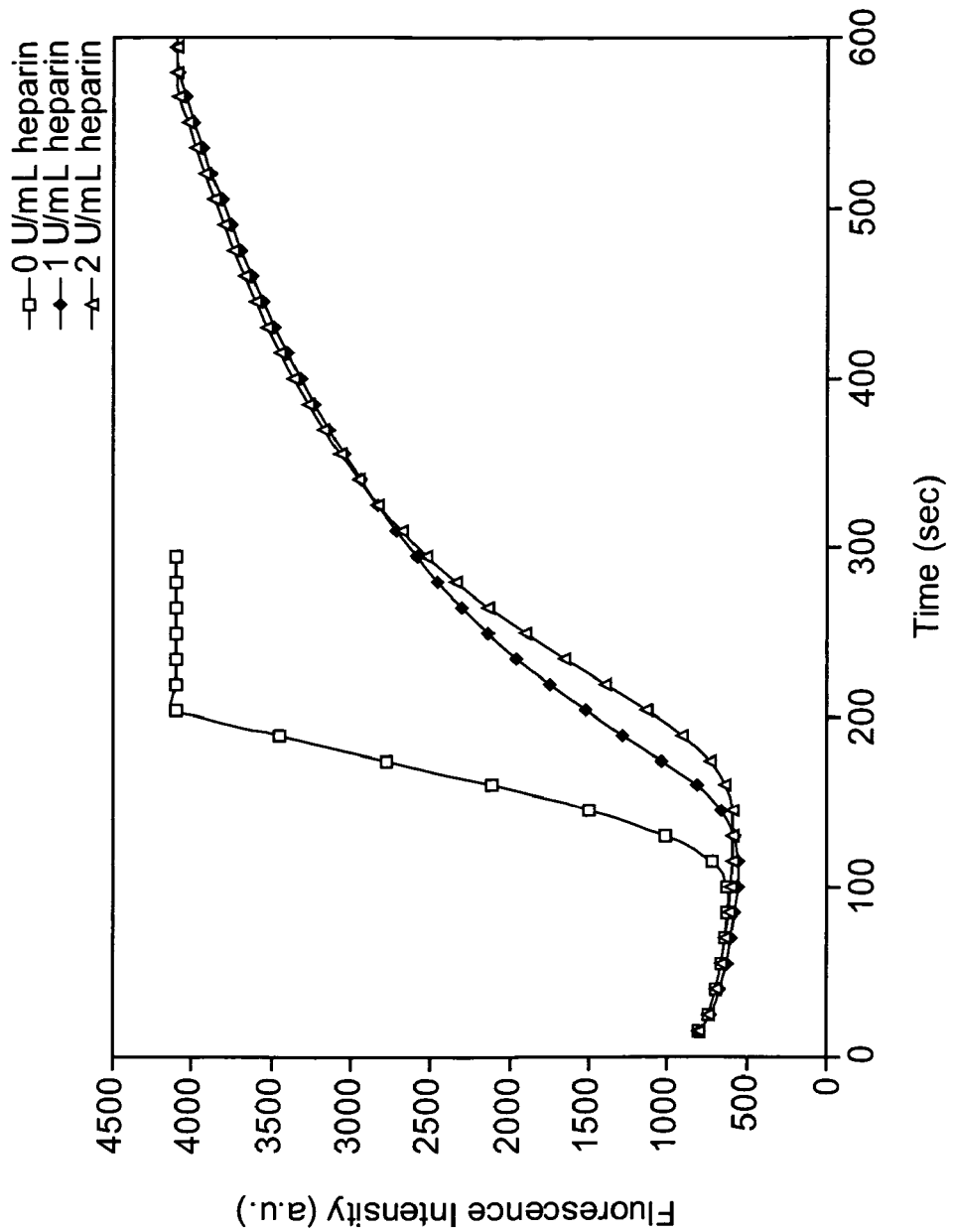
FIG. 31 is a graph of fluorescence versus time for samples of fresh whole blood containing 0, 1 and 2 Units/ml heparin for strips with ultrafine kaolin (UFK) spay but without antithrombin III (ATIII).
Figure 32:
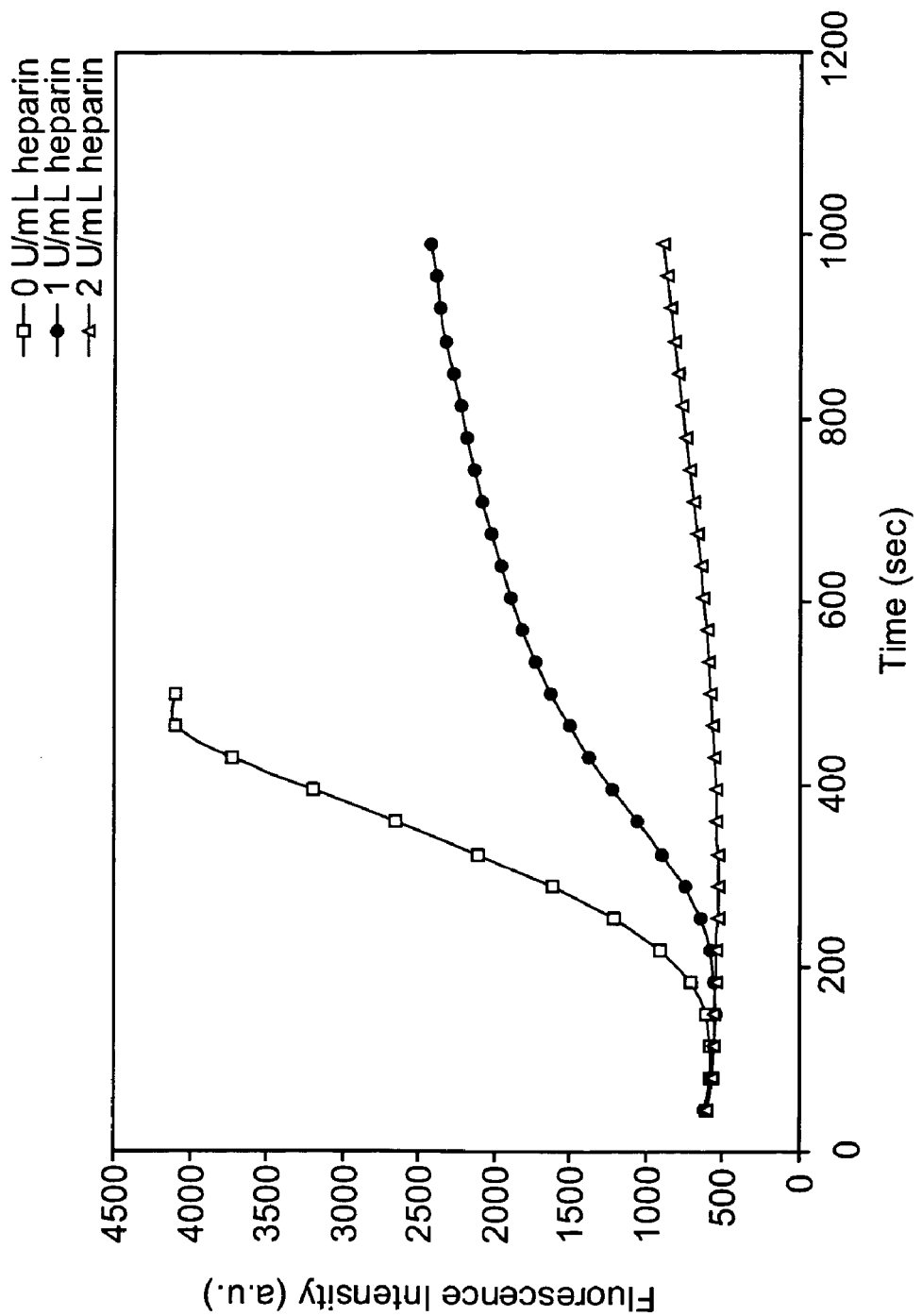
FIG. 32 is a graph of fluorescence versus time for samples of fresh whole blood containing 0, 1 and 2 Units/ml heparin for strips with one spray of 12.0% ultrafine kaolin (UFK) and coated with 1×5 μL antithrombin III (ATIII).

Fresh whole blood was combined with unfractionated heparin to produce samples containing 0, 1.0 and 2.0 Units/ml heparin. Blood samples of 15 microliters were applied to the strips and fluorescence was read by the meter. The results for the control strips without ATIII are shown in FIG. 31 while the results of the test strips including ATIII are shown in FIG. 32. The strips containing ATIII showed improved resolution of the samples containing different heparin levels.

Example 13

Comparison of Algorithms for Calculating Coagulation Test Results

BTS-25 membranes were coated with 0.2 mM substrate on the rough side by dipping, as described above. The membranes were assembled into strips with the smooth side of the membrane providing the first membrane area to receive blood sample.

Samples of fresh whole blood were prepared with the following heparin concentrations: 0, 1, 2, 4 and 6 Units/ml heparin. The samples were pre-mixed with HR-ACT kaolin in the HR-ACT cartridges as described above. Samples of 15 microliters were applied to the strips and fluorescence was monitored by the meter.

Figure 34:
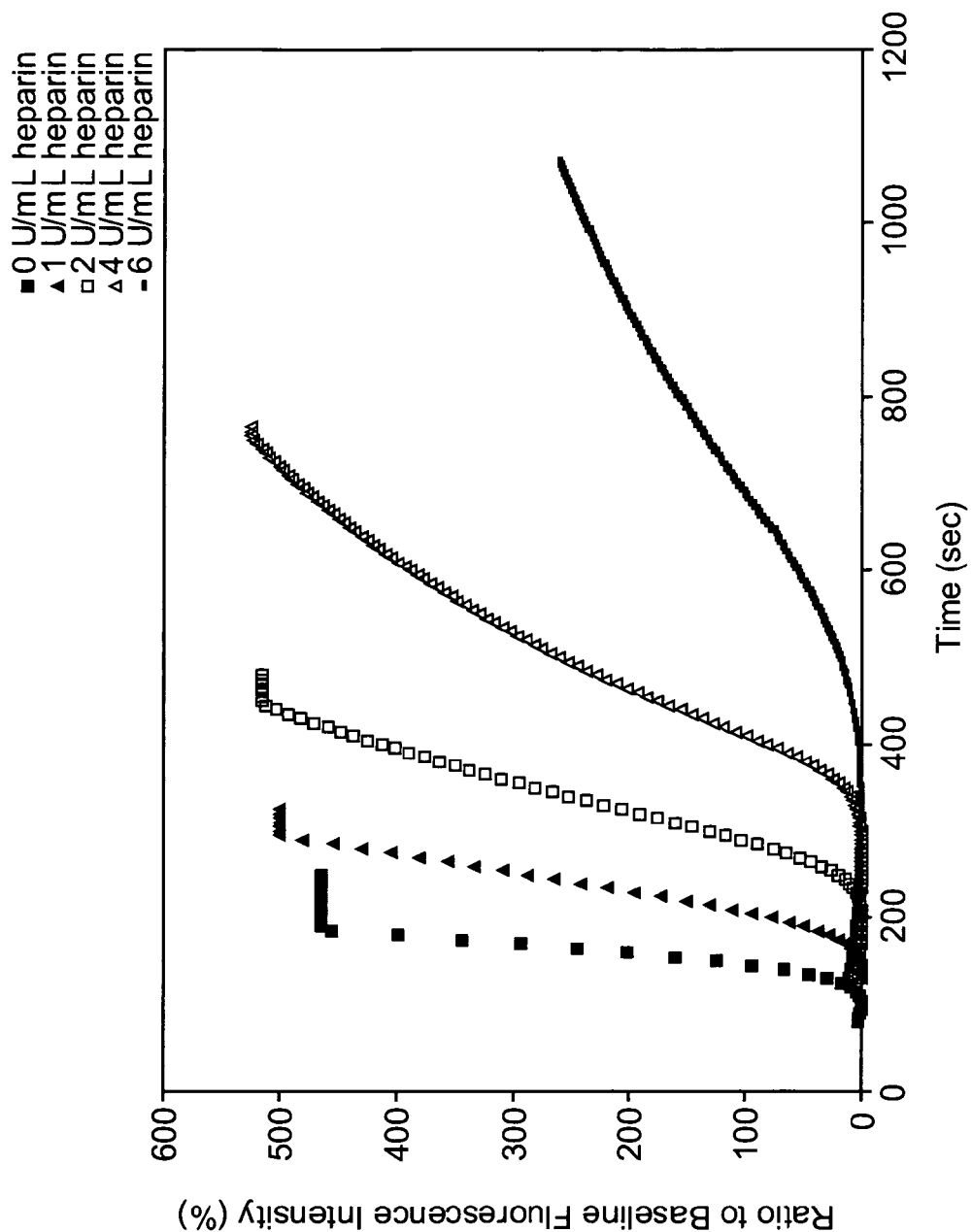
FIG. 34 is a graph replotting the data from FIG. 31 as ratio of baseline (minimum) fluorescence intensity versus time.
Figure 35:
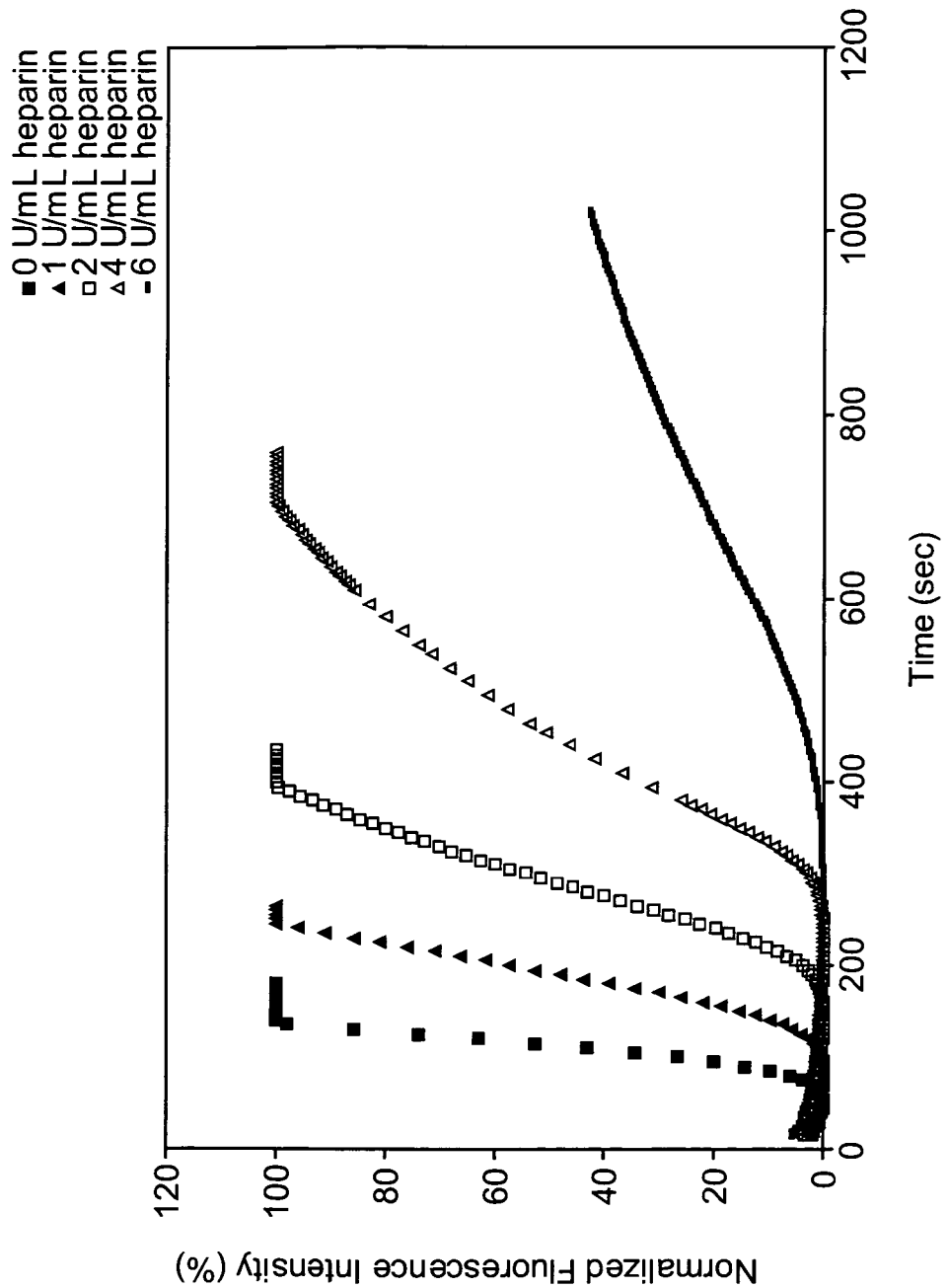
FIG. 35 is a graph replotting the data from FIG. 31 as percent normalized fluorescence intensity versus time.

A graph of raw fluorescence intensity data versus time for the blood samples containing heparin levels of 0 through 6 Units/ml is shown in FIG. 33. This data was used to calculate the fluorescence ratio of this invention and the fluorescence ratio was plotted versus time in FIG. 34. The shape and separation of the different blood samples profiles is similar for FIGS. 33 and 34. In FIG. 35, the data of FIG. 33 were used to calculate the normalized fluorescence according to the prior art method and the results were plotted against time. FIG. 35 shows that the results are skewed such that the time to result is shortened due to normalization. This skewing may result in inaccurate results. The method of this invention is quicker and does not result in skewing and therefore produces superior results.

All publications, patents and patent applications are incorporated herein by reference. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations, which fall within the spirit and broad scope of the invention.

What is claimed is:

1. An article for testing a coagulation process in a whole blood sample including red blood cells, the article comprising:
   one or more permeable membranes having a first area onto which a whole blood sample is applied and including a first pore, a second area from which a detectable signal is obtained and including a second pore, wherein the first pore has a smaller size rating than the second pore, and wherein the first pore has a size rating effective to exclude a red blood cell included in the whole blood sample;

a coagulation initiator provided on the first area in a manner effective to stimulate coagulation of the whole blood sample external to the first pore when the whole blood is applied to the first area; and a substrate associated with the one or more membranes, wherein the substrate reacts with a coagulation cascade component in the blood to produce a detectable signal on the second area; and wherein the substrate is physically separated from the coagulation initiator.

2. The article of claim 1, wherein the first pore size rating is between about 0.1 and about 1 micrometer.

3. The article of claim 2, wherein the first pore size rating is between about 0.4 and about 0.6 micrometer.

4. The article of claim 1, wherein the substrate is a fluorogenic Factor Xa substrate, and wherein the signal is fluorescence which is used to determine heparin concentration in the whole blood.

5. The article of claim 1, wherein the substrate is a fluorogenic thrombin substrate, and wherein the signal is fluorescence which is used to determine a direct thrombin inhibitor concentration in the whole blood.

6. The article of claim 1, wherein the coagulation initiator is kaolin, Celite or a combination thereof.

7. The article of claim 6, wherein the substrate is a thrombin substrate and the detectable signal is used to determine an Activated Clotting Time.

8. The article of claim 1, wherein the coagulation initiator is Ecarin and the detectable signal is used to determine an Ecarin time.

9. The article of claim 1, wherein the coagulation initiator is Russell's viper venom, the substrate is a Factor Xa substrate, and the detectable signal is used to monitor Factor Xa specific clotting time.

10. The article of claim 1, wherein the substrate is a thrombin substrate and the coagulation initiator comprises a phospholipid, silica or ellagic acid, either individually or in combination, and the detectable signal is used to derive an Activated Partial Thromboplastin Time.

11. The article of claim 1, wherein the substrate is cleavably linked to a fluorophore.

12. The article of claim 11, wherein the fluorophore is negatively charged or neutral.

13. The article of claim 1, wherein the article is for testing a Prothrombin Time and an International Normalized Ratio (INR).

14. The article of claim 1, wherein the article comprises a single membrane.

15. The article of claim 1, wherein the article comprises first and second membranes.

16. The article of claim 1, wherein the coagulation initiator is provided on a first membrane and the substrate is provided on a second membrane.

17. An article for testing a coagulation process in whole blood, the article comprising:

one or more permeable membranes having a first area including pores, a second area including pores, and channels connecting the pores of the first area with the pores of the second area; and a substrate and a coagulation initiator associated with the one or more membranes, wherein the substrate is capable of reacting with a coagulation cascade component to produce a detectable signal on the second area and wherein the substrate is physically separated from the coagulation initiator; and wherein whole blood is applied to the first area and the pores in the first area have a pore size rating of between about 0.1 and about 1 micrometer.

18. The article of claim 17, wherein the pores of the first area have a pore size rating of between about 0.4 and about 0.6 micrometer.

19. The article of claim 17, wherein the substrate is a fluorogenic Factor Xa substrate, and wherein the signal is fluorescence which is used to derive heparin concentration in the whole blood.

20. The article of claim 17, wherein the substrate is a fluorogenic thrombin substrate, and wherein the signal is fluorescence which is used to determine a direct thrombin inhibitor concentration in the whole blood.

21. The article of claim 17, wherein the coagulation initiator is kaolin, Celite or a combination thereof.

22. The article of claim 17, wherein the substrate is a thrombin substrate and the detectable signal is used to determine Activated Clotting Time.

23. The article of claim 17, wherein the coagulation initiator is Ecarin and wherein the detectable signal is used to derive an Ecarin time.

24. The article of claim 17, wherein the coagulation initiator is Russell's viper venom and the substrate is a Factor Xa substrate, and wherein the detectable signal is used to determine Factor Xa specific clotting time.

25. The article of claim 17, wherein the substrate is a thrombin substrate and the coagulation initiator comprises a phospholipid, silica or ellagic acid, either individually or in combination, and the detectable signal is used to derive an Activated Partial Thromboplastin Time.

26. The article of claim 17, wherein the substrate is cleavably linked to a fluorophore.

27. The article of claim 26, wherein the fluorophore is negatively charged or neutral.

28. The article according to claim 17, wherein the article is for testing a Prothrombin Time and an International Normalized Ratio (INR).

29. An article for testing a coagulation process in whole blood, the article comprising:

a permeable membrane having a first area including pores, a second area including pores and channels connecting the pores of the first area with the pores of the second area; and a substrate and a coagulation initiator associated with the membrane, wherein the substrate reacts with a coagulation cascade component in the blood to produce a detectable signal on the second area of the membrane and wherein the substrate and the coagulation initiator are physically separated; and wherein the pores of the first area have a smaller diameter than the pores of the second area and substantially exclude red blood cells from entering the channels.

30. The article of claim 29, wherein the pores of the first area substantially exclude platelets.

31. The article of claim 30, wherein the pores of the first area have a pore size rating in the range of about 0.1 to about 1 micrometer.

32. The article of claim 31, wherein the pore size rating is in the range of about 0.4 to about 0.6 micrometer.

33. The article of claim 29, wherein the substrate is a fluorogenic Factor Xa substrate, and wherein the signal is fluorescence which is used to determine heparin concentration in the whole blood.

34. The article of claim 29, wherein the substrate is a fluorogenic thrombin substrate, and wherein the signal is fluorescence which is used to determine a direct thrombin inhibitor concentration in the whole blood.

35. The article of claim 29, wherein the coagulation initiator is kaolin.

36. The article of claim 35, wherein the substrate is a thrombin substrate and the detectable signal is used to determine an Activated Clotting Time.

37. The article of claim 29, wherein the coagulation initiator is Ecarin and wherein the detectable signal is used to derive an Ecarin time.

38. The article of claim 29, wherein the substrate is a Factor Xa substrate, and wherein the detectable signal is used to monitor a Factor Xa specific clotting time.

39. The article of claim 29, wherein the substrate is a thrombin substrate and the coagulation initiator comprises a phospholipid, silica or ellagic acid, either individually or in combination, and wherein the detectable signal is used to derive an Activated Partial Thromboplastin Time.

40. The article of claim 29, wherein the signal producing substrate is cleavably linked to a fluorophore.

41. The article of claim 40, wherein the fluorophore is negatively charged or neutral.

42. An article for testing a coagulation process in whole blood, the article comprising:
   a permeable membrane having a first area including pores, a second area including pores and channels connecting the pores of the first area with the pores of the second area;
   a coagulation initiator provided on the first area and
   a substrate associated with the membrane, wherein the substrate is capable of reacting with a coagulation cascade component in the blood to produce a detectable signal on the second area of the membrane and wherein the substrate is physically separated from the coagulation initiator; and
   wherein the pores of the first area have a smaller diameter than the pores of the second area; and
   wherein the pores of the first area substantially exclude red blood cells;
   and wherein whole blood is applied to the first area of the membrane.

43. The article of claim 42, wherein the coagulation cascade component is a proteolytic enzyme.

44. The article of claim 43, wherein the proteolytic enzyme is thrombin.

45. The article of claim 42, wherein the coagulation process is prolonged due to hemodilution of the whole blood.

46. The article of claim 42, wherein the article is for testing Prothrombin Time and an International Normalized Ratio (INR).

47. The article of claim 42, wherein the coagulation process of the blood is prolonged due to heparin being present in the blood.

48. The article of claim 47, wherein the heparin concentration in the blood is between about 0 and about 6 units/ml.

49. The article of claim 42, wherein the article is for testing Activated Clotting Time.

50. The article of claim 42, wherein the pores of the first area substantially exclude platelets.

51. The article of claim 42, wherein the pores of the first area have a pore size rating of between about 0.1 and about 1 micrometer.

52. The article of claim 51, wherein the pore size rating is between about 0.4 and about 0.6 micrometer.

53. The article of claim 42, wherein the substrate is a fluorogenic Factor Xa substrate, and wherein the signal is fluorescence which is used to determine heparin concentration in the whole blood.

54. The article of claim 42, wherein the substrate is a fluorogenic thrombin substrate, and wherein the signal is fluorescence which is used to determine a direct thrombin inhibitor concentration in the whole blood.

55. The article of claim 42, wherein the coagulation initiator is kaolin, Celite, or a combination thereof.

56. The article of claim 55, wherein the substrate is a thrombin substrate and the detectable signal is used to determine an Activated Clotting Time.

57. The article of claim 42, wherein the coagulation initiator is Ecarin and wherein the detectable signal is used to determine an Ecarin time.

58. The article of claim 42, wherein the coagulation initiator is Russell's viper venom and the substrate is a Factor Xa substrate, wherein the detectable signal is used to determine Factor Xa specific clotting time.

59. The article of claim 42, wherein the substrate is a thrombin substrate and the coagulation initiator comprises a phospholipid, silica or ellagic acid, either individually or in combination, and the detectable signal is used to determine an Activated Partial Thromboplastin Time.

60. The article of claim 42, wherein the substrate is cleavably linked to a fluorophore.

61. The article of claim 60, wherein the fluorophore is negatively charged or neutral.

* * * * *